US006335339B1

(12) United States Patent
Arenas et al.

(10) Patent No.: US 6,335,339 B1
(45) Date of Patent: Jan. 1, 2002

(54) TRIAZINE ANTIVIRAL COMPOUNDS

(75) Inventors: Jaime E. Arenas, Lexington; Sharon T. Cload, Cambridge; Elizabeth S. Fleming, Belmont; Yi Bin Xiang, Acton, all of MA (US)

(73) Assignee: Scriptgen Pharmaceuticals, Inc., Waltham, MA (US)

( * ) Notice: Subject to any disclaimer, the term of this patent is extended or adjusted under 35 U.S.C. 154(b) by 0 days.

(21) Appl. No.: 09/229,703

(22) Filed: Jan. 13, 1999

Related U.S. Application Data

(60) Provisional application No. 60/113,656, filed on Jan. 13, 1998.

(51) Int. Cl.[7] ..................................................... A61K 31/53
(52) U.S. Cl. ............................................ 514/245; 514/241
(58) Field of Search ...................................... 514/245, 241

(56) References Cited

U.S. PATENT DOCUMENTS

| | | | |
|---|---|---|---|
| 3,549,760 A | 12/1970 | Albert et al. | .................. 424/249 |
| 4,254,122 A | 3/1981 | Brown | ........................... 424/249 |
| 4,316,015 A | 2/1982 | Hamprecht et al. | .............. 544/7 |
| 4,508,898 A | 4/1985 | Ogilvie | .......................... 544/211 |
| 4,565,815 A | 1/1986 | Kim et al. | ..................... 514/246 |
| 4,703,113 A | 10/1987 | Baxter et al. | .................. 534/796 |
| 5,120,843 A | 6/1992 | McCall et al. | ............... 544/123 |
| 5,162,319 A | 11/1992 | Clough et al. | ............... 514/243 |
| 5,225,405 A | 7/1993 | Paramelle et al. | ........... 514/185 |

FOREIGN PATENT DOCUMENTS

| | | | |
|---|---|---|---|
| DE | 29 30 039 | 2/1980 | ............ A61K/31/53 |
| EP | 0 092 479 | 10/1983 | .......... C07D/251/70 |
| EP | 0 172 608 A1 | 5/1985 | ........................ 487/4 |
| EP | 0 240 854 | 10/1987 | .......... C07D/251/70 |
| EP | 0 505 220 A1 | 9/1992 | .......... C07D/251/70 |
| EP | 0 629 622 A1 | 12/1994 | .......... C07D/401/04 |
| EP | 0 795 549 A1 | 2/1997 | ..................... 251/54 |
| EP | 0 775 487 A1 | 5/1997 | .......... A61K/31/53 |
| WO | 93/10116 | * 5/1993 | .......... C07D/401/14 |
| WO | WO 93/20056 | 10/1993 | .......... C07D/251/70 |
| WO | WO 96/25167 | 8/1996 | |
| WO | WO 97/20825 | 6/1997 | |
| WO | WO 99/00363 | 1/1999 | .......... C07D/207/34 |

OTHER PUBLICATIONS

Toh et al, Nature, vol 305, Oct. 27, 1983 pp. 827–829, 1983.*

Summers et al, Cell, vol 29 pp. 403–415, 1982.*

Patel et al., "Studies on 1,3,5–Triazines as Antibacterial Agents," *J. Inst. Chemists (India)*, vol. 57 (May 1985), pp. 111–112.

Kreutzberger et al., "Antivirale Wirkstoffe," *Arzneim–Forsch./Drug Res. 36*, Nr. 4 (1986), pp. 626–629 (with English language abstract).

Korba et al., "A cell culture assay for compounds which inhibit hepatitis B virus replication," *Antiviral Research 15*, (1991), pp. 217–228.

Korba et al., "Use of a standardized cell culture assay to assess activities of nucleoside analogs against hepatitis B virus replication," *Antiviral Research 19*, (1992), pp. 55–70.

Zapp, et al., "Small Molecules That Selectively Block RNA Binding of HIV–1 Rev Protein Inhibit Rev Function and Viral Production," *Cell*, vol. 74 (Sep. 24, 1993), pp. 969–978.

Bhattacharya et al., "Synthesis of Certain N–and C–Alkyl Purine Analogs," *J. Heterocyclic Chem.*, 30 (1993), 1341–1349.

Purohit et al., "Interactions of a small RNA 3with antibiotic and RNA ligands of the 30S subunit," *Nature*, vol. 370 Aug. 25, 1994), pp. 659–662.

Stage et al., "Inhibition of the hammerhead ribozyme by neomycin," *RNA*, Cambridge University Press (1995), pp. 95–101.

Golankiewicz et al., "Synthesis and Antiviral Activity of Benzyl–Substituted Imidazo[1,5–a]–1,3,5–triazine (5,8–Diaza–7, 9–dideazapurine) Derivatives," *J. Med. Chem. 38* (1995), pp. 3558–3565.

Wang et al., "Specific binding of aminoglycoside antibiotics to RNA,"*Chemistry & Biology*, vol. 2, No. 5 (1993), pp. 282–290.

Wallis et al., "A novel RNA motif for neomycin recognition, "*Chemistry & Biology*, vol. 2, No. 8 (1995), pp. 543–552.

Rogers et al., "Inhibition of the Self–cleavage Reaction of the Human Hepatitis Delta Virus Ribozyme by Antibiotics," *J. Mol. Biol. 259* (1996), pp. 916–925.

Kreutzberger et al., "Antiviral Agents, XXVII: Aminomethynylation of 5–Oxo–2–pyrazoline–3–carboxylic Acid Derivatives," *ARPMAS, Arch. Pharm. GE, 319*, 1 (1986) pp. 18–25 (abstract).

Kreutzberger et al., "Antiviral Drugs/28th Comm.: Aliphatically substituted chlorodihexylamino–1,3,5–triazines," *ARZNAD, Arzneim. Forsch., GE, 36, 4* (1986) 626–629 (abstract).

(List continued on next page.)

Primary Examiner—Russell Travers
(74) Attorney, Agent, or Firm—Darby & Darby

(57) ABSTRACT

The present invention provides pharmaceutical formulations comprising 1,3,5-triazine derivatives. The compounds and formulations of the present invention exhibit a range of activities, including antiviral and antibiotic activities, and the formulations may be used, alone or in combination, as a method of treating a patient in need of antiviral and/or antibiotic therapy. The triazine derivatives of the present invention bind to and inhibit functional nucleic acids, and hence, have broad applicability in the treatment of conditions associated with DNA and RNA viruses.

14 Claims, 93 Drawing Sheets

OTHER PUBLICATIONS

Bhattacharya et al., "Synthesis of Certain N–and C–Alkyl Purine Analogs," *JHTCAD, J. Heterocycl. Chem., EN, 30, 5* (1993) pp. 1341–1350 (abstract).

Golankiewicz et al., "Synthesis and Antiviral Activity of Benzyl–Substituted Imidazo, 1,5–a.–1,3,5–triazine (5,8–Diaza–7,9–dideazapurine) Derivatives," *JMCMAR, J. Med. Chem., EN 38, 18* (1995) pp. 3558–3565 (abstract).

Kreutzberger et al., "Antidiabetische Wirkstoffe. V,1.. Lang–und verzweigtkettig substituierte Chlor–dihexlamino–1,3,5–triazine," *JHTCAD, J. Heterocycl. Chem., GE, 22* (1985) pp. 1441–1444 (abstract).

Bruhin, H., et al."Antituberculosis activity of some nitrofuran derivatives", J. Pharm. Pharmac., 1969, vol. 21, No. 7, pp. 423–433.

Coley, H.M., "N–(Hydroxymethyl) melamines", Chemical Abstracts, 1997, 126:152444f.

Jarman, M et al. "Synthesis and Cytotoxicity of Potential Tumor–Inhibitory Analogs of Trimelamol (2,4,6–Tris[(hydroxymethyl)methylamino] 1,3,5–triazine) Having Electron–Withdrawing Groups in Place of Methyl", J. Med. Chem., 1993, vol. 36, pp. 4195–4200.

Matsuno, T. et al., "Synthesis and Aromatase–Inhibitory Activity of Imidazoyl–1,3,5–triazine Derivatives", Chem. Pharm. Bull., 1997, 45(2)291–296.

Rutty, C. J. et al. "In vitro studies with Hexamethylmelamine", Chem. Abstracts., 1997, 88: 11509s.

Su, Y. et al., "Structure–activity relations of antitumor hexamethylmelamine derivatives" Chem. Abstracts, 1984, 100: 61386k.

Acs, et al., *Proc. Natl. Acad. Sci. USA 84*: 4641–4644 (1987).

Axtell, et al., *Poultry Science* 62:2341–2377 (1984).

Kreutzberger et al., *Arzneim–Forsch./Drug Res. 36*, Nr. 4, pp. 626–629 (with English language abstract), 1986.

MacIntire, G. et al., *American Society for Microbiology*, 35, 12:2630–2633 (1991).

Menninger, J. R., et al., *Molecular and General Genetics*, 243:225–233 (1994).

Sells, M.A.., et al., *Journal of Virology*, 62, 8: 21836 (1986).

Thigpen, J. T., et al., *Cancer Supplement* 71: 1559–1564 (1993).

Thompson, et al., *Molecular and General Genetics*, 201: 168–173 (1985).

* cited by examiner

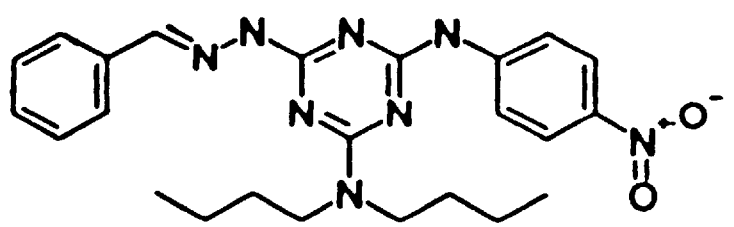
FIG. 1
FIG. 2
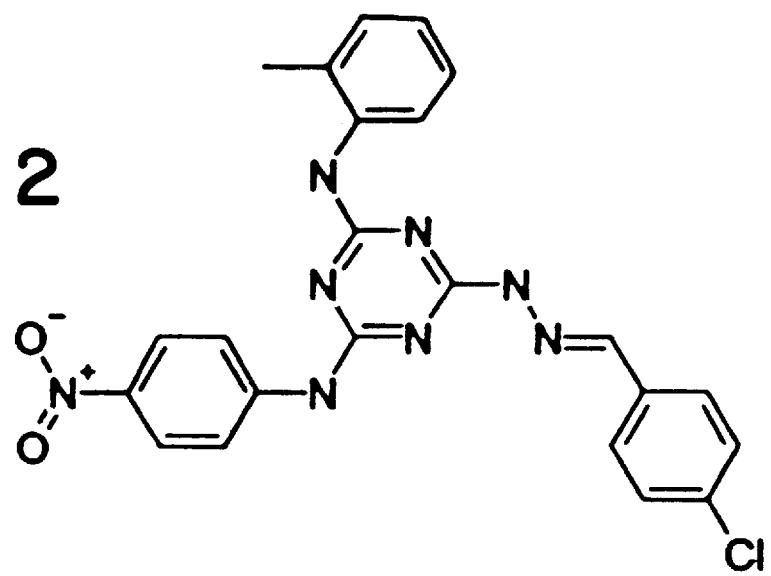
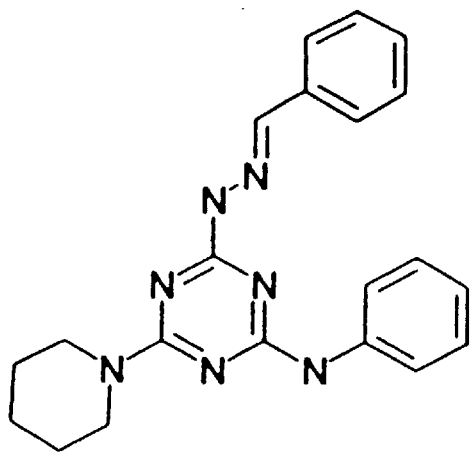
FIG. 3

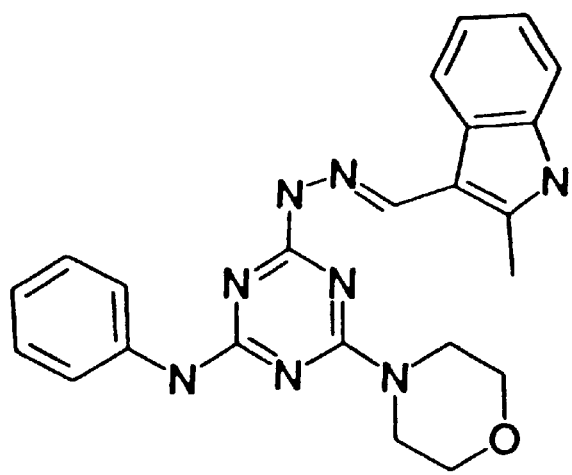
FIG. 4
FIG. 5
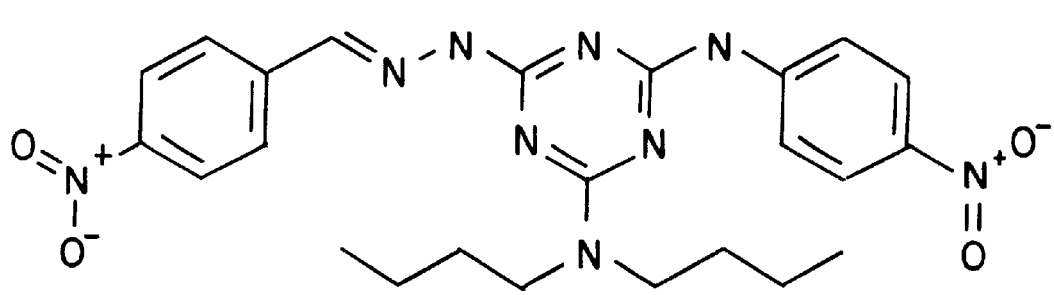
FIG. 6
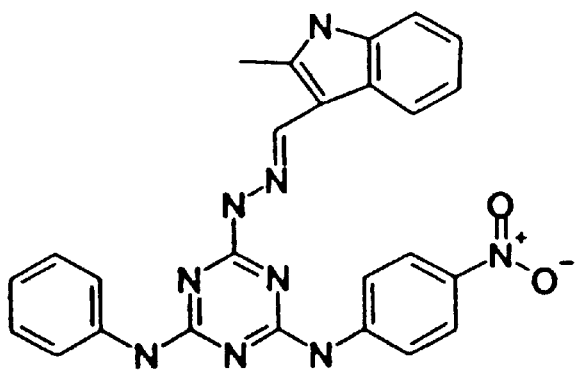

FIG. 13
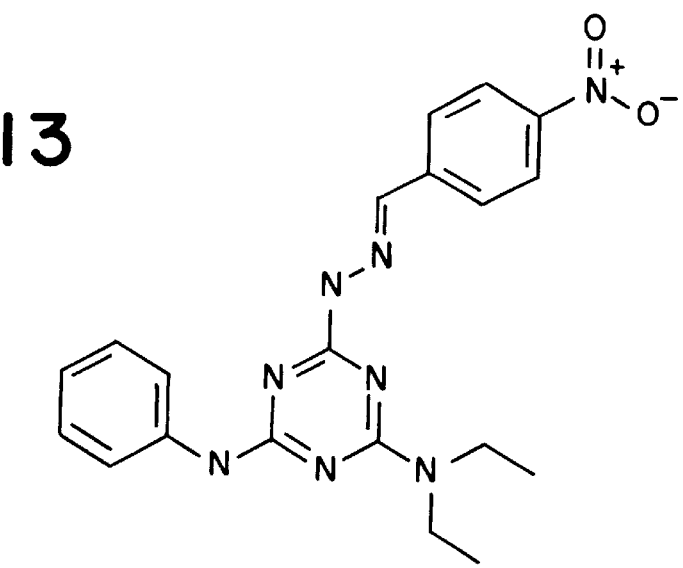
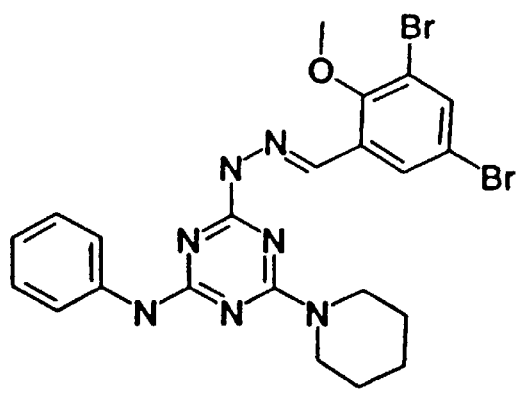
FIG. 14
FIG. 15
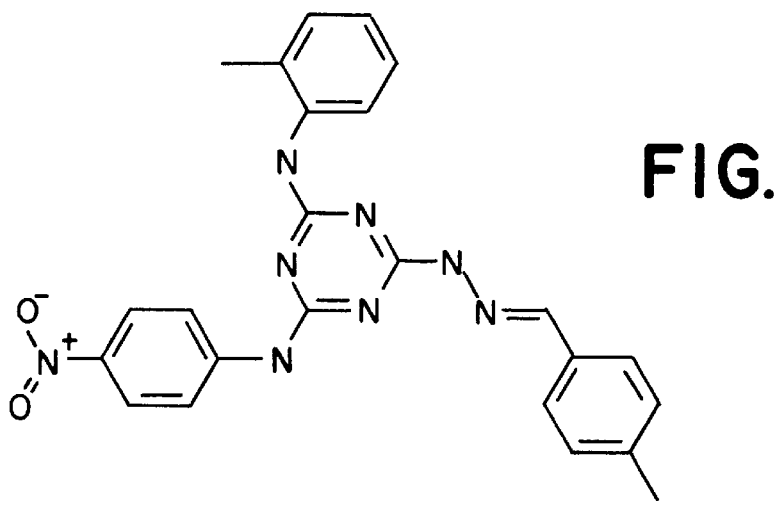

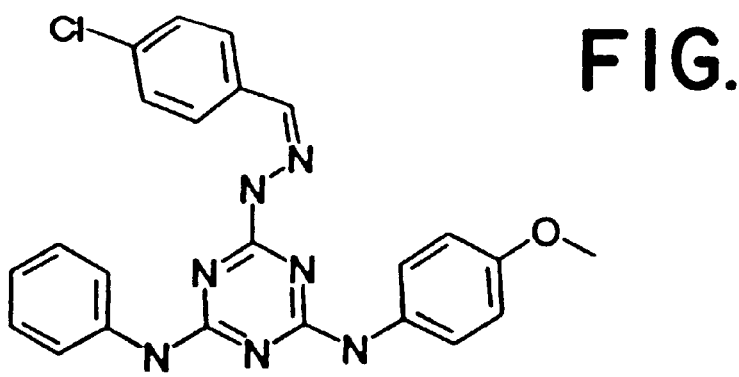
FIG. 22
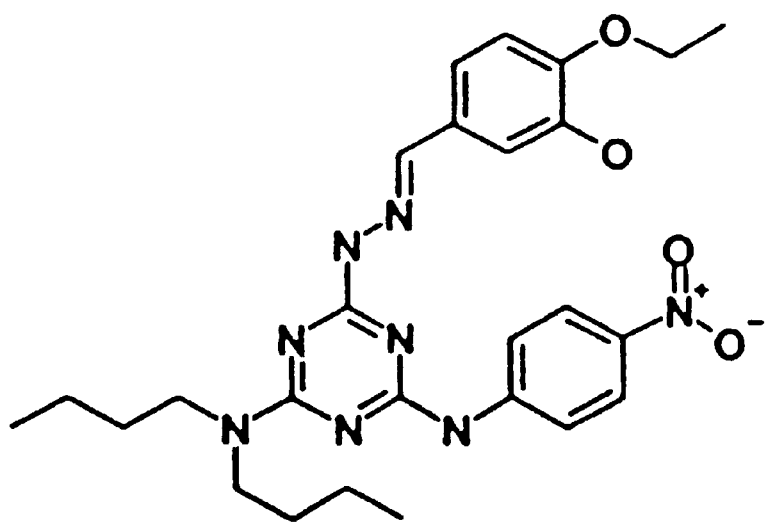
FIG. 23
FIG. 24
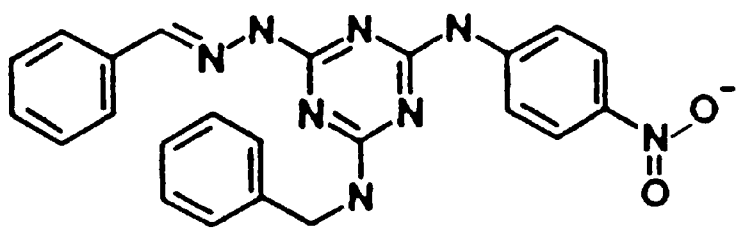

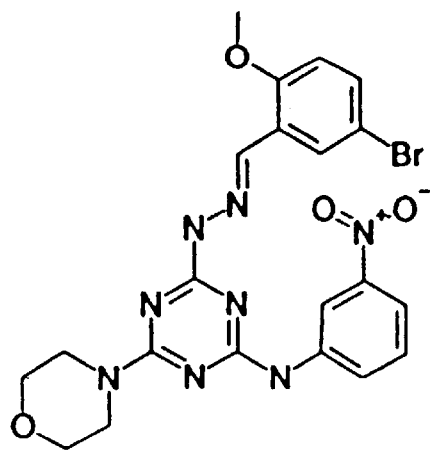
FIG. 28
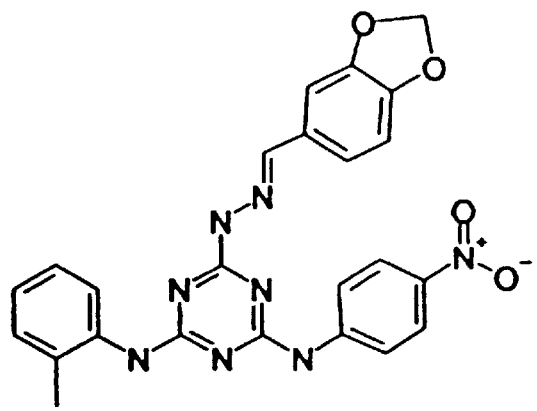
FIG. 29
FIG. 30
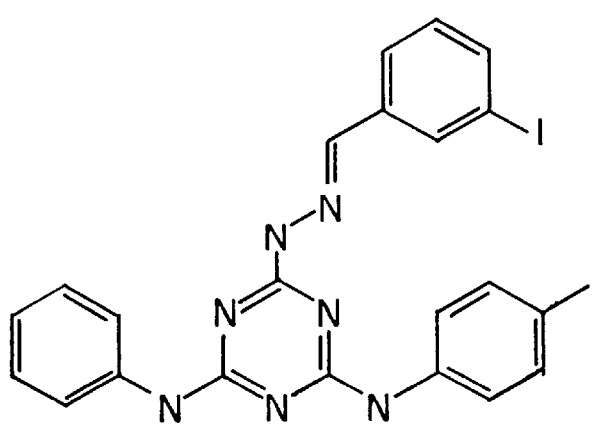

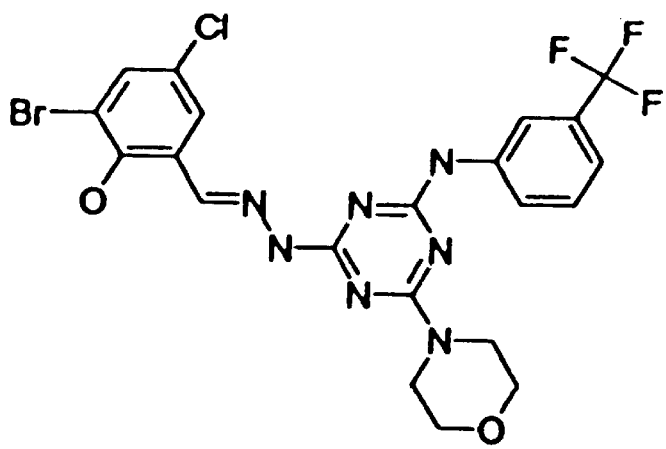
FIG. 34
FIG. 35
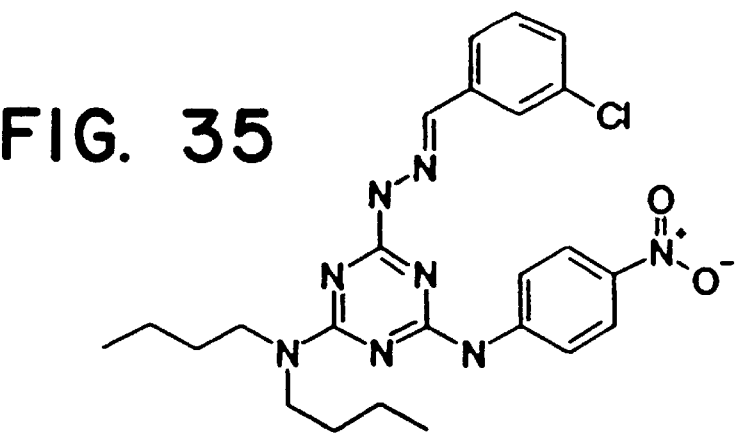
FIG. 36
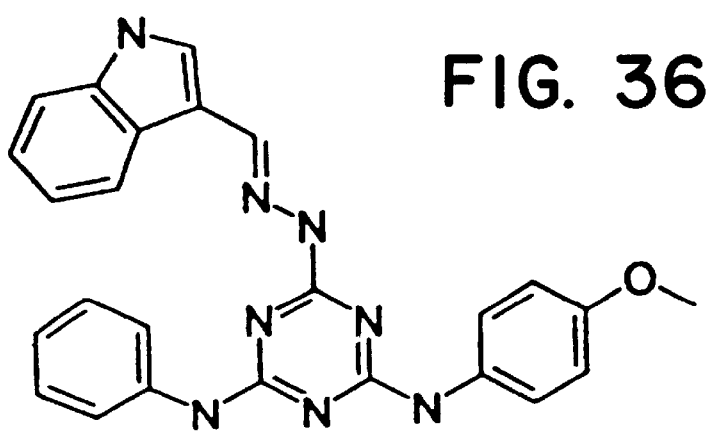

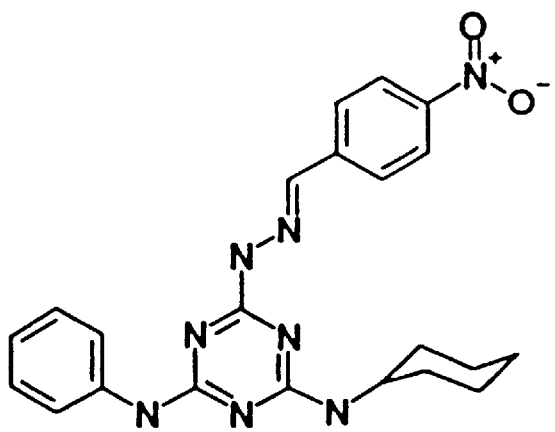
FIG. 46
FIG. 47
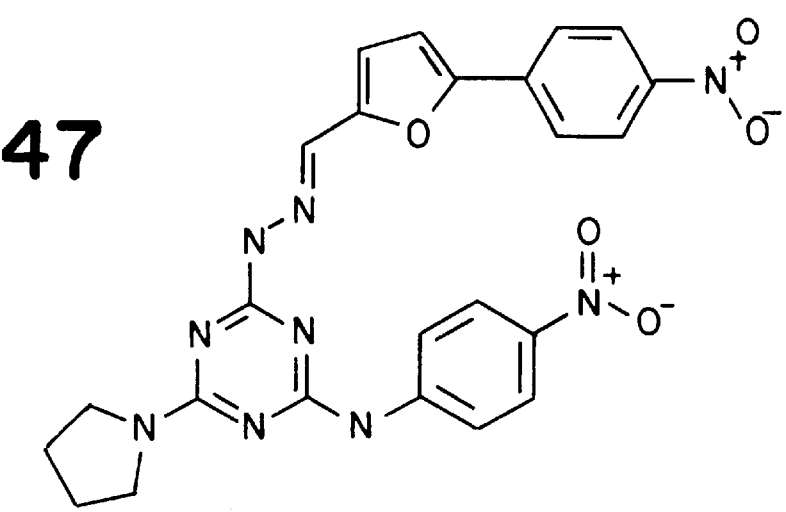
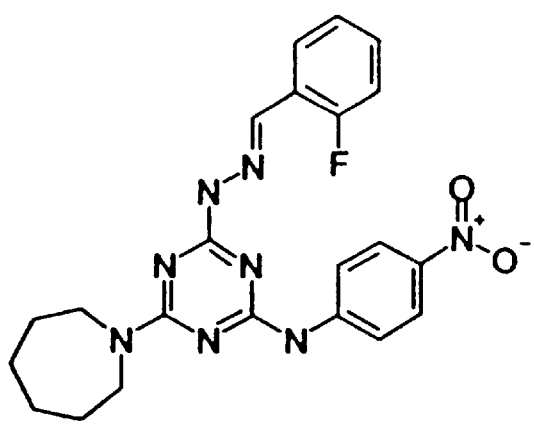
FIG. 48

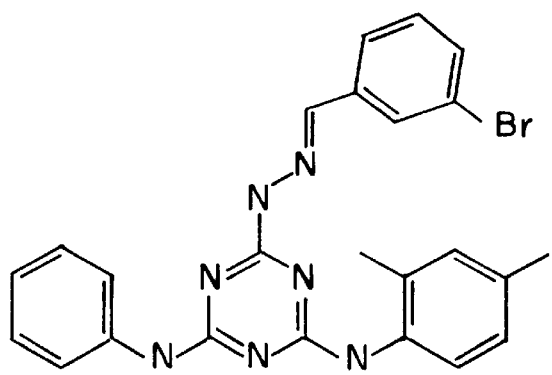
FIG. 49
FIG. 50
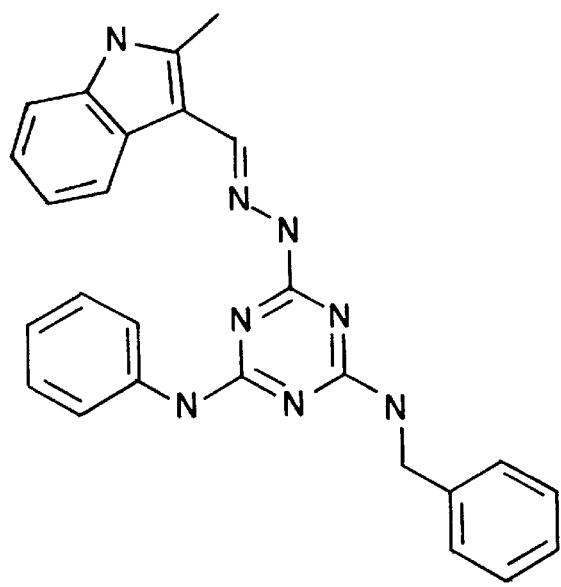
FIG. 51
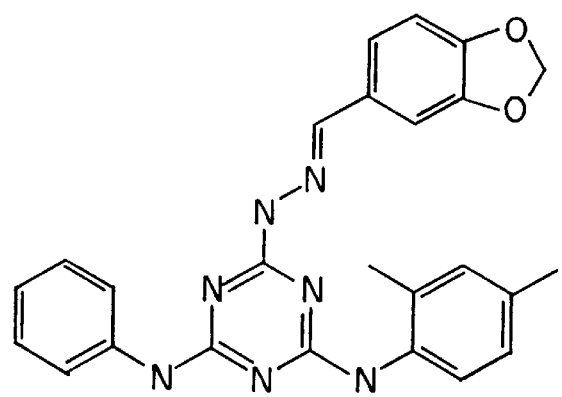

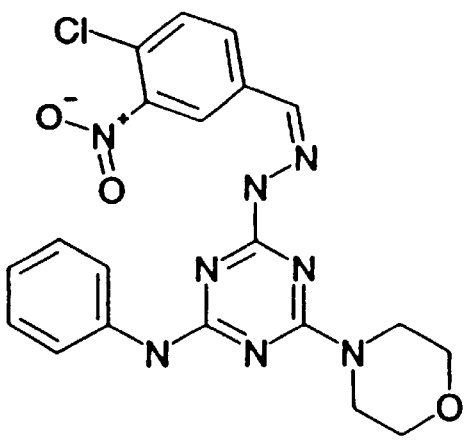
FIG. 52
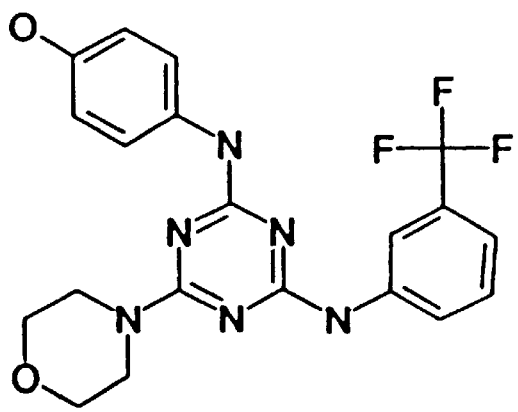
FIG. 53
FIG. 54
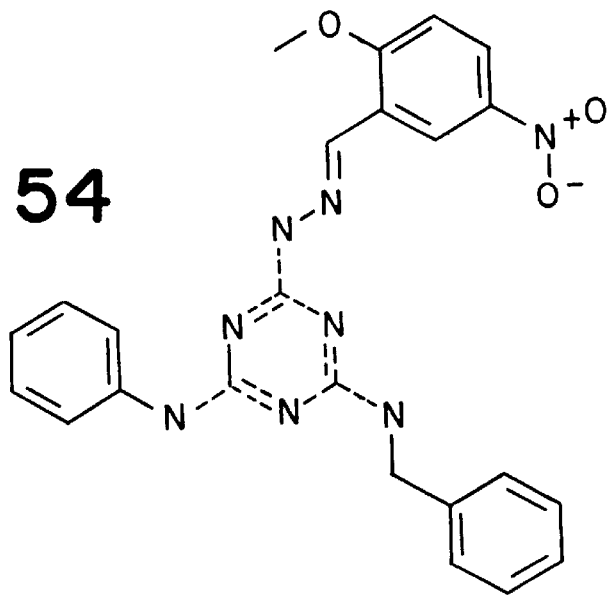

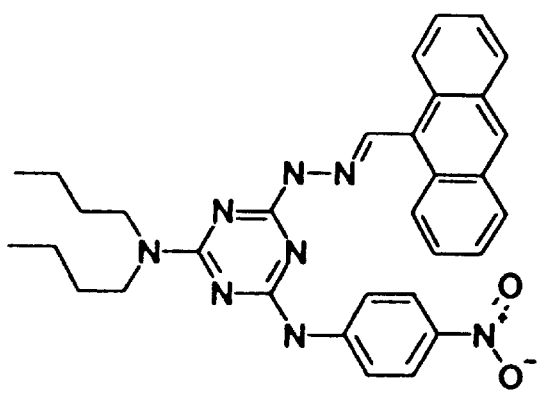
FIG. 55
FIG. 56
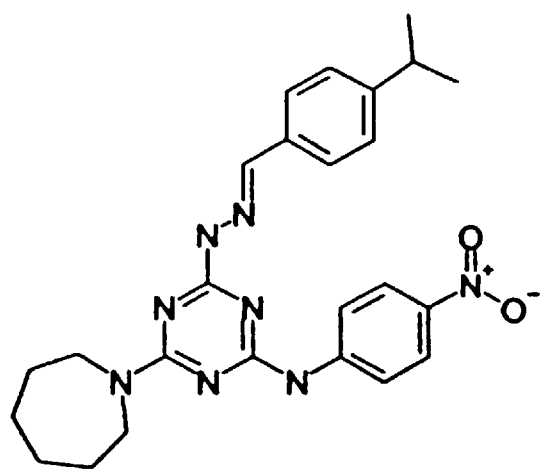
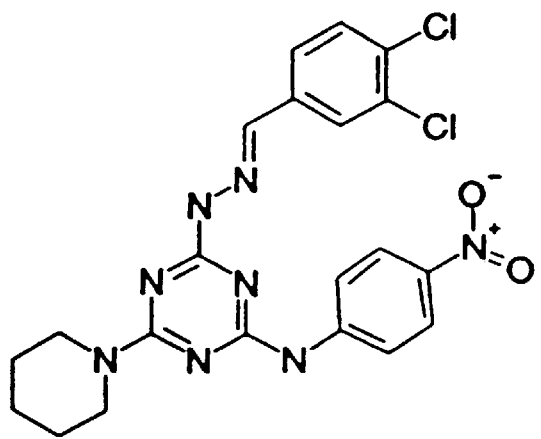
FIG. 57

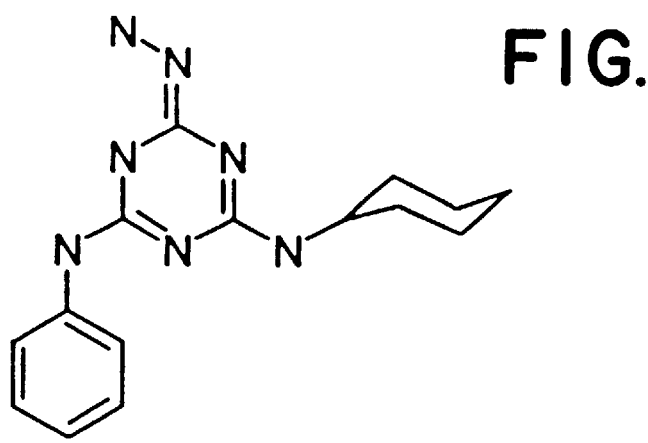
FIG. 58
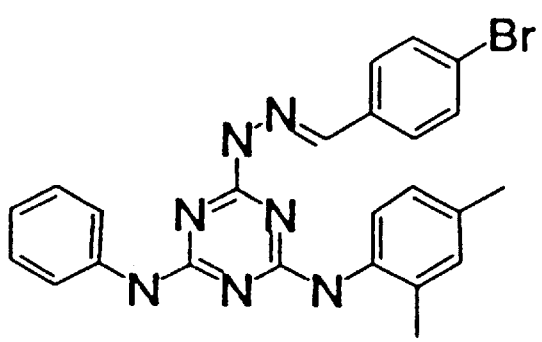
FIG. 59
FIG. 60
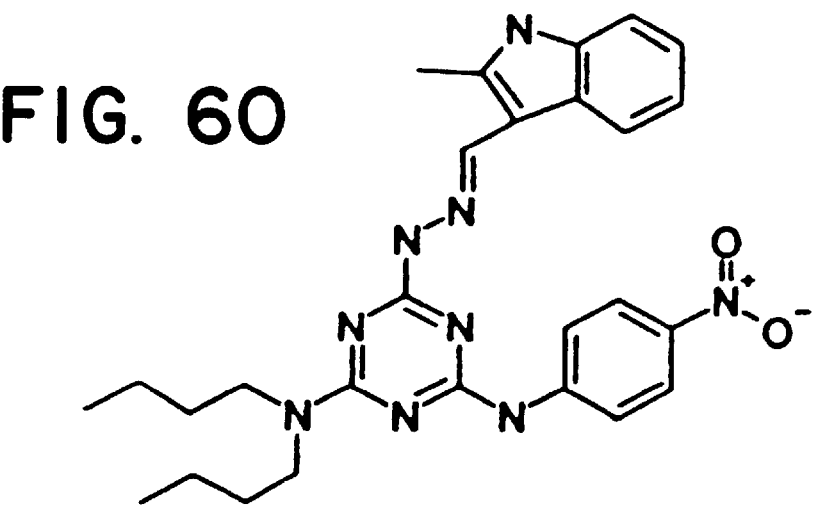

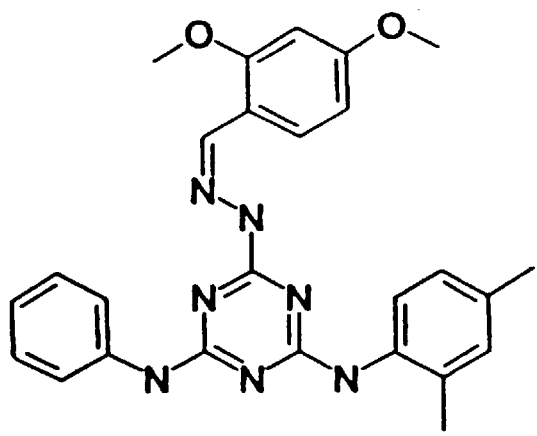
FIG. 61
FIG. 62
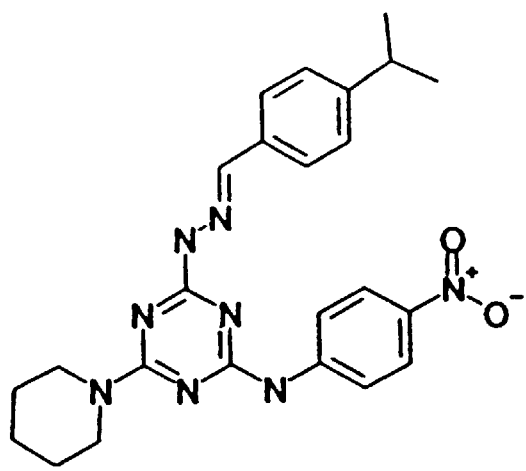
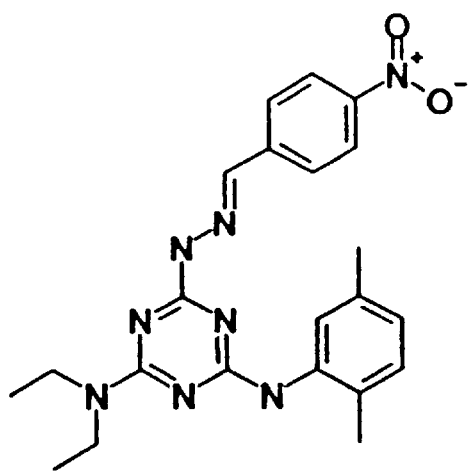
FIG. 63

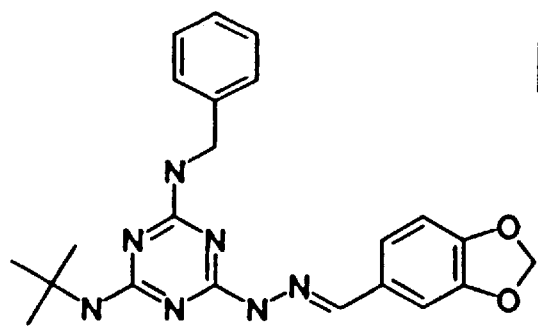
FIG. 67
FIG. 68
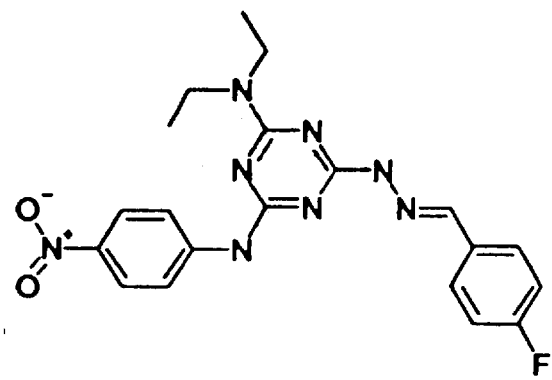
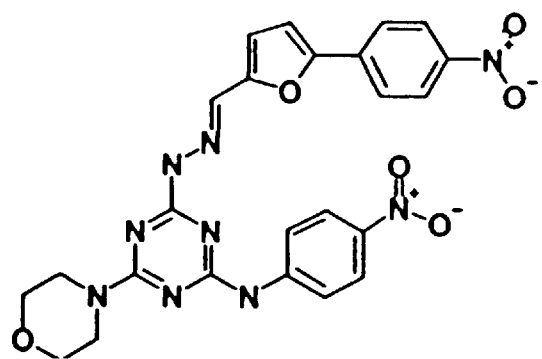
FIG. 69

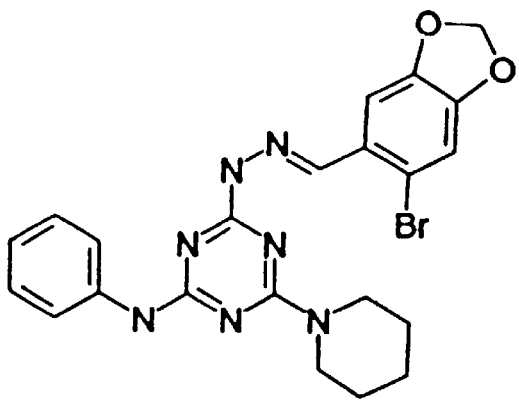
FIG. 70
FIG. 71
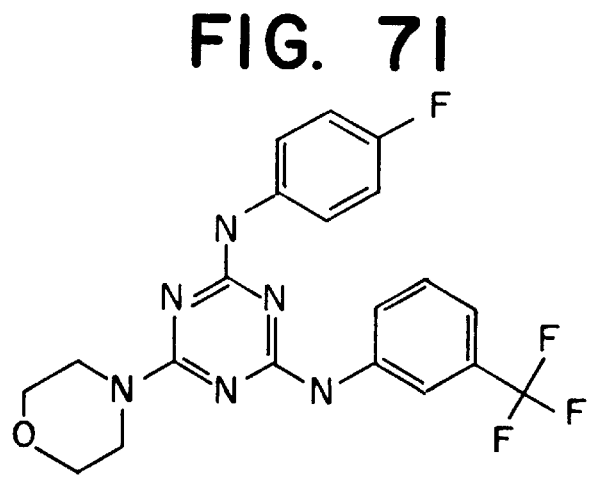
FIG. 72
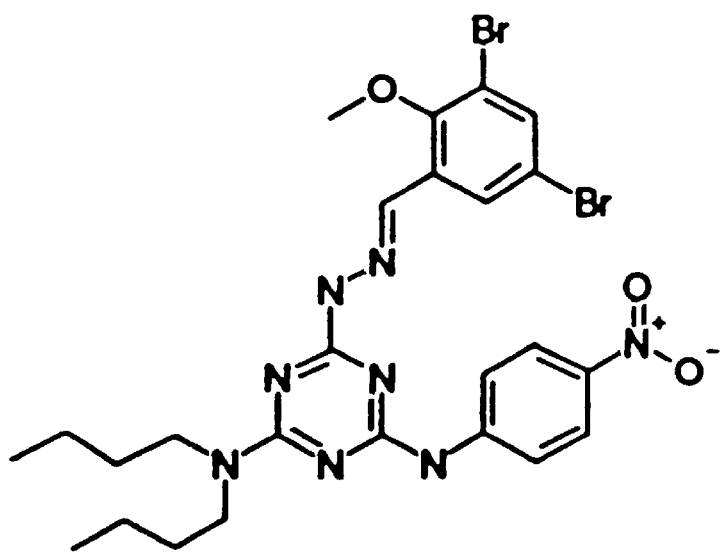

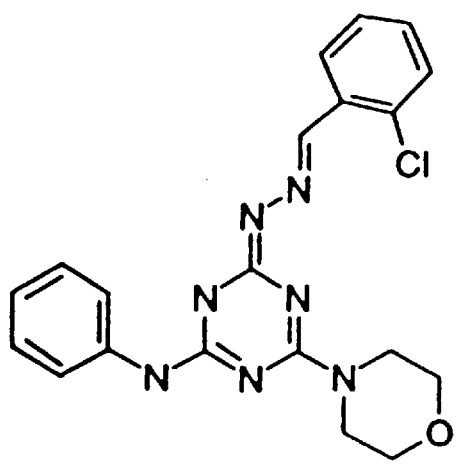
FIG. 73
FIG. 74
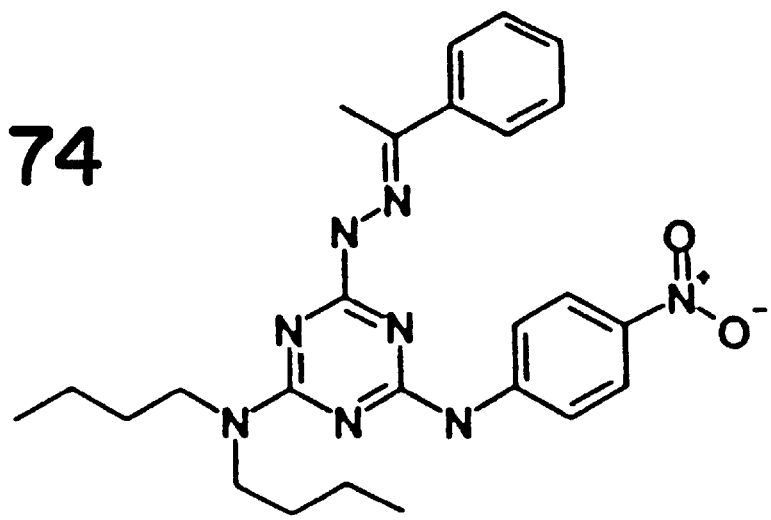
FIG. 75
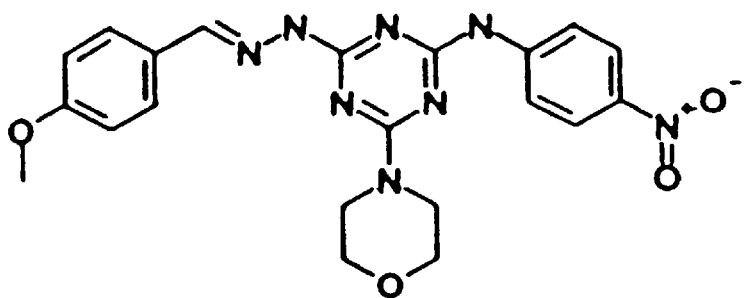

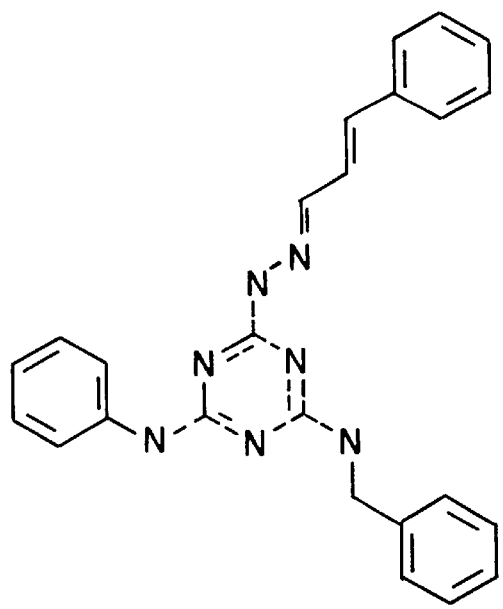
FIG. 91

FIG. 93
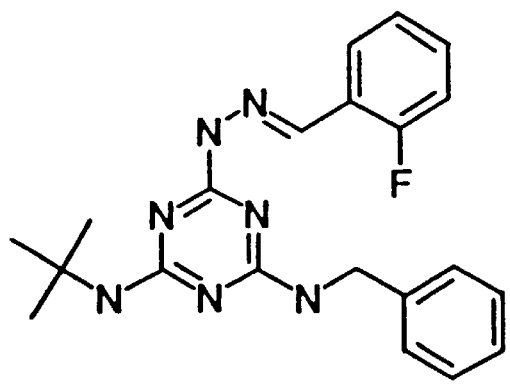

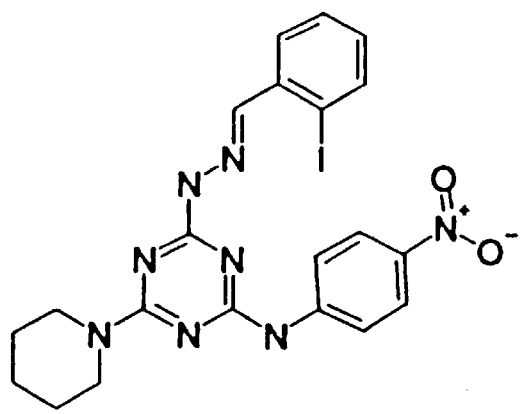
FIG. 124
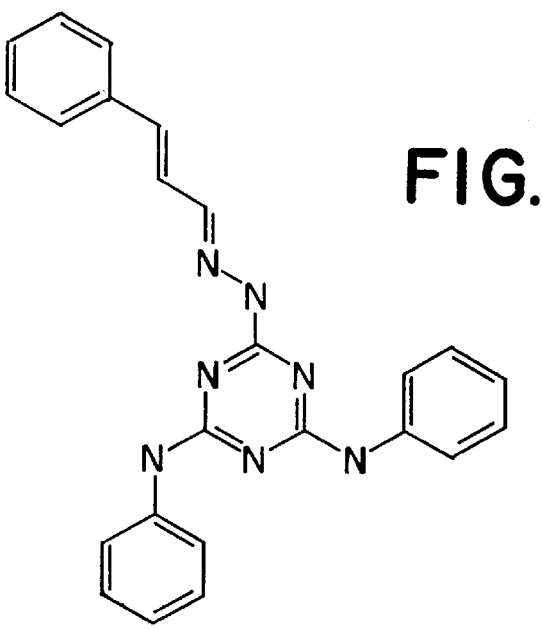
FIG. 125
FIG. 126
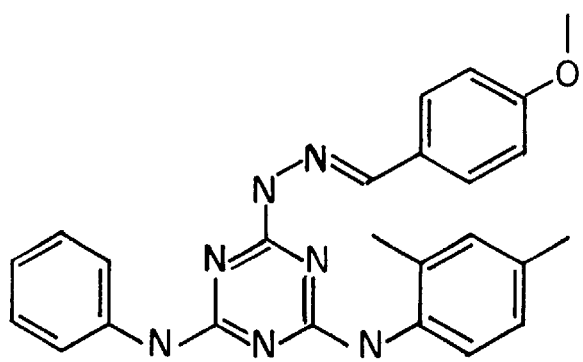

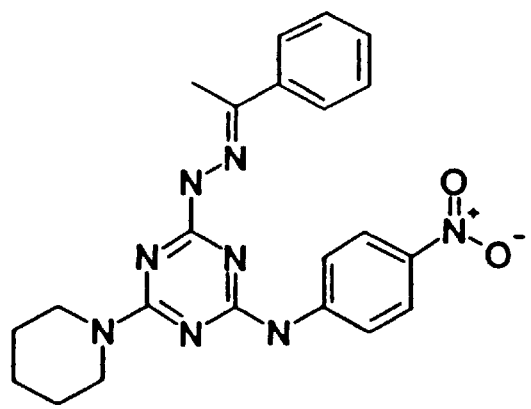
FIG. 151
FIG. 152
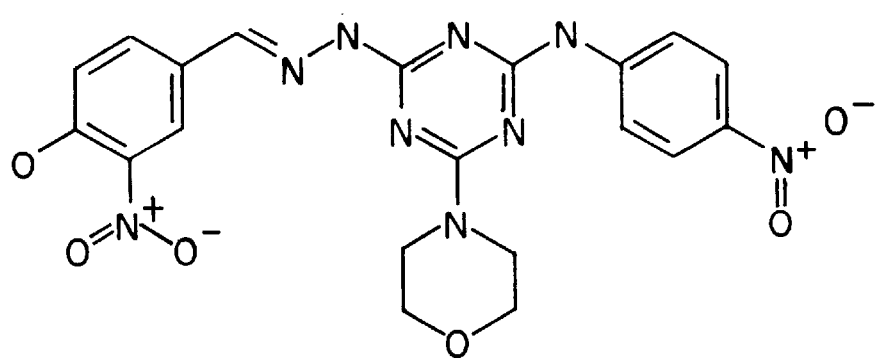
FIG. 153
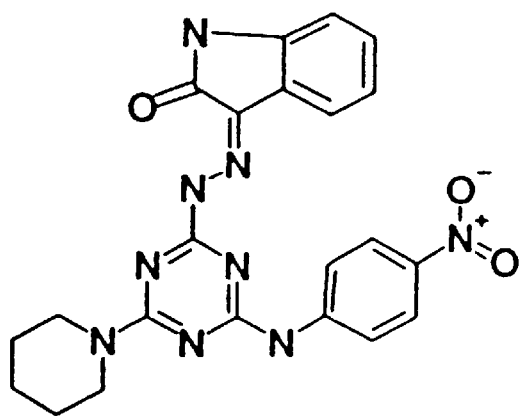

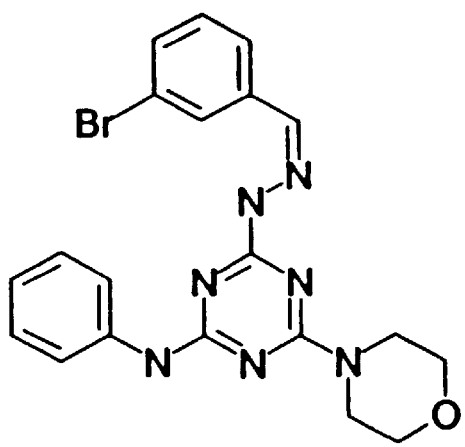
FIG. 163
FIG. 164
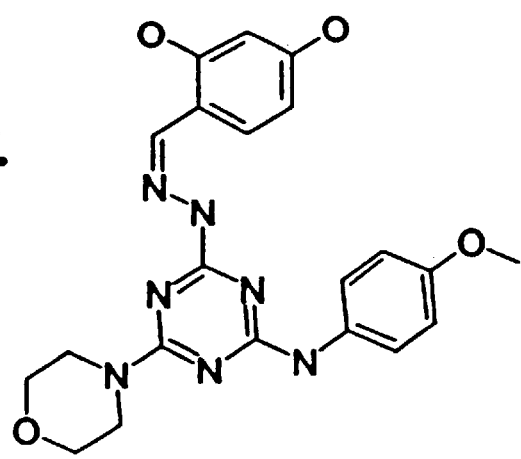
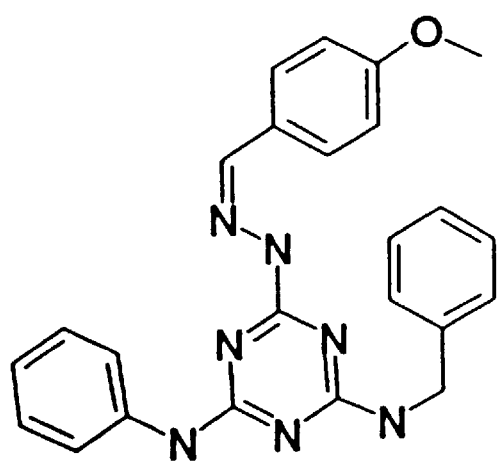
FIG. 165

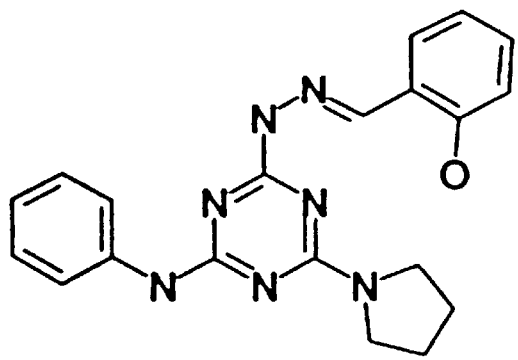
FIG. 209
FIG. 210
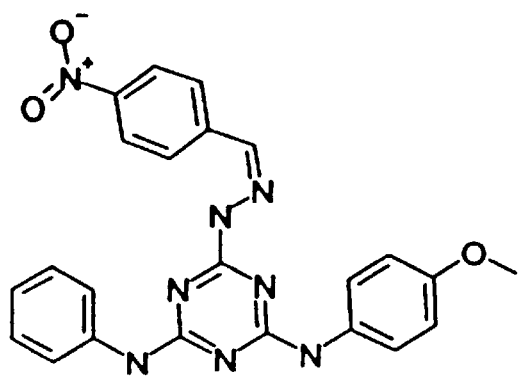
FIG. 211
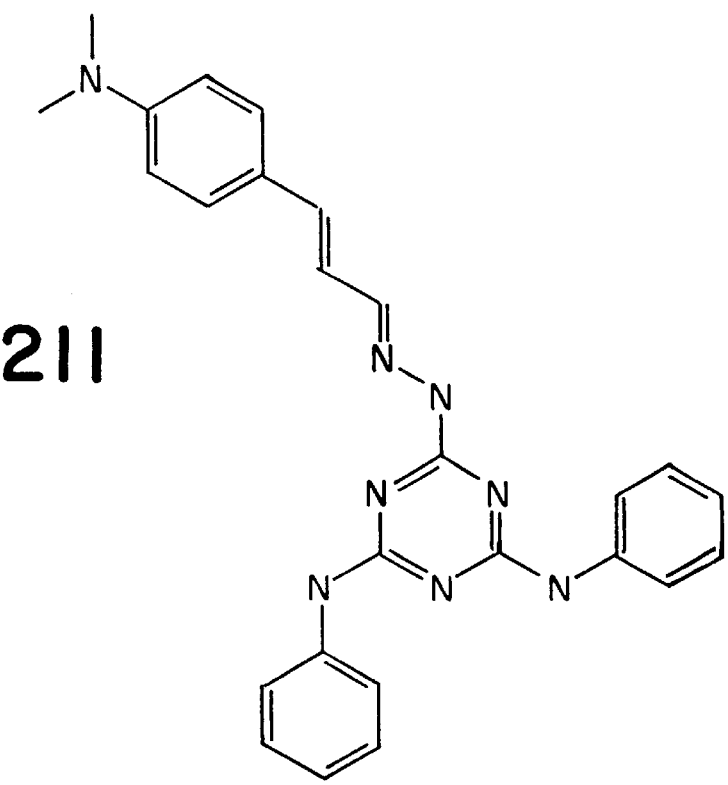

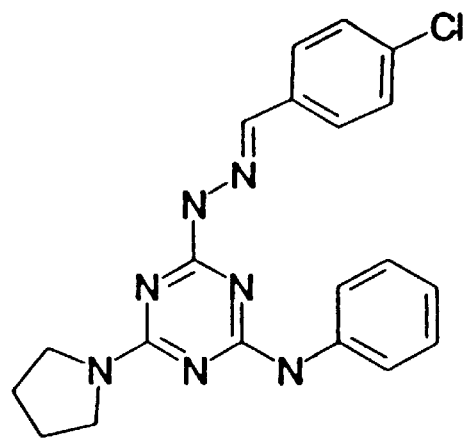
FIG. 218
FIG. 219
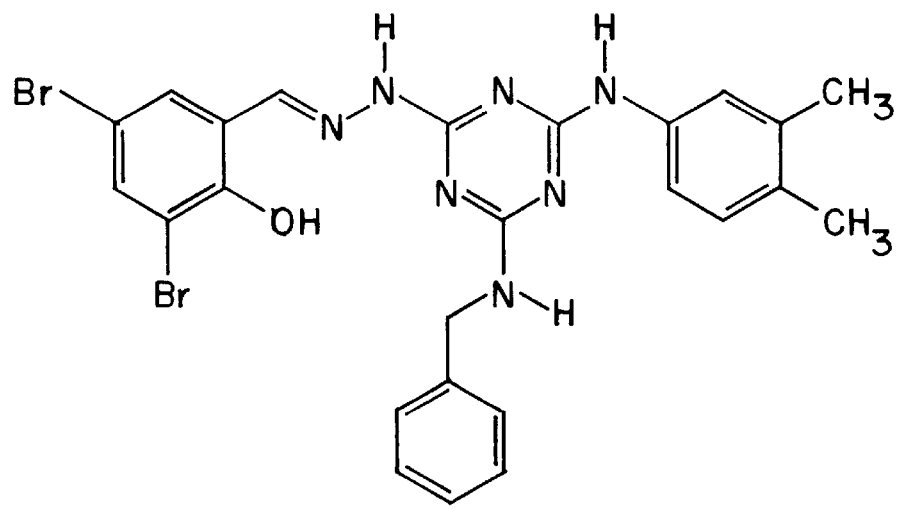
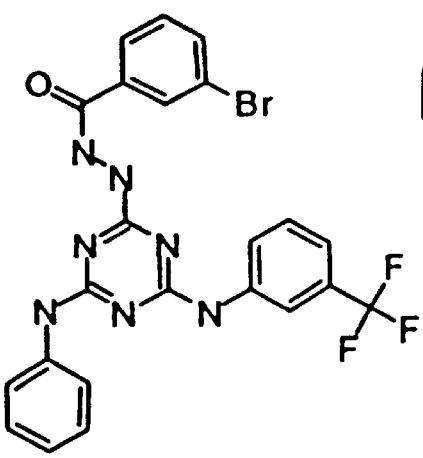
FIG. 220

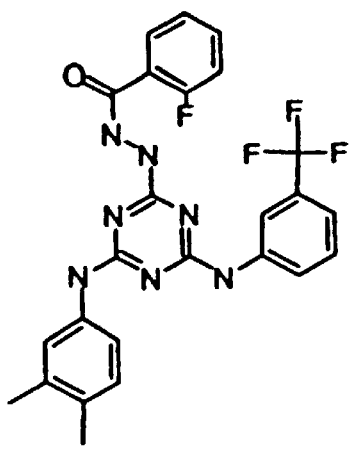
FIG. 236
FIG. 237
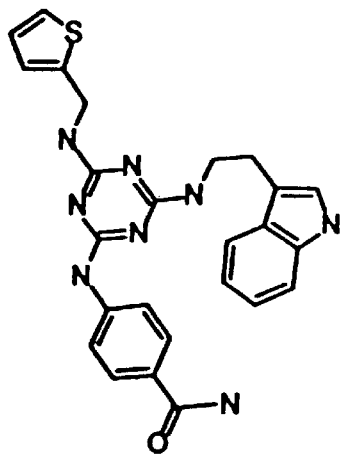
FIG. 238
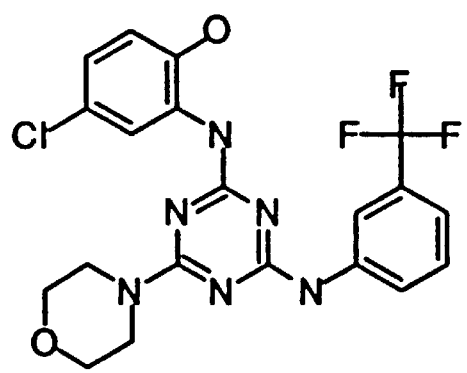

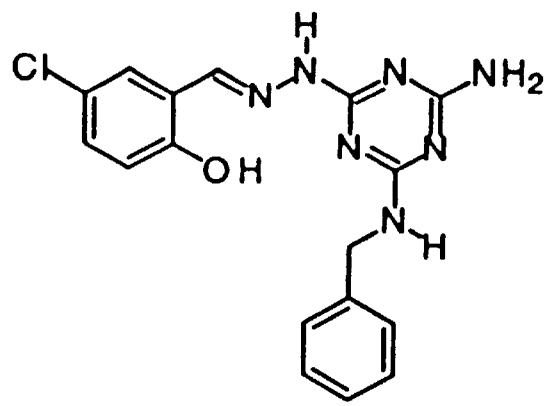
FIG. 242
FIG. 243
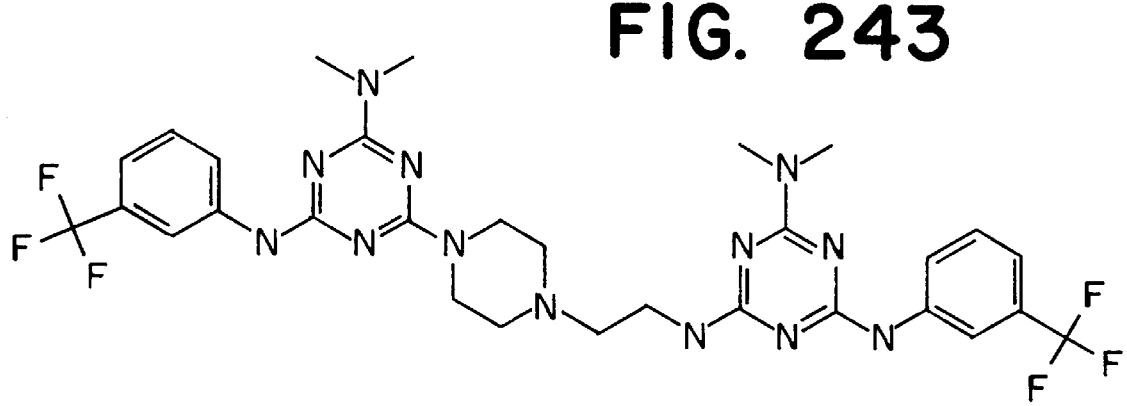
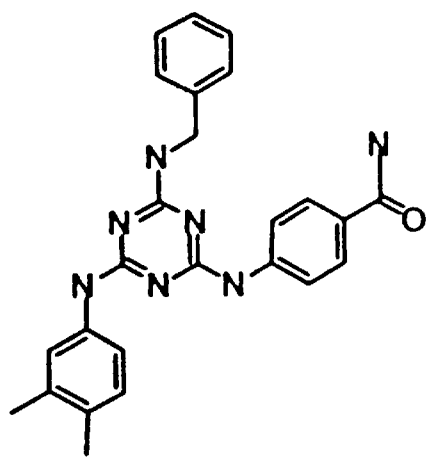
FIG. 244

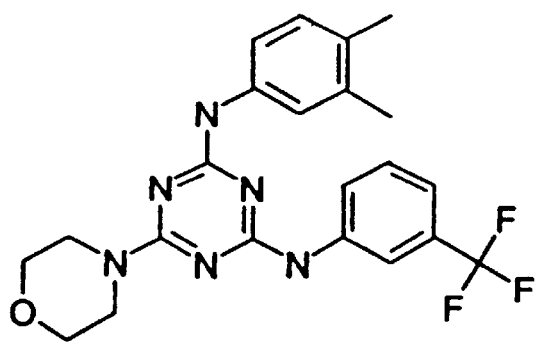
FIG. 251
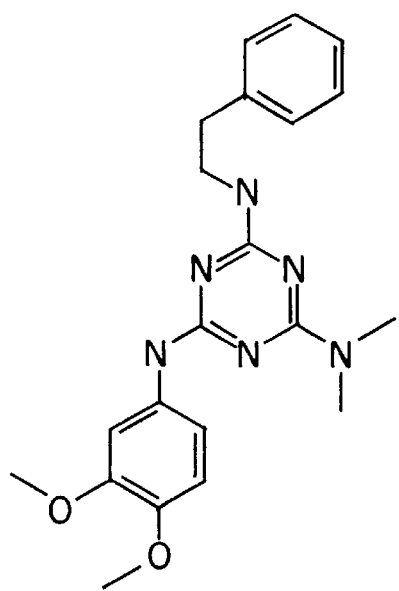
FIG. 252
FIG. 253
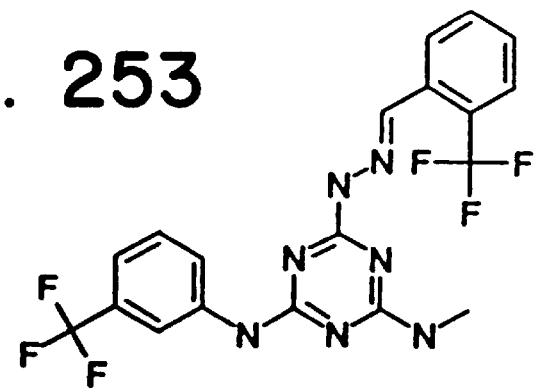

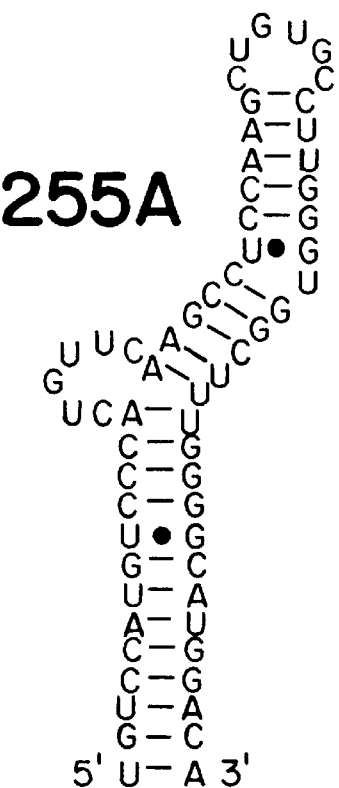
FIG. 255A
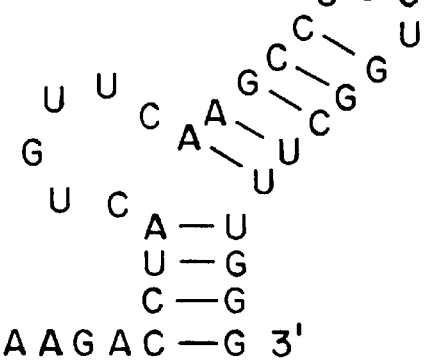
FIG. 255B
FIG. 255C
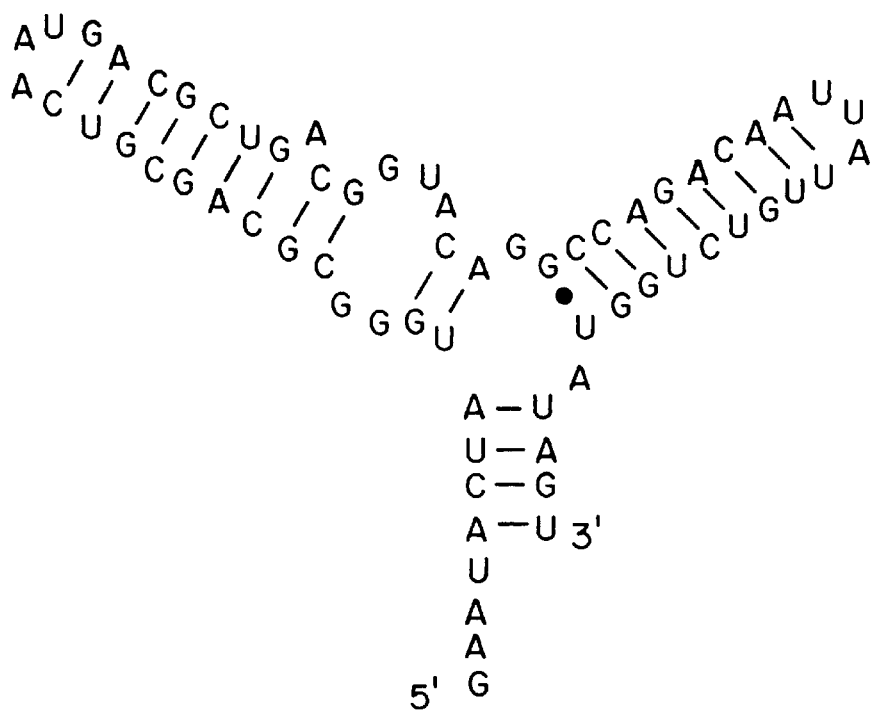

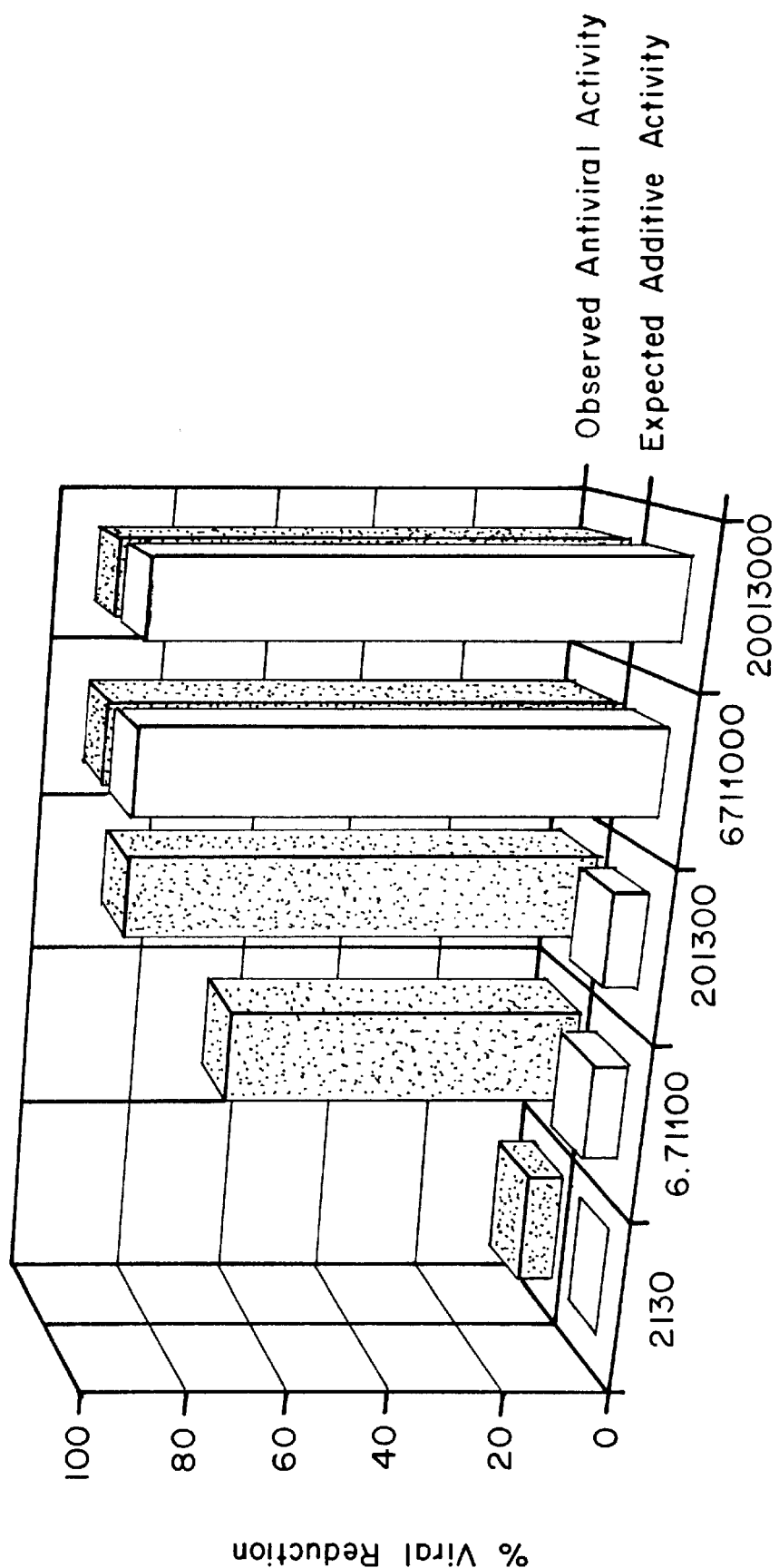

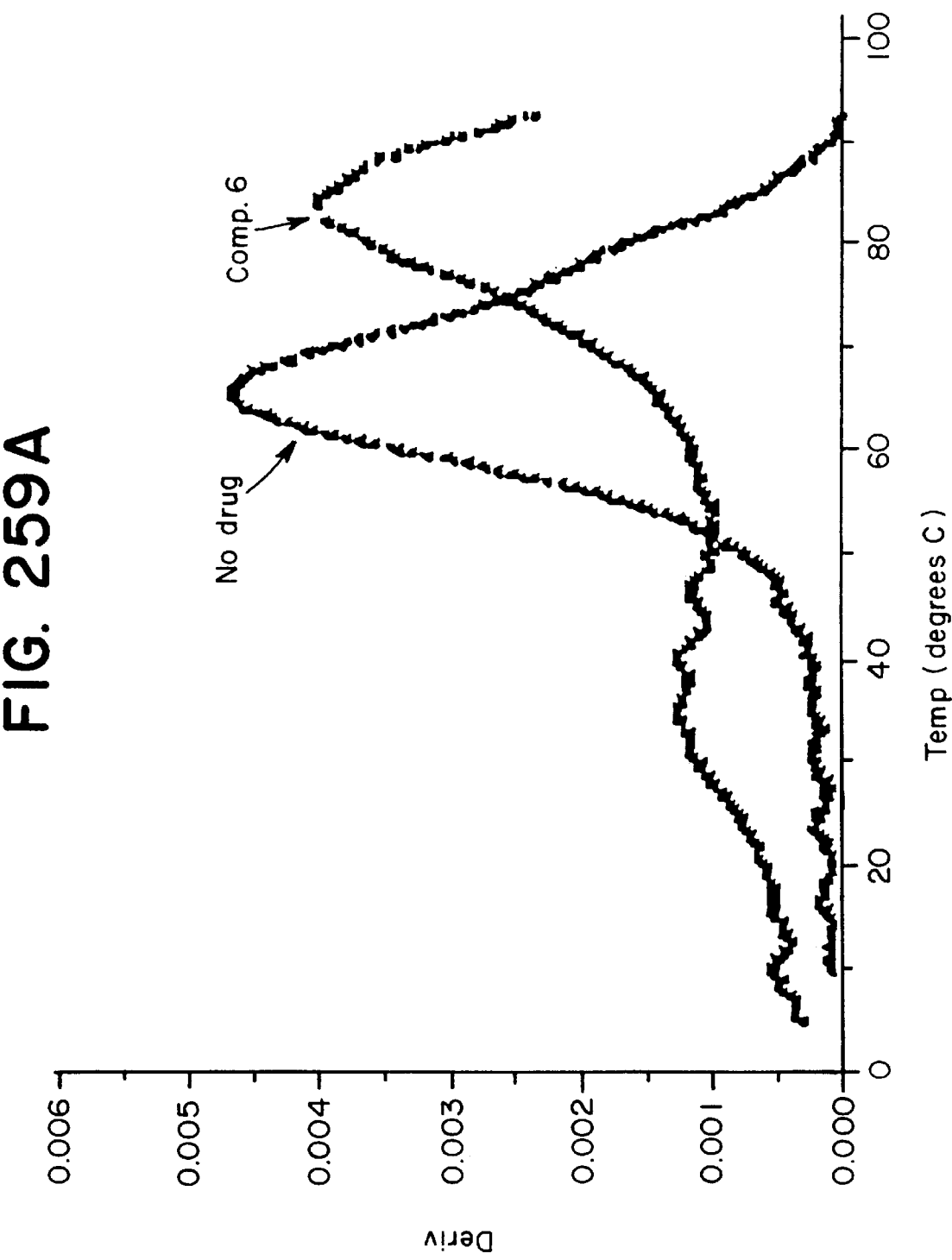

TRIAZINE ANTIVIRAL COMPOUNDS

This application claims priority under 35 U.S.C. §119(e) of U.S. Provisional Application Ser. No. 60/113,656, filed Jan. 13, 1998, which is hereby incorporated by reference.

FIELD OF THE INVENTION

This invention pertains to the interaction between nucleic acids and 1,3,5-triazine derivatives, their use as inhibitors of the replication of the Hepatitis B virus (HBV), and their use in the treatment of viral hepatitis caused by HBV.

BACKGROUND OF THE INVENTION

There is a great medical need for novel therapeutic drugs to treat viral infections. Approximately 300,000 Americans become infected annually with hepatitis B virus (HBV). Currently available drugs for the treatment of HBV have limited efficacy and have not exhibited lasting effects, such that virus titres rapidly increase following the termination of drug treatment. In addition, some classes of drugs, such as nucleoside analogs that inhibit the viral polymerase, often become ineffective due to the rapid appearance of resistant viral strains. For these reasons, it has become apparent that combination therapies utilizing multiple drugs that function by different mechanisms are likely to be more successful in the treatment of viral infections.

Small molecules can bind RNA with high affinity and specificity and can block essential functions of the bound RNA. Examples of such molecules are antibiotics such as erythromycin and aminoglycosides. The first suggestion that some antibiotic translation inhibitors interact specifically with RNA came from the genetic mapping of resistance to kanamycin and gentamicin to the methylation of 16S RNA (Thompson et al., *Mol. Gen. Genet.* 201:168, 1985). Erythromycin binds to bacterial RNA and releases peptidyl-tRNA and mRNA (Menninger et al., *Mol. Gen. Genet.* 243:225, 1994). 2-DOS-containing aminoglycosides bind specifically to the structures of HIV RNA known as the RRE, block binding of the HIV Rev protein to this RNA, and thereby inhibit HIV replication in tissue culture cells (Zapp et al., *Cell* 74:969, 1993). In addition, although aminoglycosides have long been developed as translation inhibitors, they were only recently shown to bind to rRNA in the absence of proteins (Purohit and Stem, Nature 370:659, 1994). Hygromycin B inhibits coronaviral RNA synthesis and is thought to do so by binding to the viral RNA and blocking specifically the translation of viral RNA (Macintyre et al., *Antimicrob. Agents Chemother.* 35:2630, 1991). Therefore, compounds that bind to functionally important regions of nucleic acids of viruses and microorganisms may be useful as inhibitors of replication or other functions, i.e., as antiviral agents and antibiotics.

The present invention pertains specifically to a novel class of drugs comprising RNA ligands that alter the function(s) of their target RNAs. This class of compounds comprises substituted 1,3,5-triazine derivatives that specifically recognize an essential and multifunctional RNA structure of the HBV pregenomic RNA known as the encapsidation signal (εRNA). It has been unexpectedly found that this class of compounds can function as inhibitors of HBV replication. εRNA, shown in FIG. 255A, consists of a short sequence that folds into a stem-loop structure interrupted by a 6 nucleotide bulge. εRNA, which is contained within the open reading frame encoding the HBV precore protein, is also required for various steps of the HBV viral replication cycle, including encapsidation of the pregenome into viral particles and initiation of minus strand DNA synthesis. εRNA may also play a role in folding and activation of the HBV-encoded polymerase.

Derivatives of melamine, 1,3,5-triazine-2,4,6-triamine, have been reported in the literature as suitable for various uses. For example, 2,4,6-tris(dimethylamino)-1,3,5-triazine is an antitumor agent known as Altretamine®, used in the treatment of ovarian cancer (*Cancer* 71; 4 Suppl.: 1559, 1993). Similarly, Larvadex (N-cyclopropyl-1,3,5-triazine-2, 4,6-triamine) has been used as an additive to animal feed stock to control house fly infestation in poultry houses (*Poult. Sci.* 62(12): 2371, 1983).

Further, Patel et al. (*J. Inst. Chemists* (India), 57, 1985) report a number of derivatives of 2-aryl amino-4-(4-methoxy anilino)-6-(4-chlorophenyl/phenyl hydrazido)-1,3, 5-triazine having anti-bacterial activity, without data in support of this conclusion and absent any suggestion that the compounds could be used as antiviral agents.

U.S. Pat. No. 5,225,405 to Paramelle et al. refers to 4,6-bis-allylamino-1,3,5-triazin-2-yl derivatives which reverse acquired resistance to anti-cancer and anti-malarial agents. Paramelle et al. state that the disclosed triazine derivatives, when administered at the same time with a cytotoxic agent, reduce or completely suppress multidrug resistance. The triazine compounds presumably act by inhibiting the action of an inducible membrane protein that normally functions to increase the efflux of the cytotoxic agent, thereby reducing its intracellular concentration. Paramelle et al. are silent as to the use of the triazine derivatives as antiviral agents.

U.S. Pat. No. 4,508,898 to Ogilvie relates to nucleoside analogs that have a 1,3,5-triazine moiety, wherein the analog compounds exhibited antiviral activity. The compounds of Ogilvie, however, do not comprise 2,4,6-triamino-1,3,5-triazine derivatives, but rather, are N-substituted purine and pyrimidine compounds.

European Patent Application No. 172 608 to Kim et al. relates to 1,3,5-triazine derivatives that exhibit anti-ulcer, anti-inflammatory and anti-depressant activities. However, Kim et al. fail to suggest that the disclosed triazine derivatives can be used as antiviral agents.

Golankiewicz, et al. (*J. Med. Chem.* 38: 3558, 1995) report the isolation of several 1,3,5-triazine derivatives having antiviral activity. However, the derivatives were limited to imidazo-[1,5-α]-1,3,5-triazine derivatives, with special emphasis on thio- and benzyl-substituted derivatives.

Kreutzberger et al. (*Arzneim.-Forsch./Drug. Res.* 36 (I) (4): 626, 1986) relates to aliphatically substituted chlorodihexylamino-1,3,5-triazines having antiviral activity. However, these compounds are structurally different from the compounds of the present invention.

WO 97/20825 discloses the isolation of various 1,3,5-triazine derivatives structurally distinct from those of the present invention. There is no suggestion that the triazine derivatives can be used as antiviral agents, but rather, that the compounds have utility as herbicides, insecticides, miticides, and bactericides.

U.S. Pat. No. 4,254,122 to Brown relates to 6-acylaminotetrahydro-1,3,5-triazine-2,4-dione derivatives that exhibit analgesic activities. The disclosed uses of the compound include their use as antiinflammatory agents and as inhibitors of prostaglandin synthetase.

Further, European Patent Application No. 795 549 to Gluzman et al. refers to bis-aryloxy(amino)-triazinyl-oxy (amino)aryl derivatives as antiviral agents. However, unlike the compounds of the present invention, the compounds of Gluzman et al. are dimers, linked by bicyclic or heterocyclic substituted moieties, and Gluzman et al. fails to suggest the use of the monomers as therapeutic compounds and/or compositions.

Thus, there is a need in the art for the identification of compounds that bind to functional viral nucleic acids, thereby inhibiting viral replication, and for specific antiviral agents that inhibit the replication of Hepatitis B virus. Such antiviral agents would be useful in the treatment of viral hepatitis caused by HBV.

SUMMARY OF THE INVENTION

The present invention provides methods for inhibiting viral and/or microbial replication, preventing or treating viral and/or microbial infection, and pharmaceutical formulations for use in such methods comprising a compound of the formulae IA

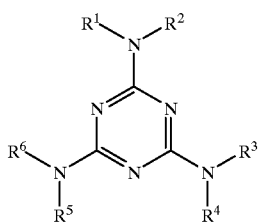

or IB

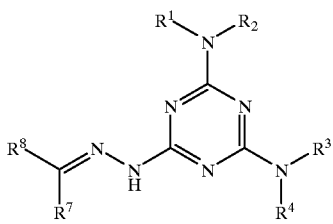

wherein $R^1$, $R^2$, $R^3$, $R^4$, $R^5$, $R^6$, $R^7$ and $R^8$ are each independently selected from the group consisting of hydrogen, alkyl, alkenyl, alkynyl, aryl, heteroaryl, non-aromatic heterocyclic, fused or polycyclic ring, and aryloxy;

wherein said alkyl, alkenyl or alkynyl is optionally substituted with one or more substituents selected from the group consisting of halogen, hydroxy, alkyl, nitro, trihalomethyl, aryl, aryloxy, alkoxy, amino, carbonyl, carboxyl, ester, amide, primary, secondary or tertiary amines, cyano, cycloalkyl, alkenyl, cycloalkenyl or alkenyl; and wherein said aryl, aryloxy, heteroaryl, non-aromatic heterocyclic, or fused or polycyclic ring is optionally substituted by one or more substituents selected from the group consisting of halogen, hydroxy, alkyl, nitro, trihalomethyl, aryl, aryloxy, alkoxy, amino, carbonyl, carboxyl, ester, amide, primary, secondary or tertiary amines, cyano, cycloalkyl, alkenyl, cycloalkenyl or alkynyl;

or wherein $R^1$ and $R^2$ together, $R^3$ and $R^4$ together, or $R^5$ and $R^6$ together, optionally form a cycloalkyl, cycloalkenyl, non-aromatic heterocyclic, heteroaryl, or fused or polycyclic ring, said cycloalkyl, cycloalkenyl, non-aromatic heterocyclic, heteroaryl, or fused or polycyclic ring optionally substituted with one or more substituents selected from the group consisting of halogen, hydroxy, alkyl, nitro, trihalomethyl, aryl, aryloxy, alkoxy, amino, carbonyl, carboxyl, ester, amide, primary, secondary or tertiary amines, cyano, cycloalkyl, alkenyl, cycloalkenyl and alkynyl;

or wherein $R^7$ and $R^8$ together optionally form a cycloalkyl, cycloalkenyl, non-aromatic heterocyclic, or fused or polycyclic ring wherein said cycloalkyl, cycloalkenyl, non-aromatic heterocyclic and fused or polycyclic ring are optionally substituted with one or more substituents selected from the group consisting of halogen, hydroxy, alkyl, nitro, trihalomethyl, aryl, aryloxy, alkoxy, amino, carbonyl, carboxyl, ester, amide, primary, secondary or tertiary amines, cyano, cycloalkyl, alkenyl, cycloalkenyl and alkynyl, with the proviso that when $R^7$ and $R^8$ together form a fused or polycyclic ring, the moiety of the fused or polycyclic ring that binds with N is non-aromatic;

and pharmaceutically acceptable salts thereof;

and a pharmaceutically acceptable carrier or diluent.

Further, it is an object of the present invention to provide antiviral and antibiotic formulations comprising one or more compounds represented by the formulae set forth above and pharmaceutically acceptable salts thereof, and a pharmaceutically acceptable carrier or diluent, and methods of administering such formulations to a patient in need of antiviral and/or antibacterial therapy. It is also an object of the present invention to provide a method of detecting a target nucleic acid by contacting the target nucleic acid with at least one compound of the formulae set forth above and pharmaceutically acceptable salts thereof, and monitoring an interaction between the target nucleic acid and the at least one compound of the formulae set forth above.

BRIEF DESCRIPTION OF THE DRAWINGS

FIGS. 1 to 254 are graphic illustrations of preferred 1,3,5-triazine compounds of the present invention.

FIG. 255A is a schematic illustration of the HBV pregenomic sequence that corresponds to the encapsidation signal (εRNA).

FIGS. 255B and 255C are a schematic illustrations of the target RNAs used in the method of the present invention.

FIGS. 257A, 257B and 257C are graphical illustrations of the percentage viral reduction when compounds 5 and antiviral drug 2'-deoxy-3'-thiacytidine were tested in combination, with molar ratios of 1:15, 1:5, and 1:1.5, respectively.

FIGS. 259A and 259B are graphical and schematic illustrations, respectively, of the change in the melting temperature (tm) of εRNA in the presence and absence of compound 6.

DETAILED DESCRIPTION OF THE INVENTION

Figure 7:
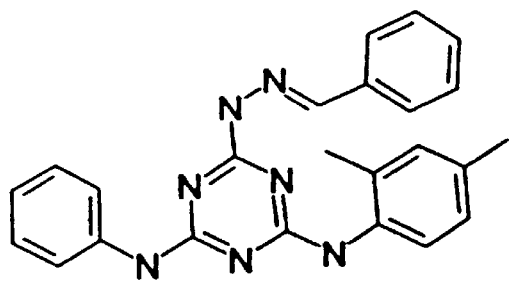
Figure 8:
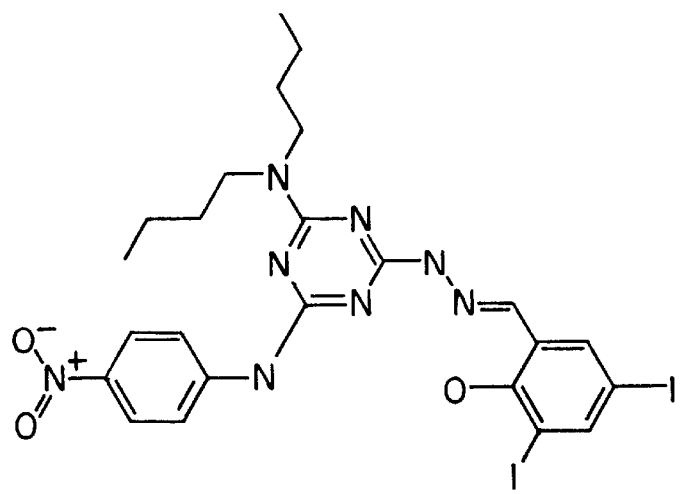
Figure 9:
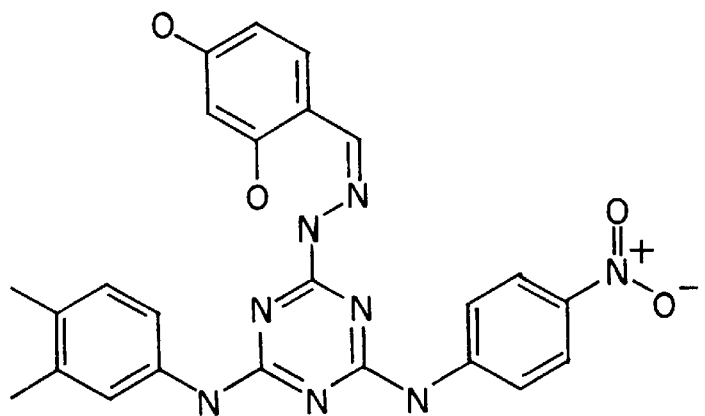
Figure 10:
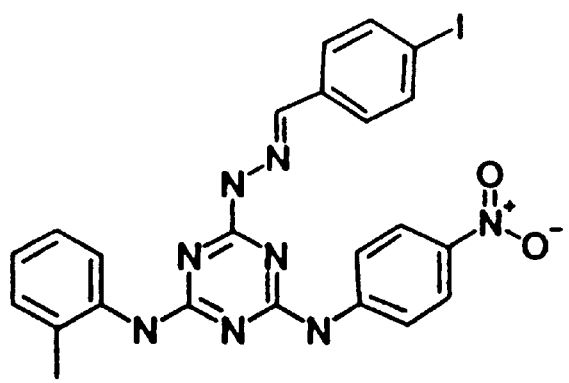
Figure 11:
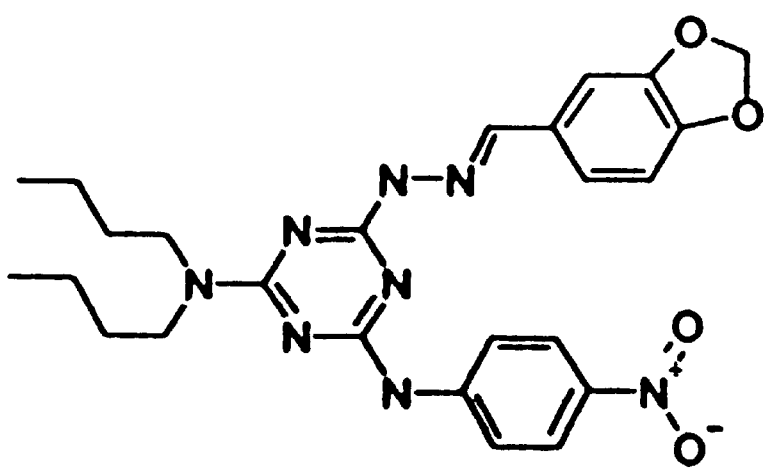
Figure 12:
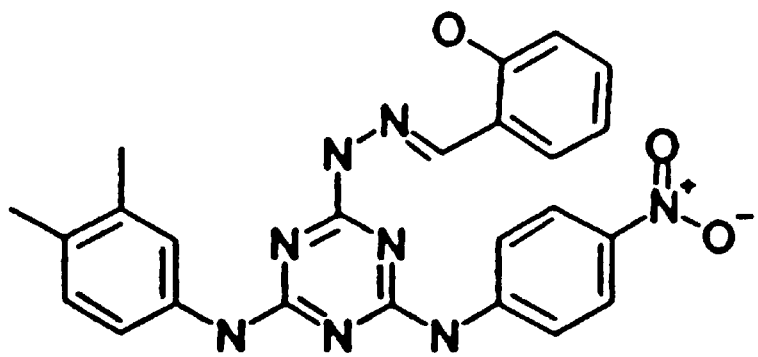
Figure 16:
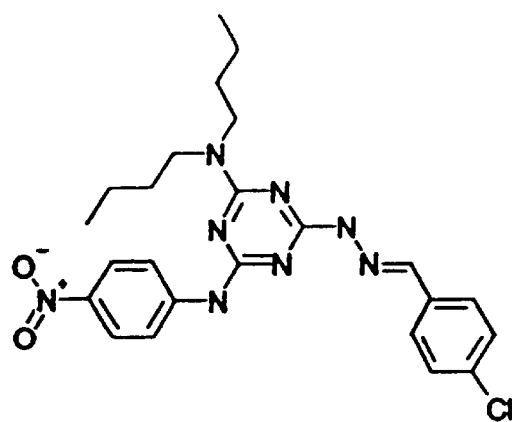
Figure 17:
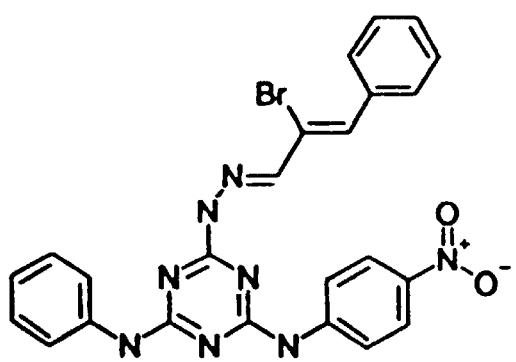
Figure 18:
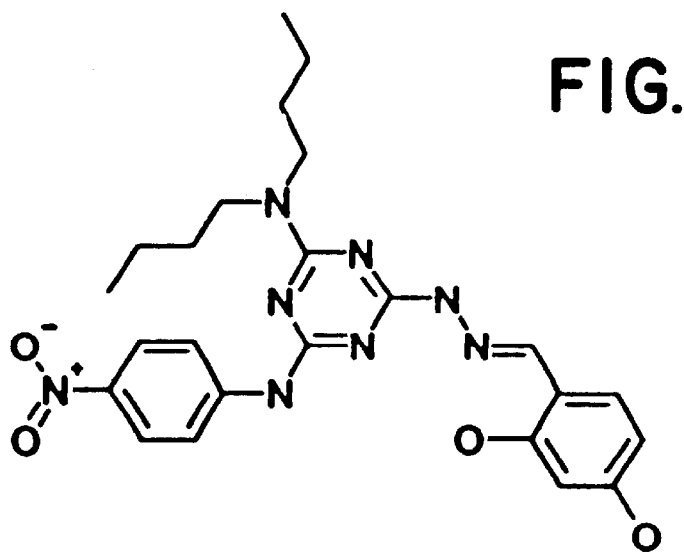
Figure 19:
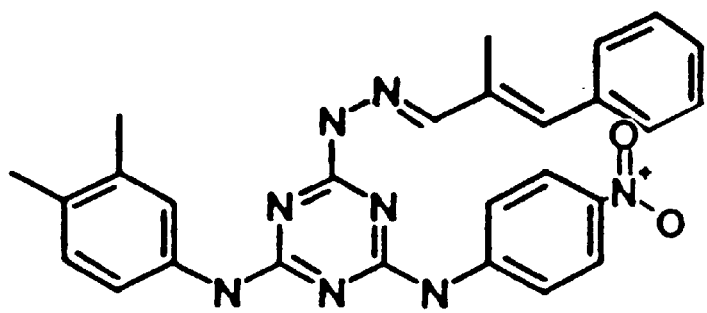
Figure 20:
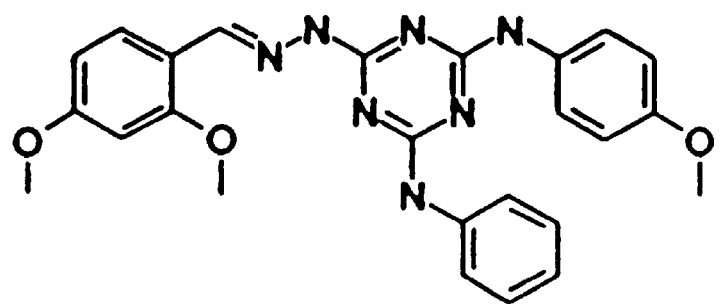
Figure 21:
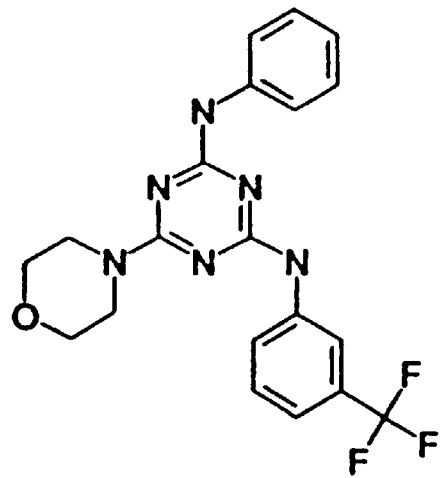
Figure 25:
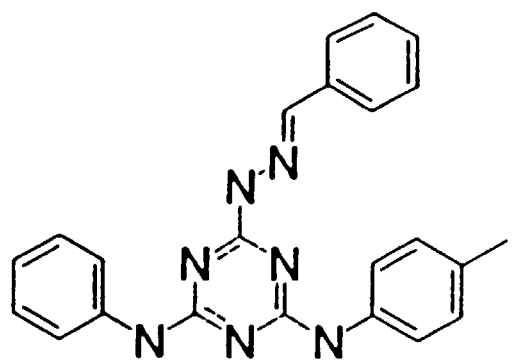
Figure 26:
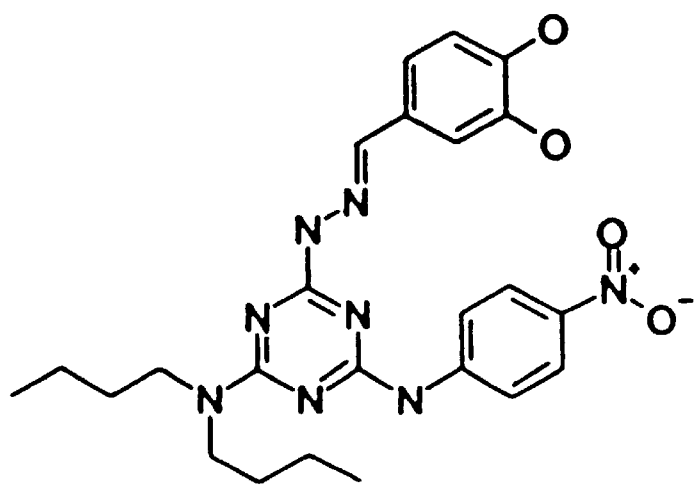
Figure 27:
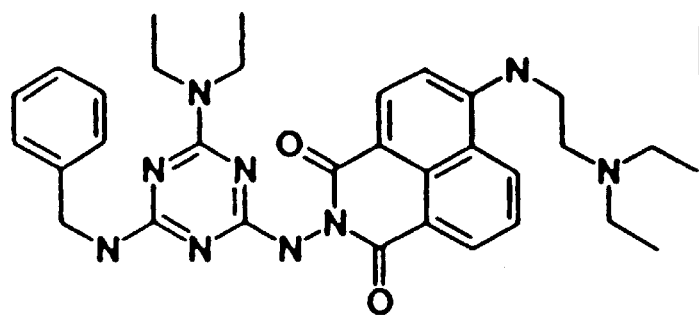
Figure 31:
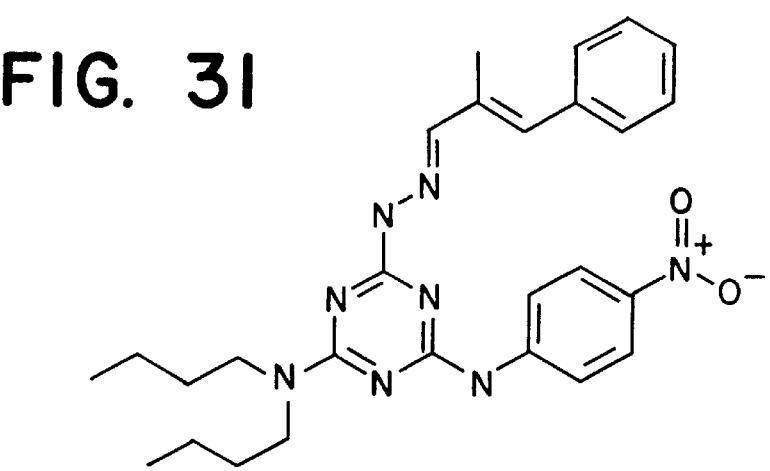
Figure 32:
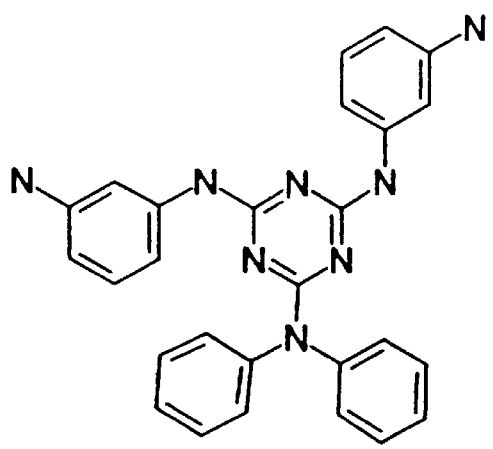
Figure 33:
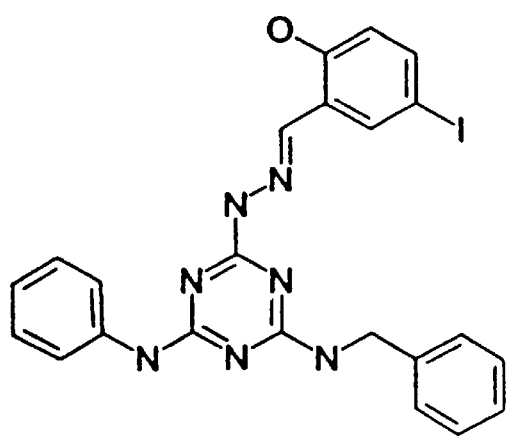
Figure 37:
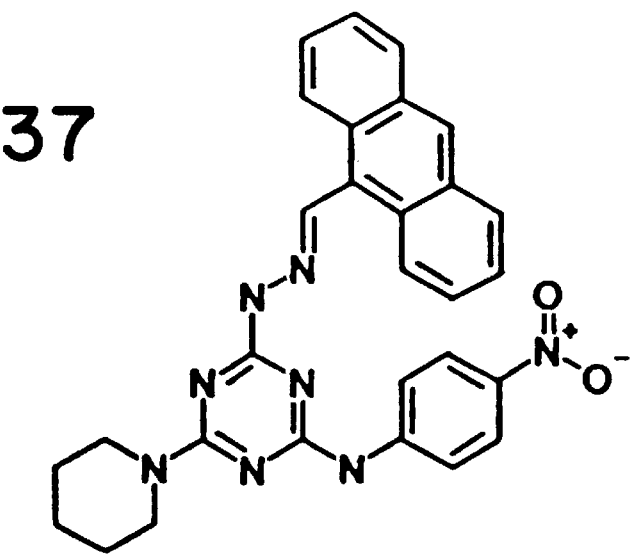
Figure 38:
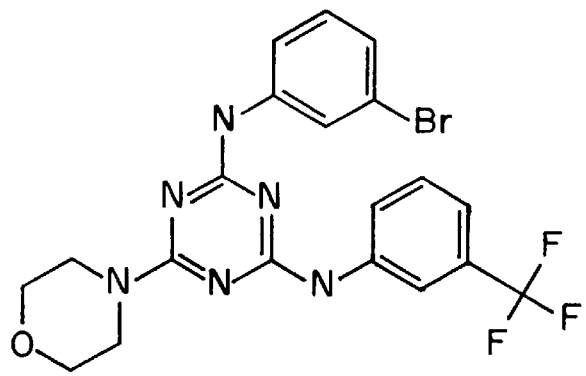
Figure 39:
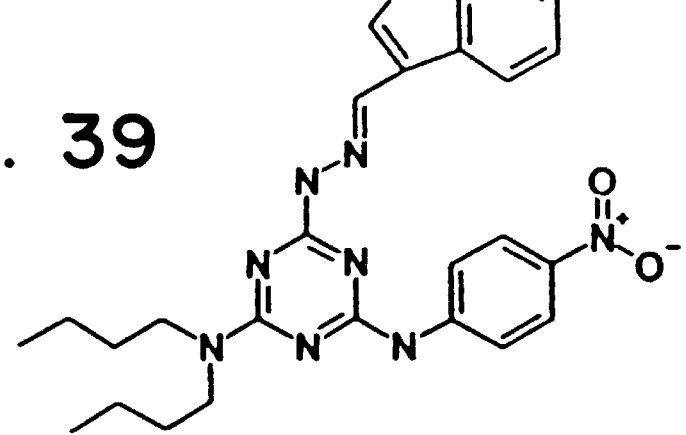
Figure 40:
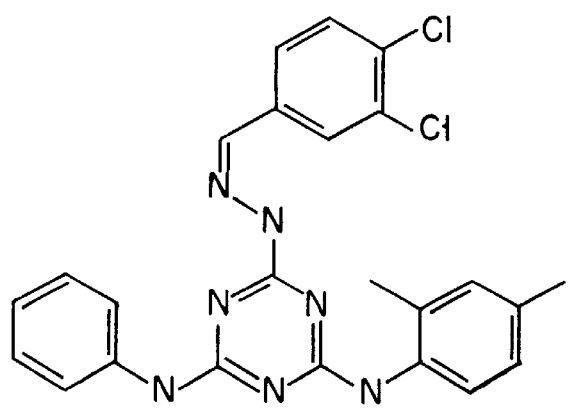
Figure 41:
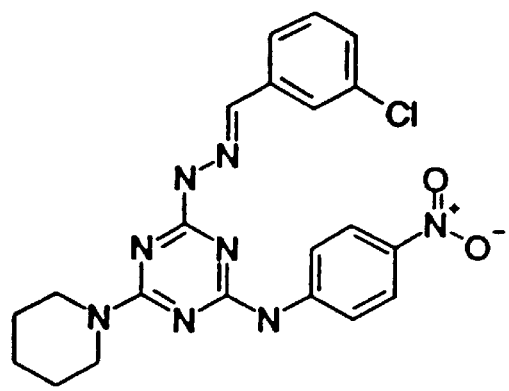
Figure 42:
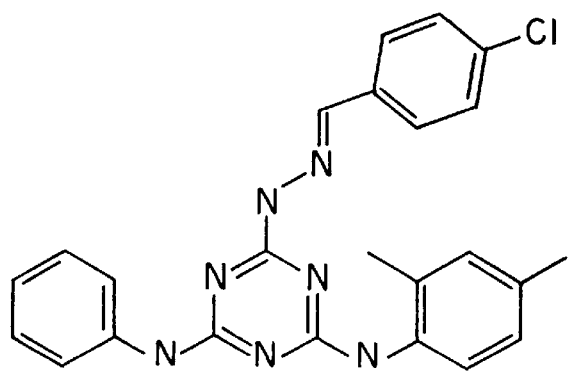
Figure 43:
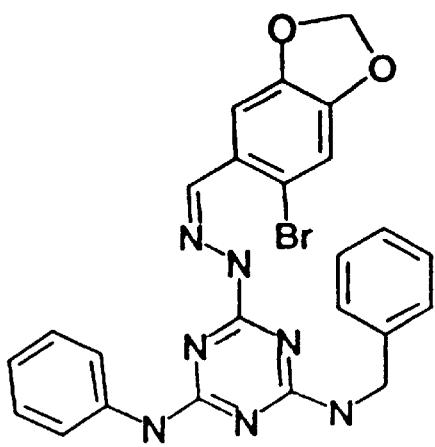
Figure 44:
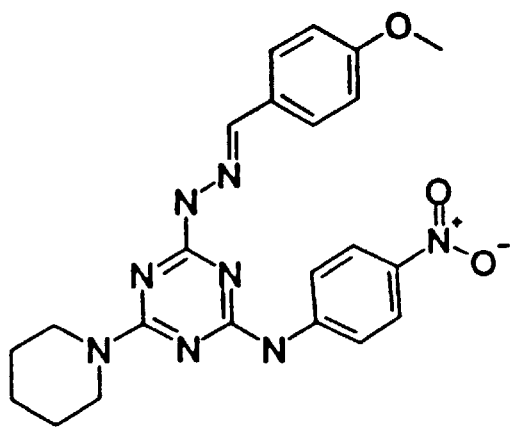
Figure 45:
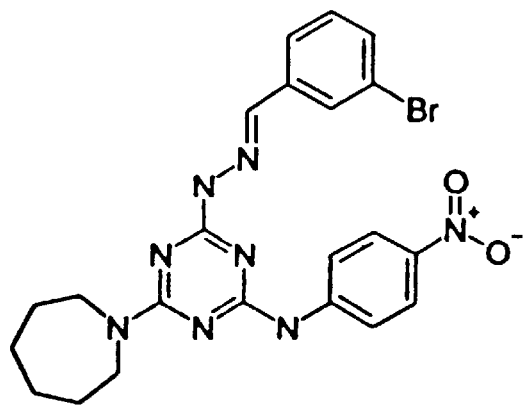
Figure 64:
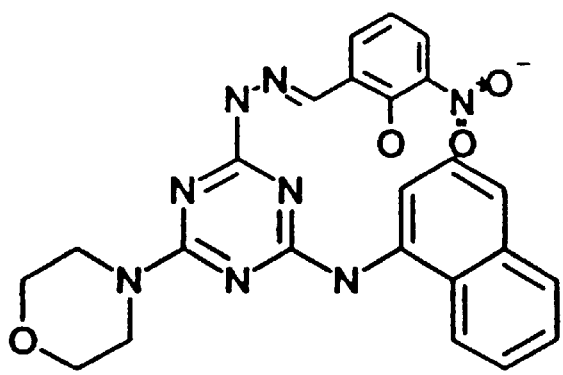
Figure 65:
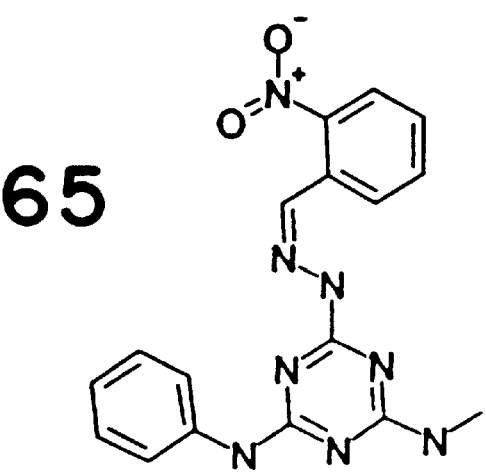
Figure 66:
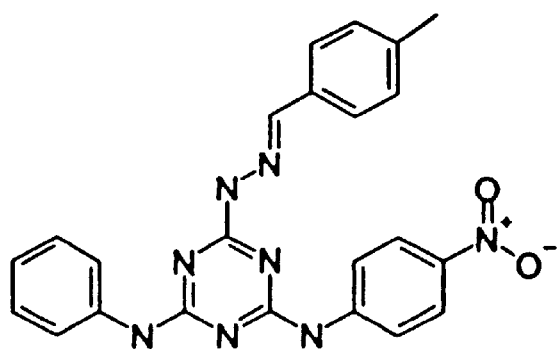
Figure 76:
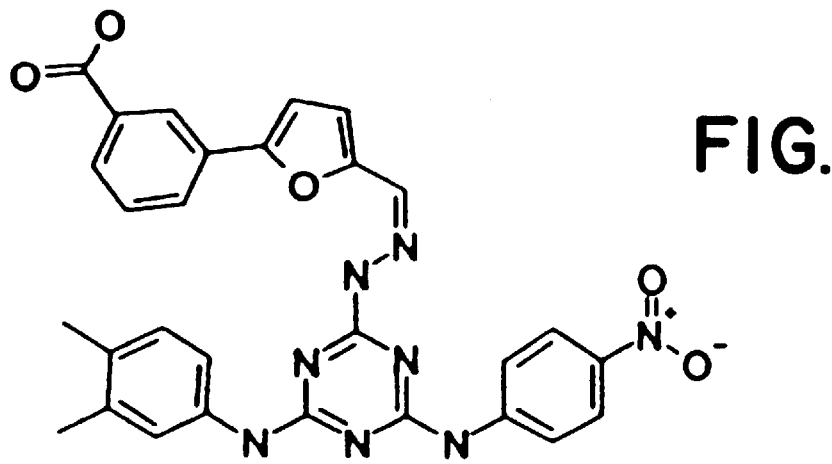
Figure 77:
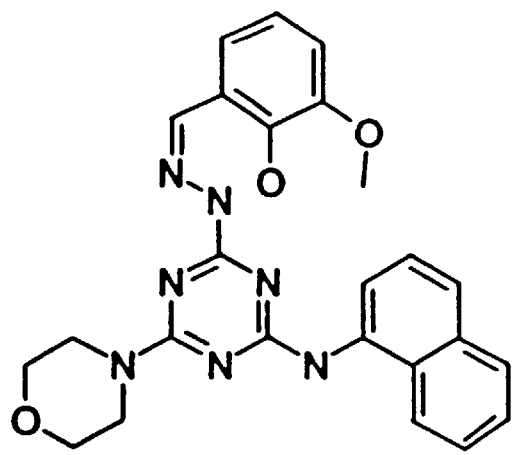
Figure 78:
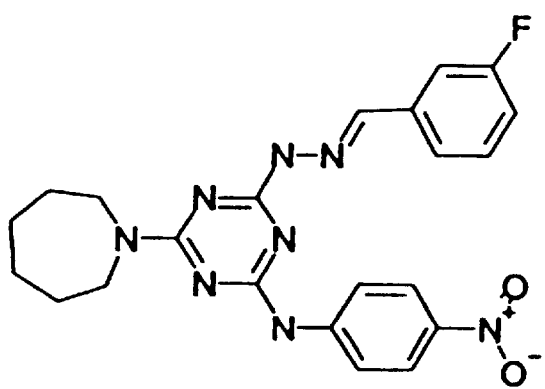
Figure 79:
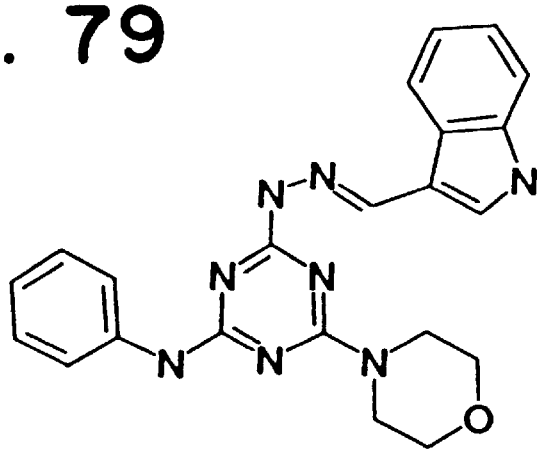
Figure 80:
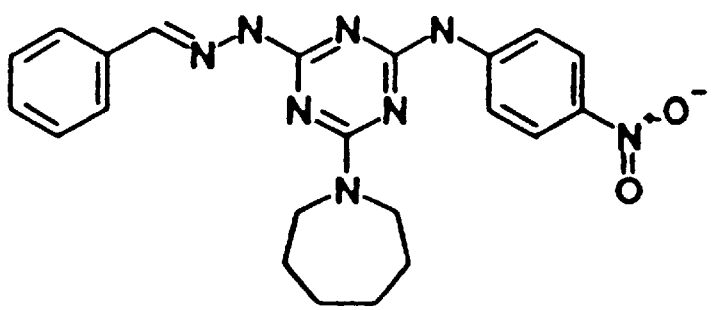
Figure 81:
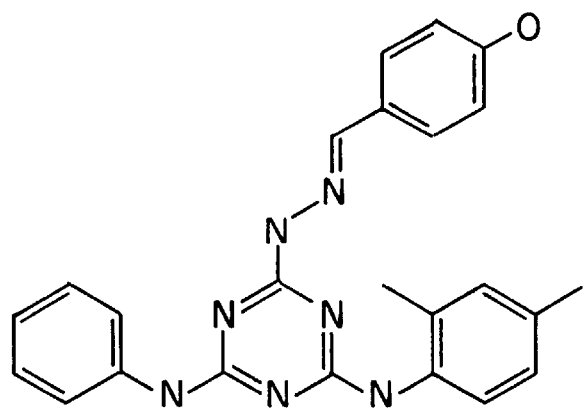
Figure 82:
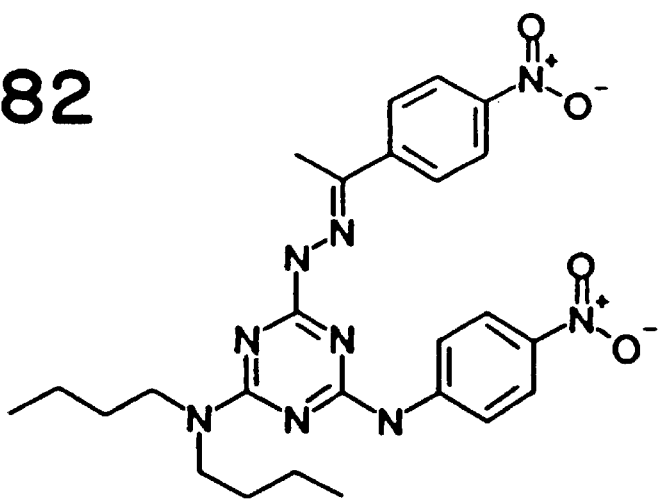
Figure 83:
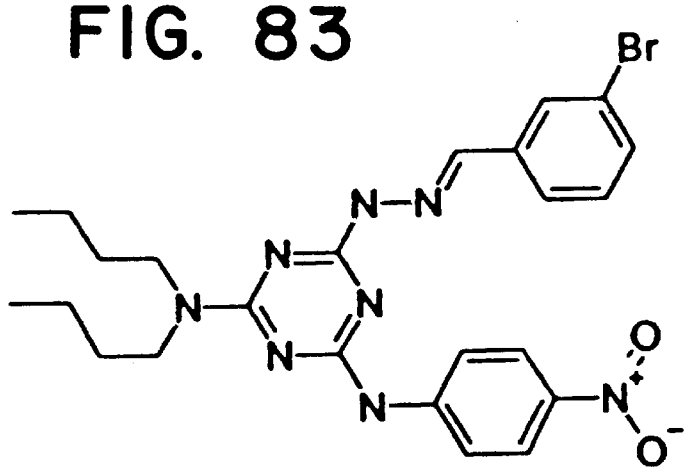
Figure 84:
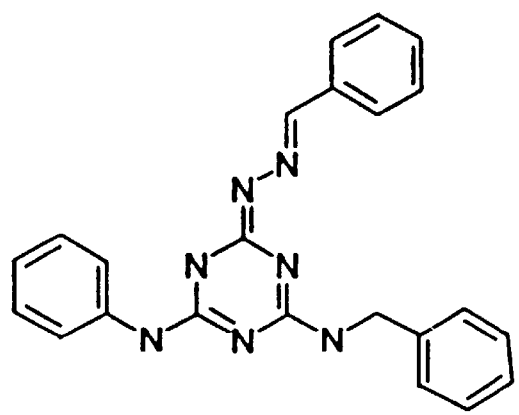
Figure 85:
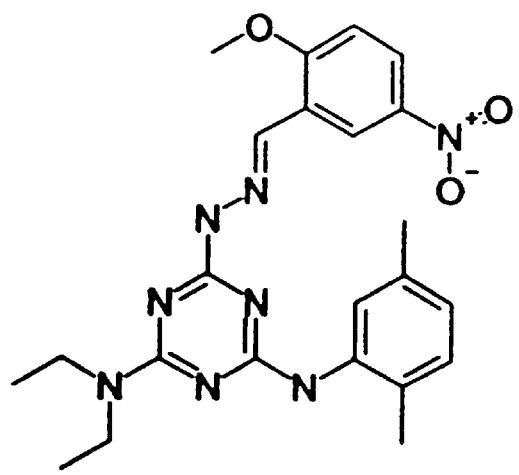
Figure 86:
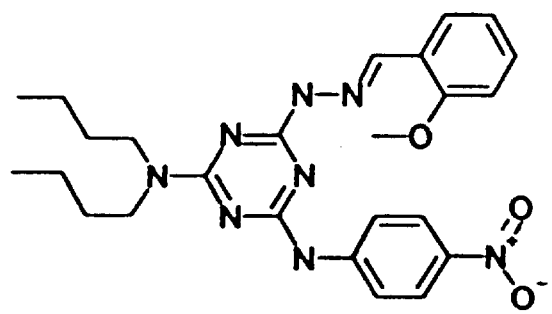
Figure 87:
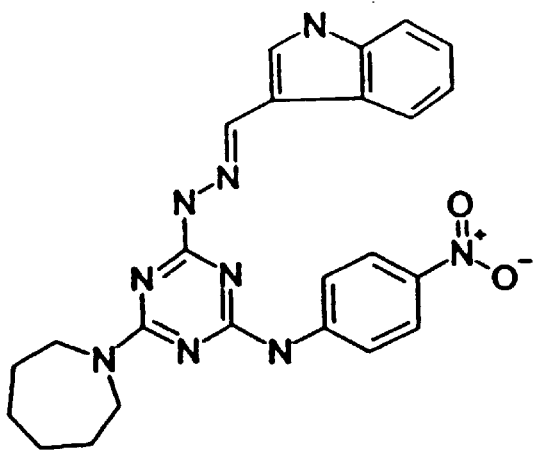
Figure 88:
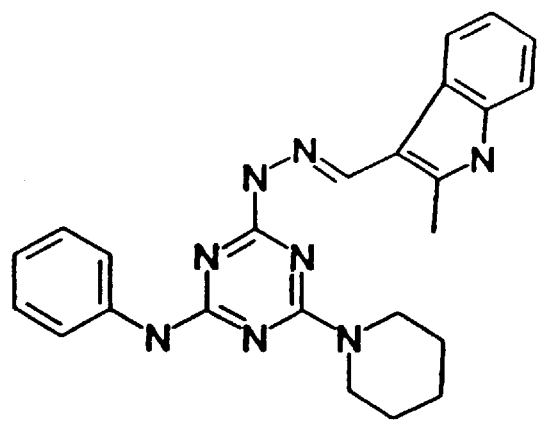
Figure 89:
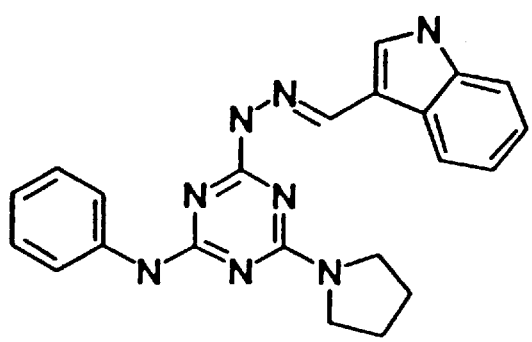
Figure 90:
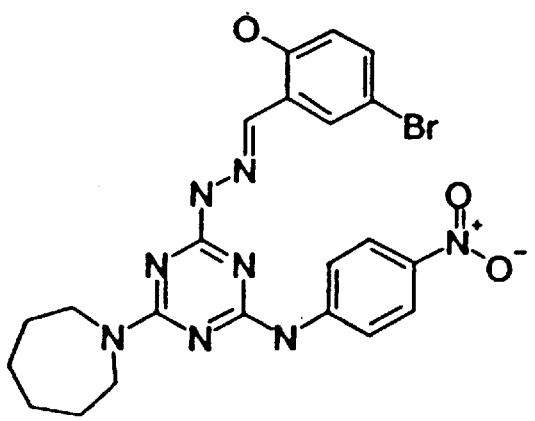
Figure 92:
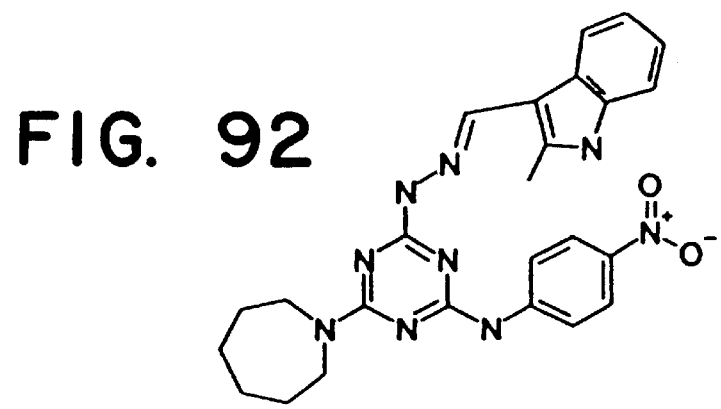
Figure 94:
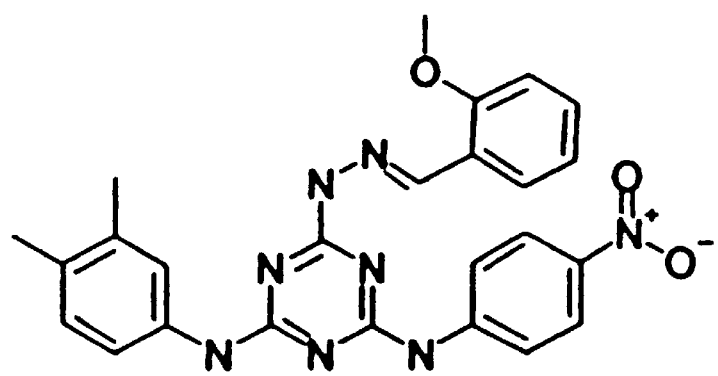
Figure 95:
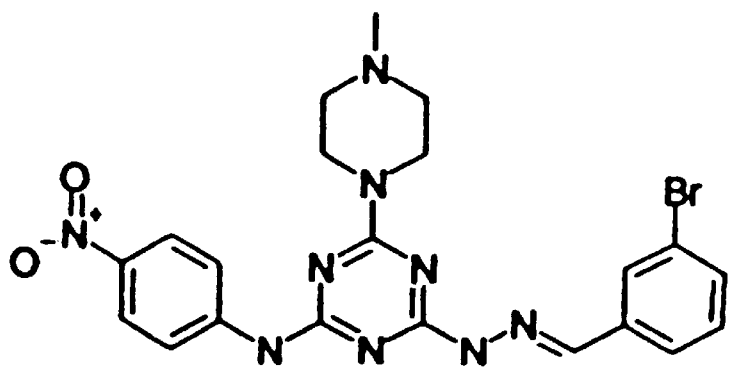
Figure 96:
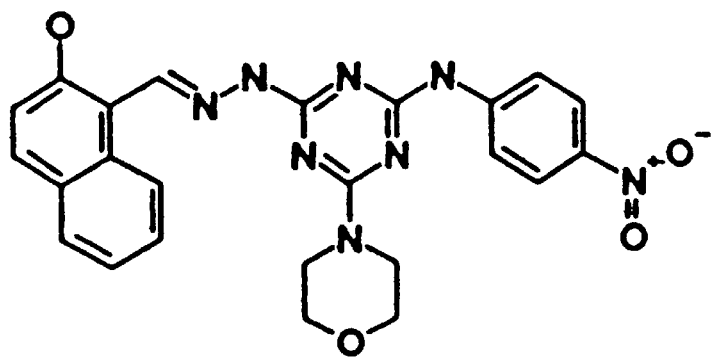
Figure 97:
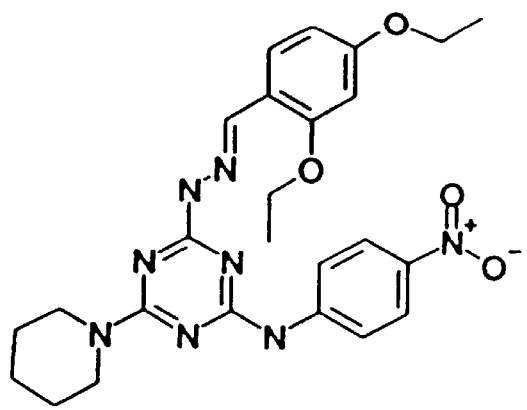
Figure 98:
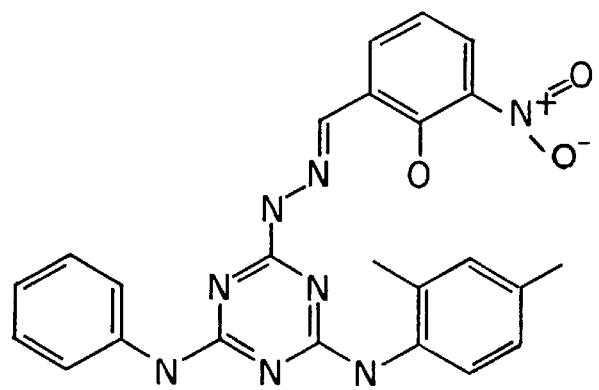
Figure 99:
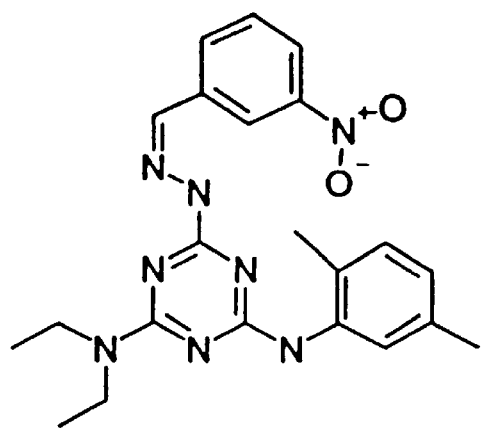
Figure 100:
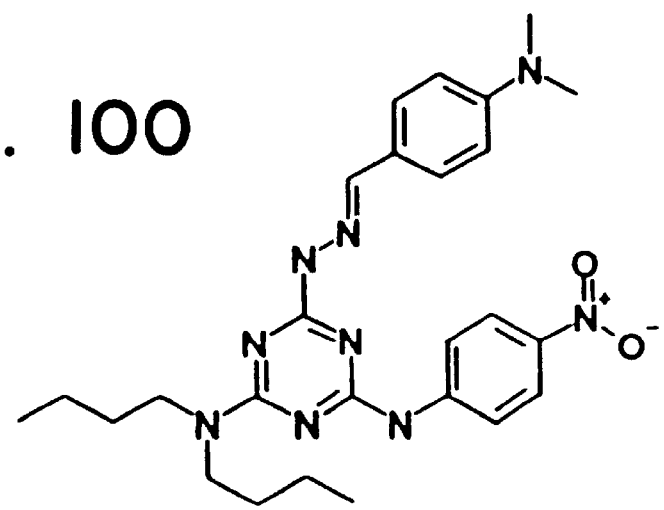
Figure 101:
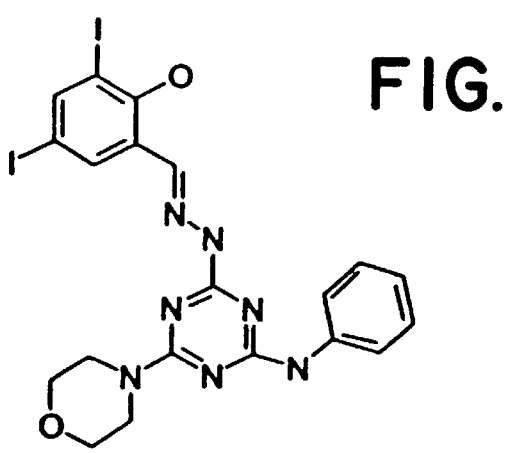
Figure 102:
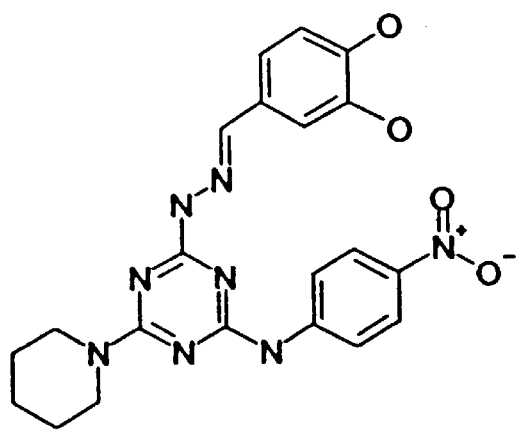
Figure 103:
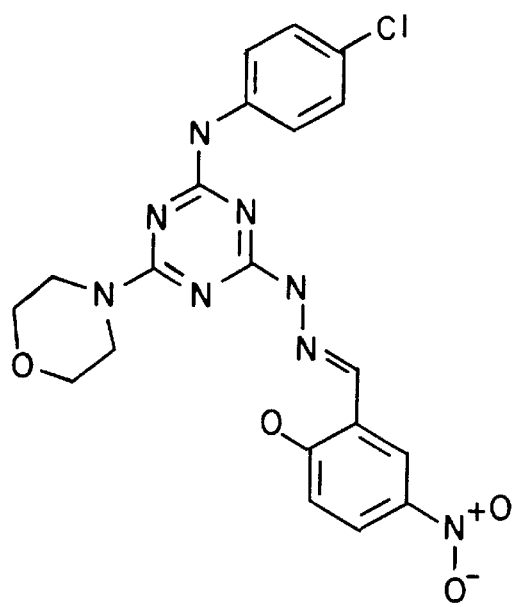
Figure 104:
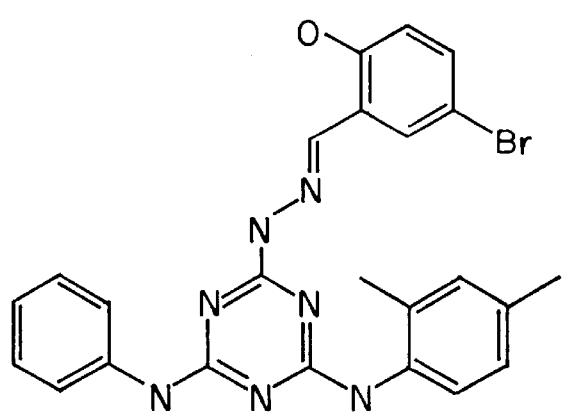
Figure 105:
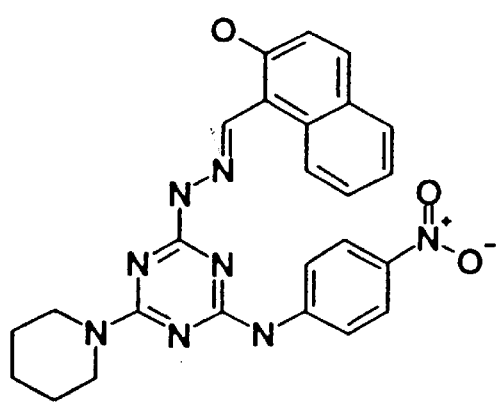
Figure 106:
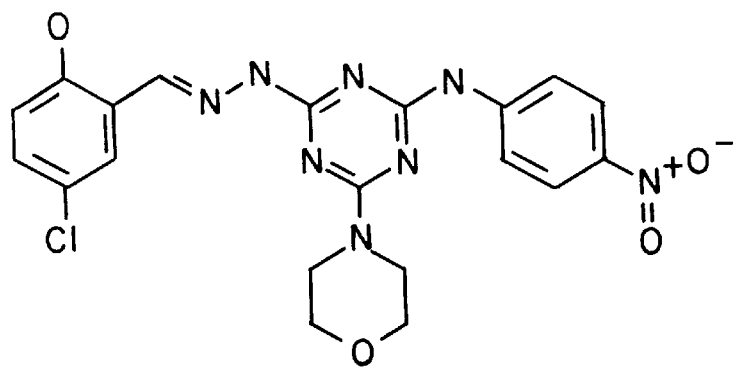
Figure 107:
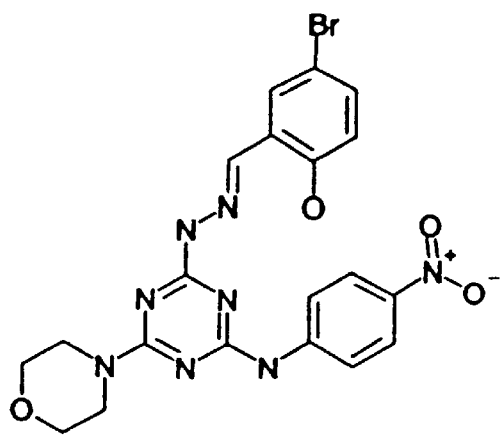
Figure 108:
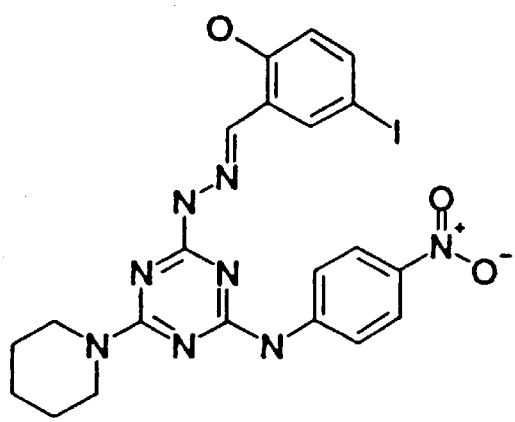
Figure 109:
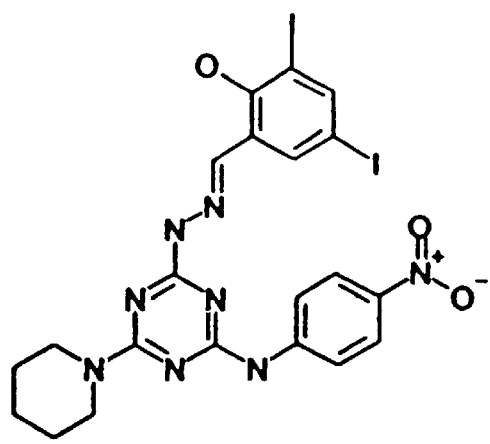
Figure 110:
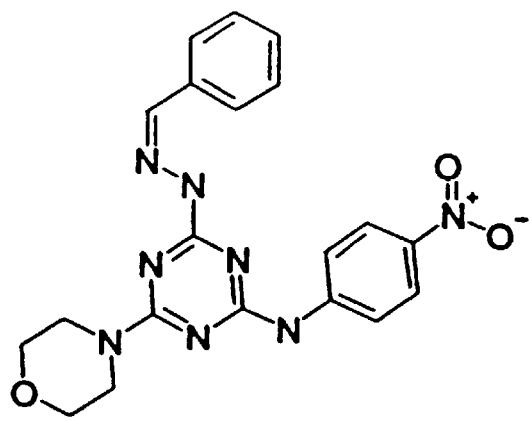
Figure 111:
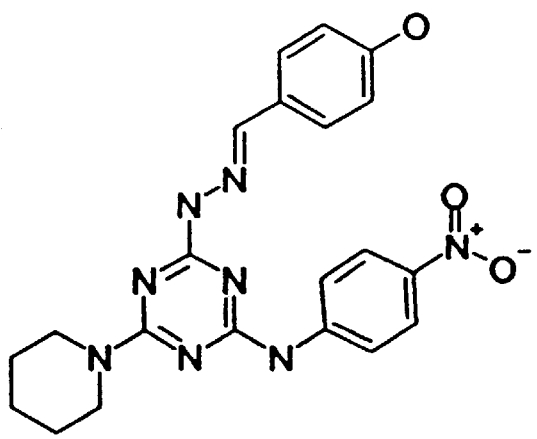
Figure 112:
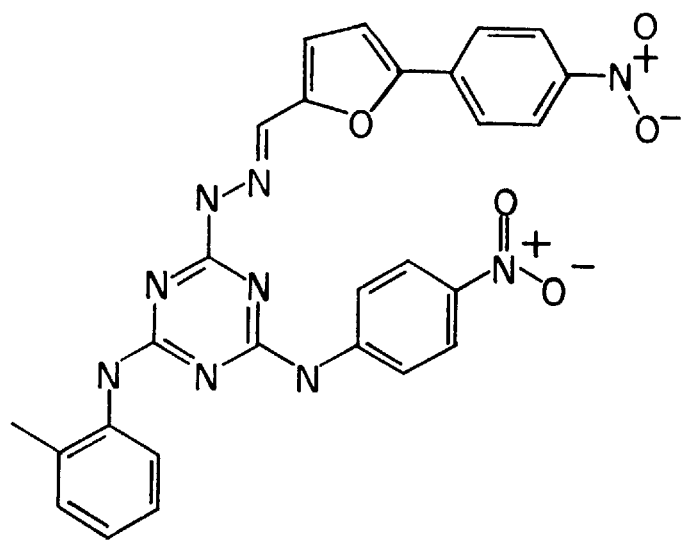
Figure 113:
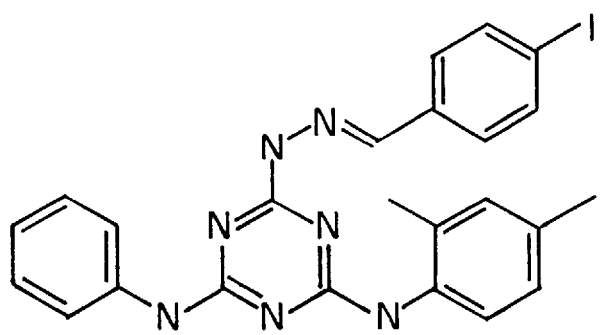
Figure 114:
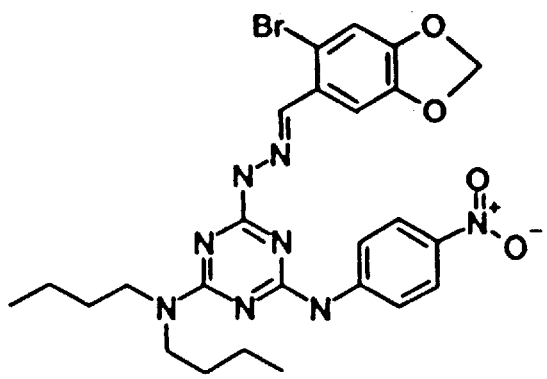
Figure 115:
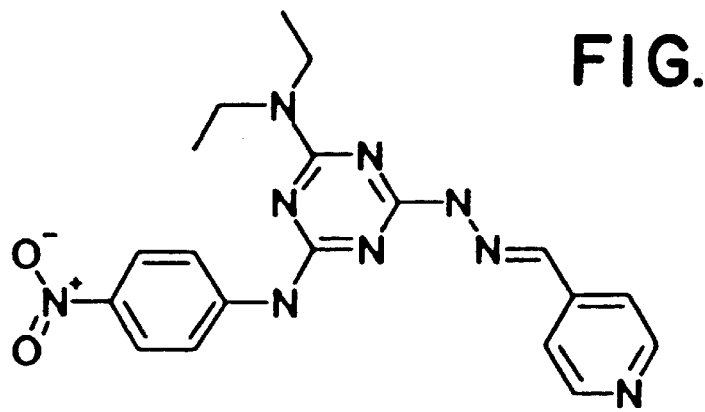
Figure 116:
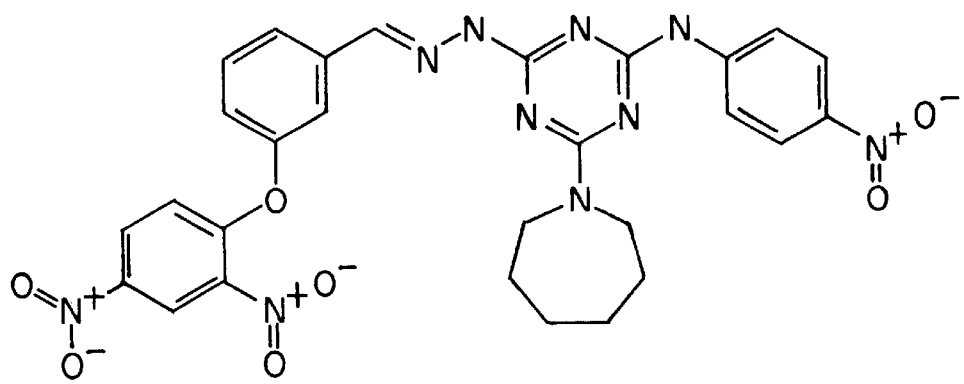
Figure 117:
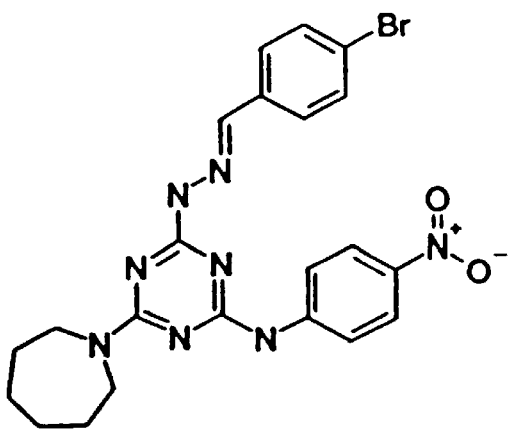
Figure 118:
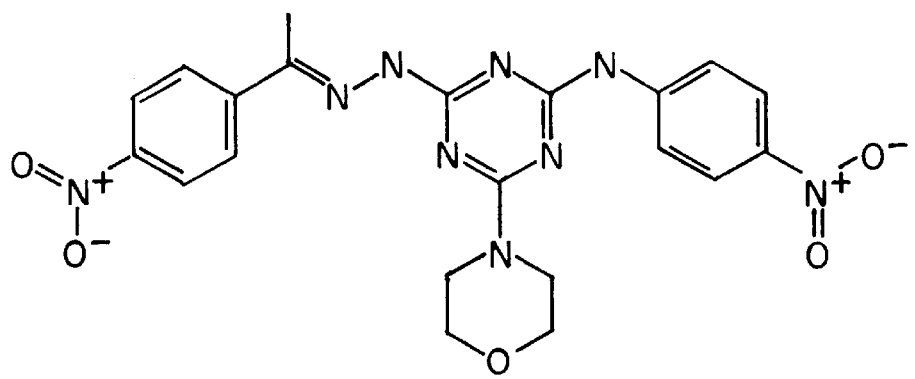
Figure 119:
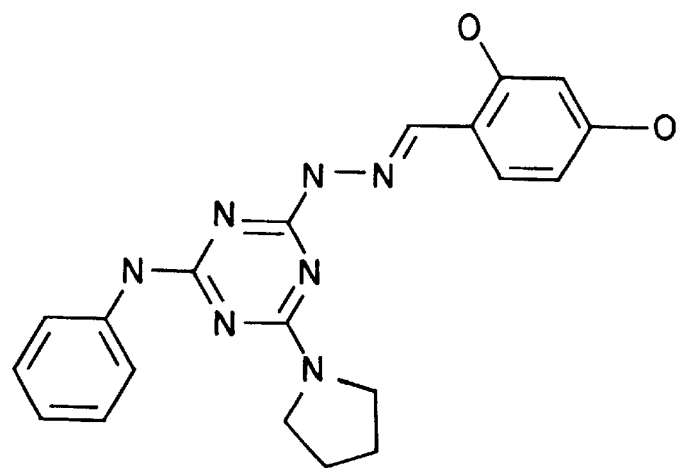
Figure 120:
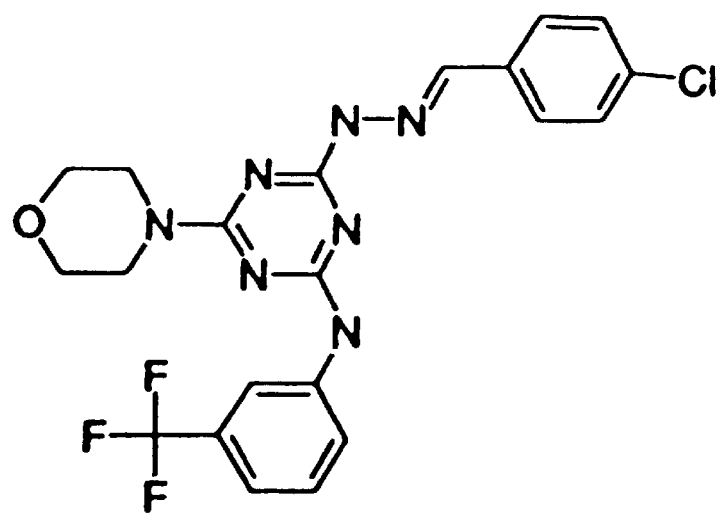
Figure 121:
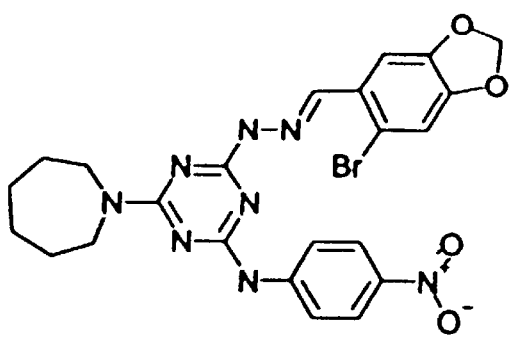
Figure 122:
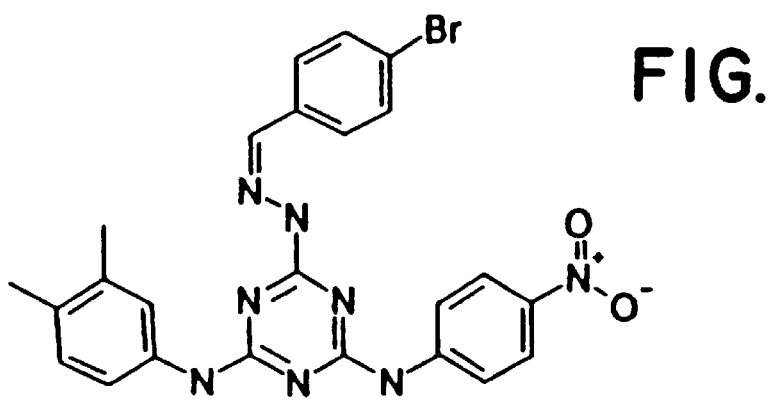
Figure 123:
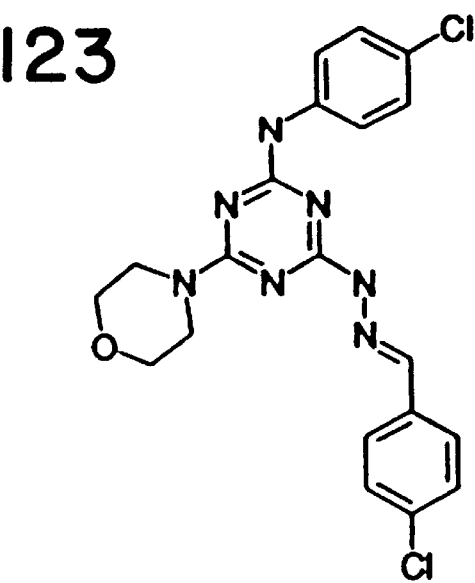
Figure 127:
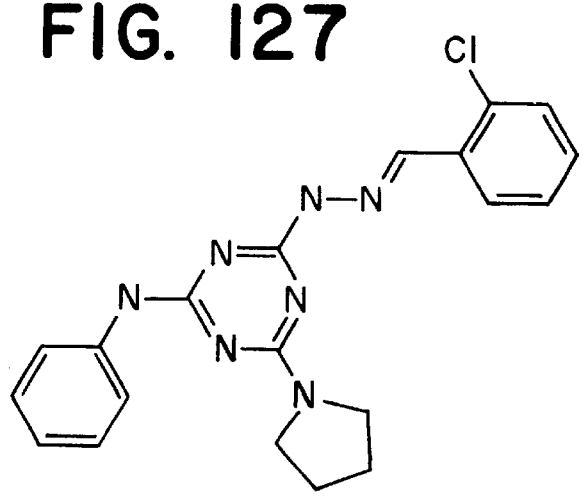
Figure 128:
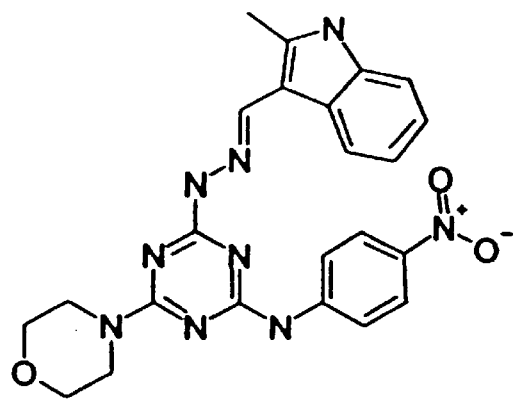
Figure 129:
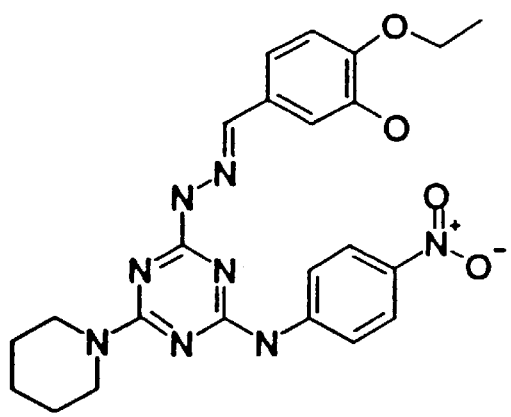
Figure 130:
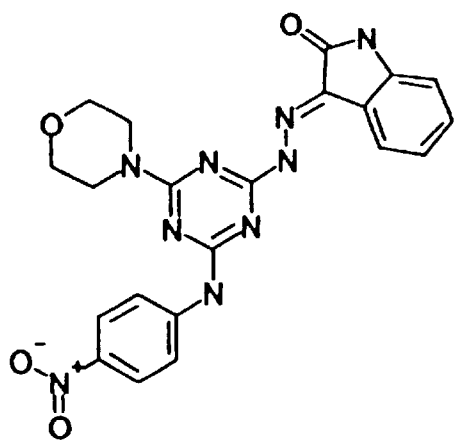
Figure 131:
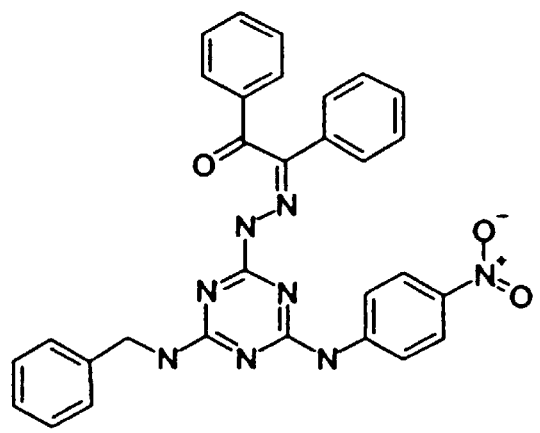
Figure 132:
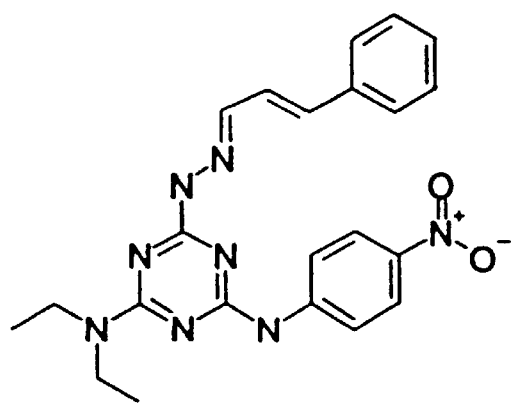
Figure 133:
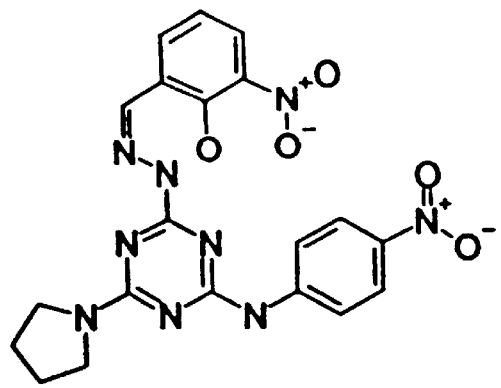
Figure 134:
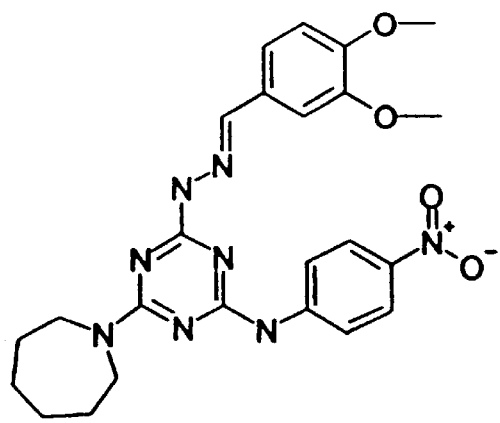
Figure 135:
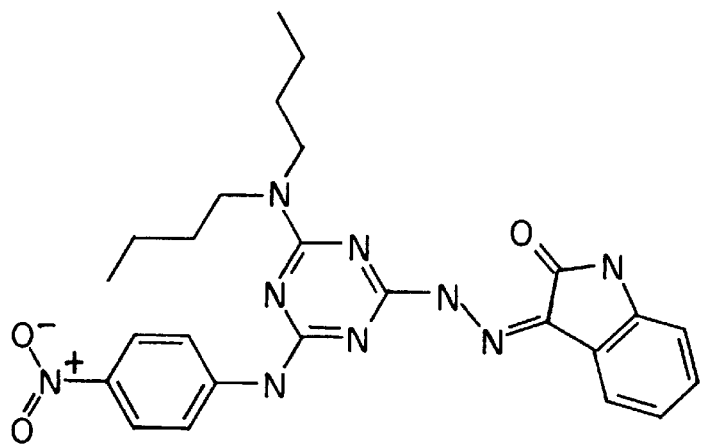
Figure 136:
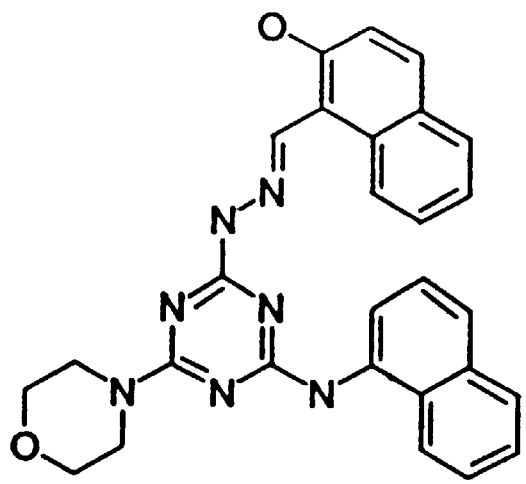
Figure 137:
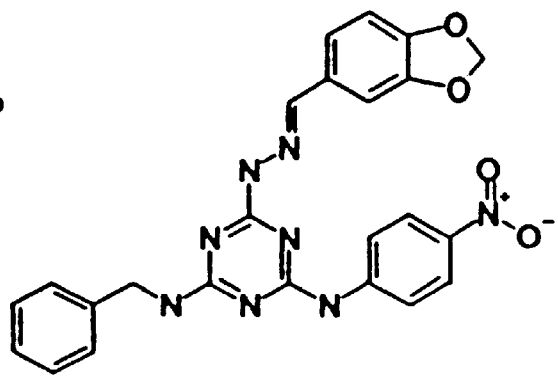
Figure 138:
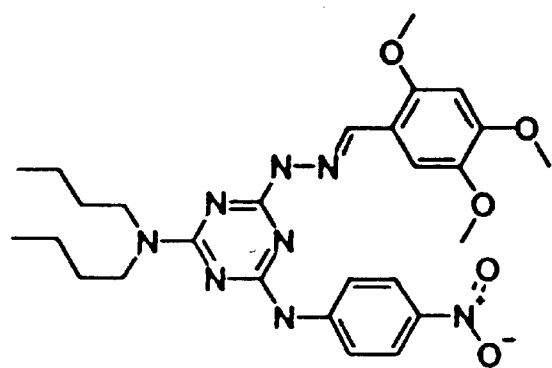
Figure 139:
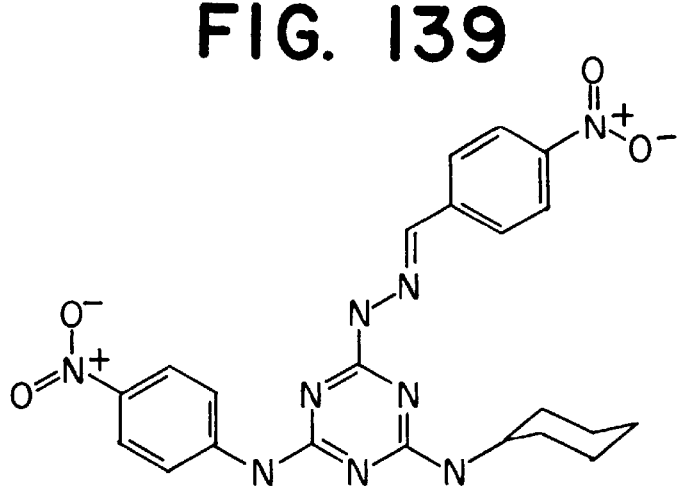
Figure 140:
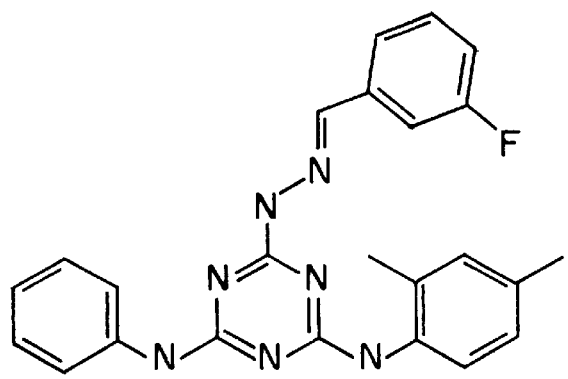
Figure 141:
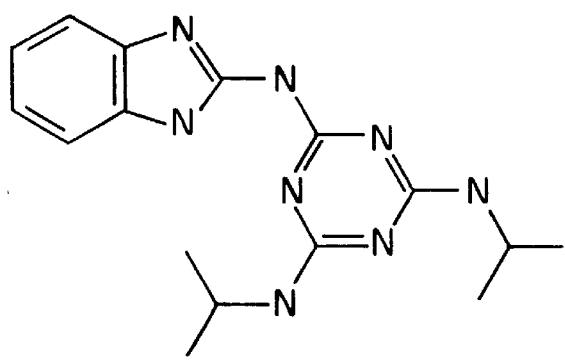
Figure 142:
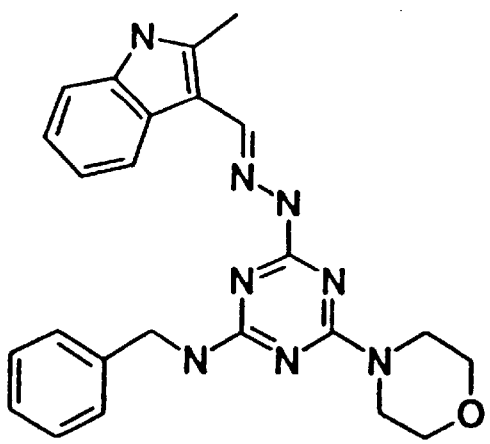
Figure 143:
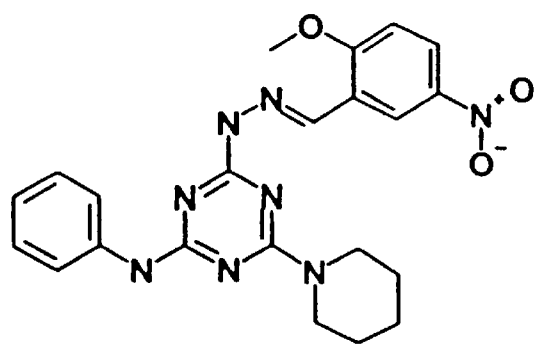
Figure 144:
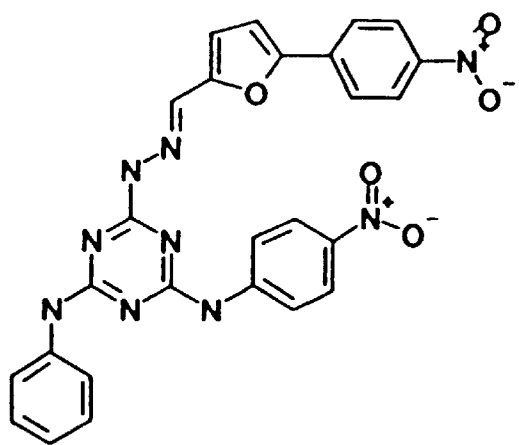
Figure 145:
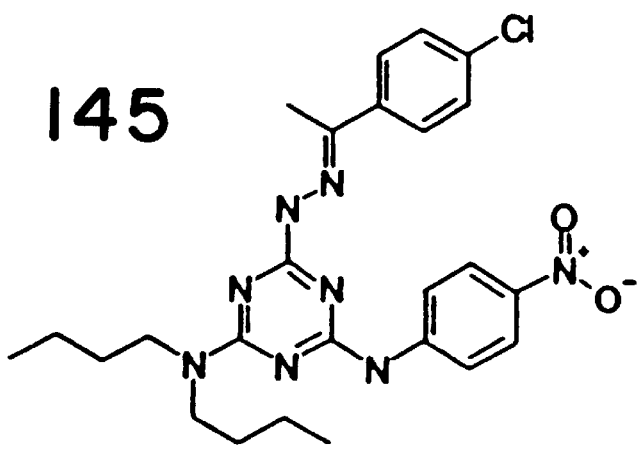
Figure 146:
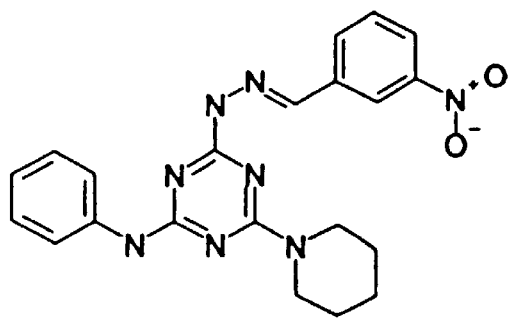
Figure 147:
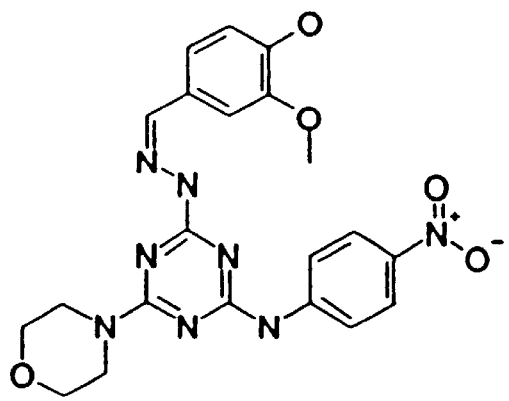
Figure 148:
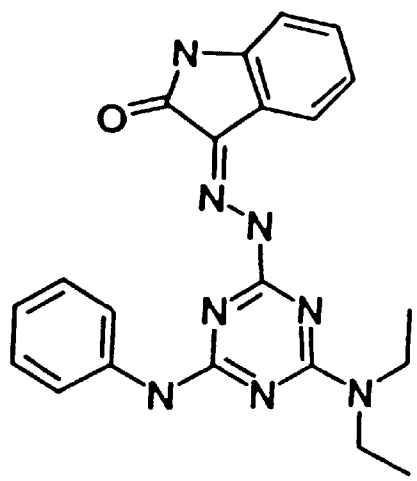
Figure 149:
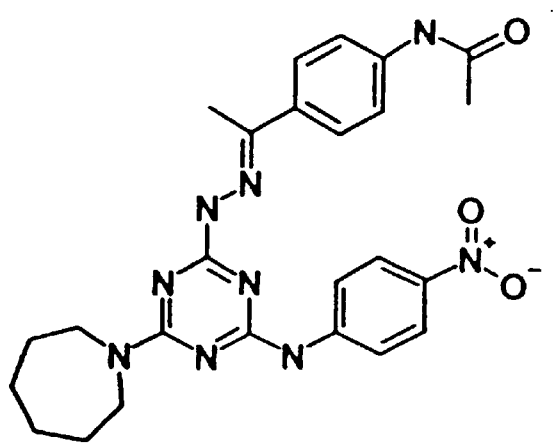
Figure 150:
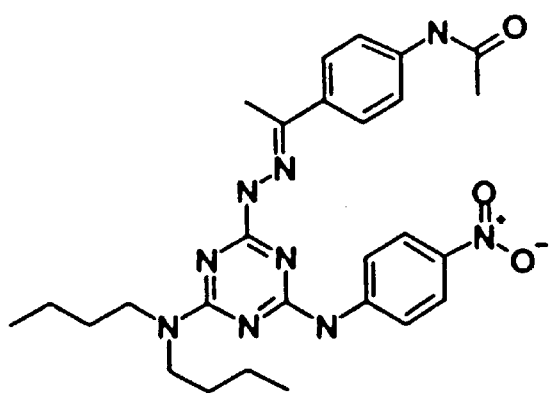
Figure 154:
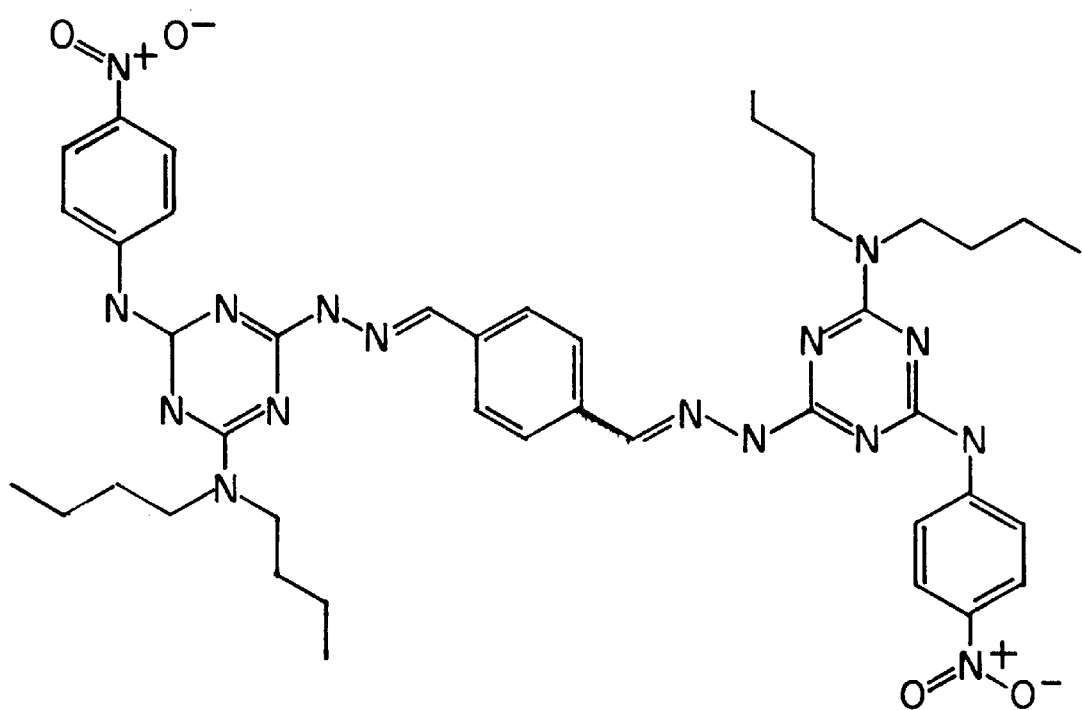
Figure 155:
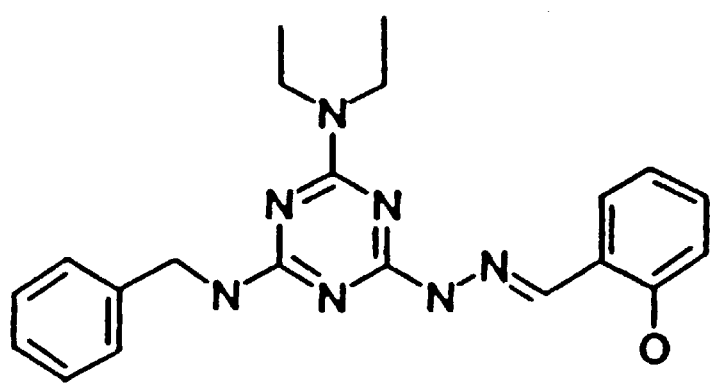
Figure 156:
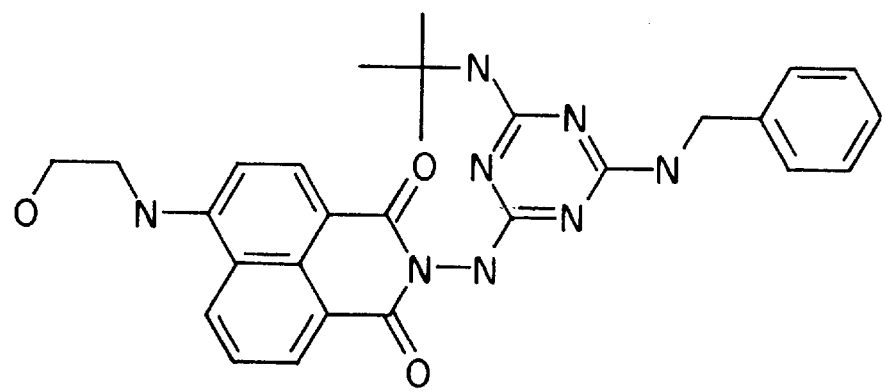
Figure 157:
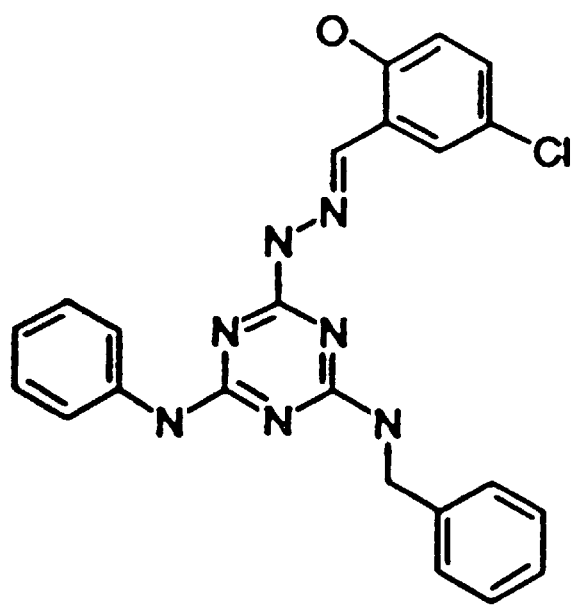
Figure 158:
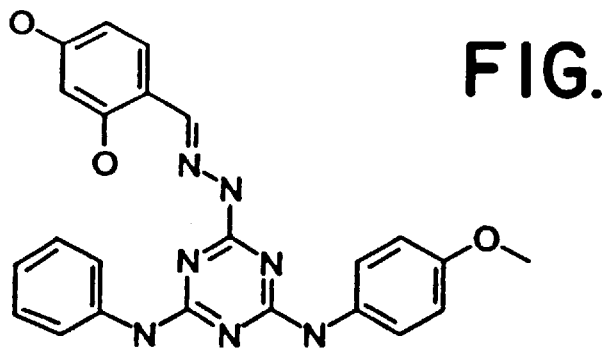
Figure 159:
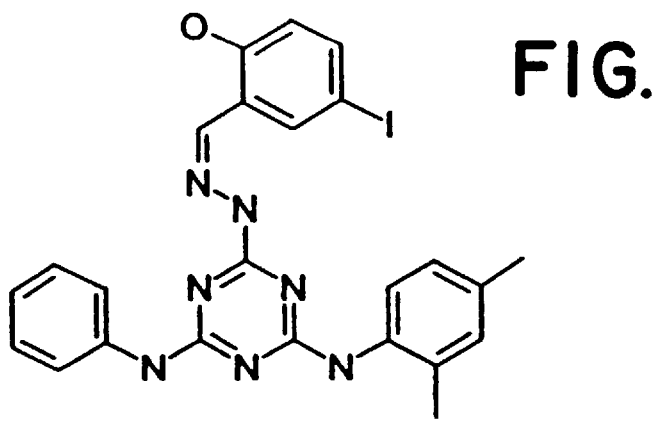
Figure 160:
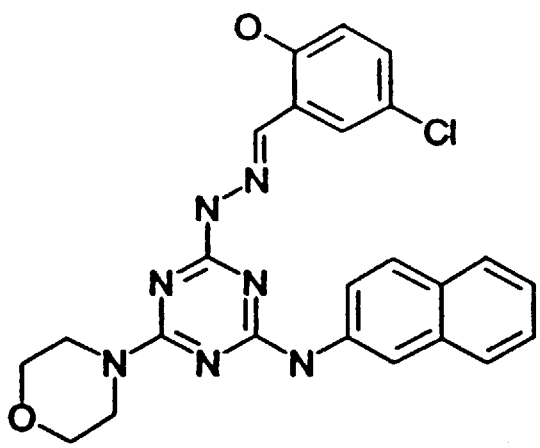
Figure 161:
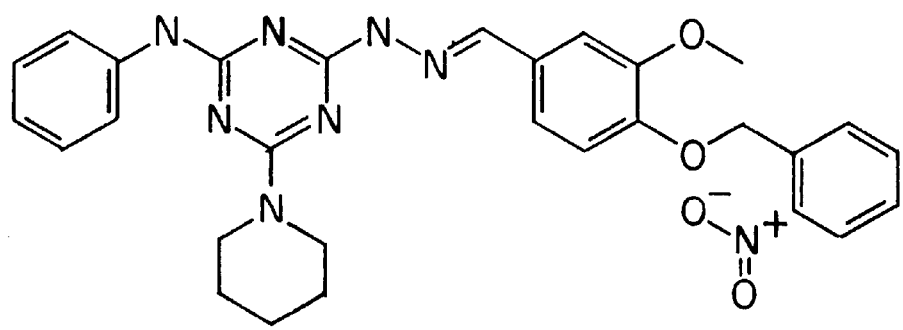
Figure 162:
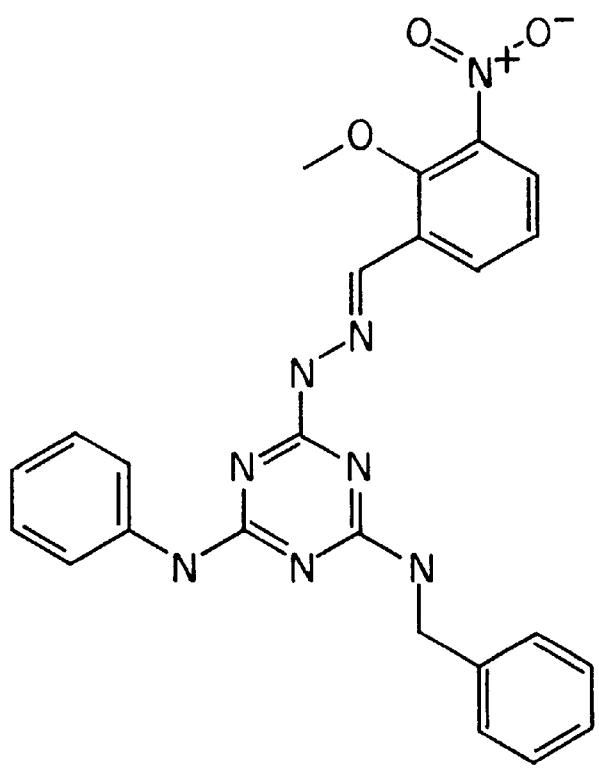
Figure 166:
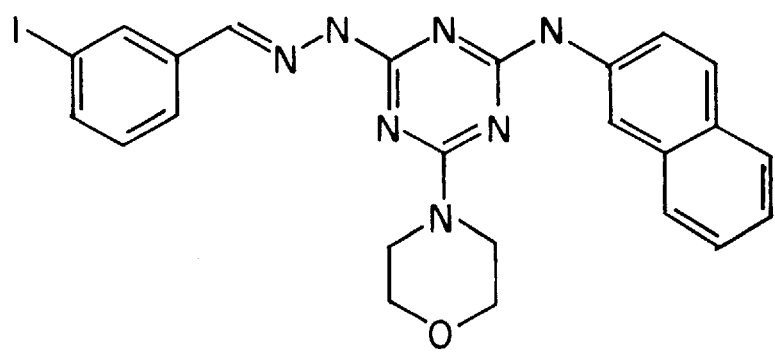
Figure 167:
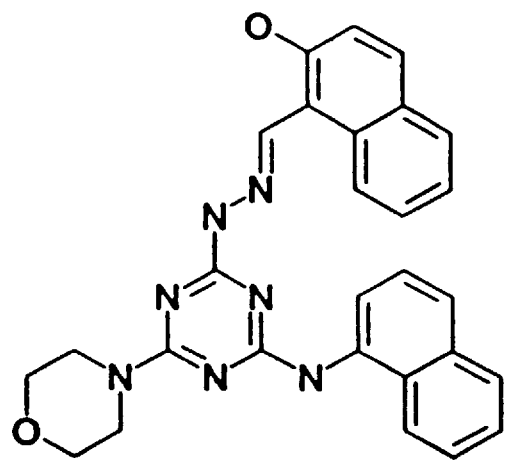
Figure 168:
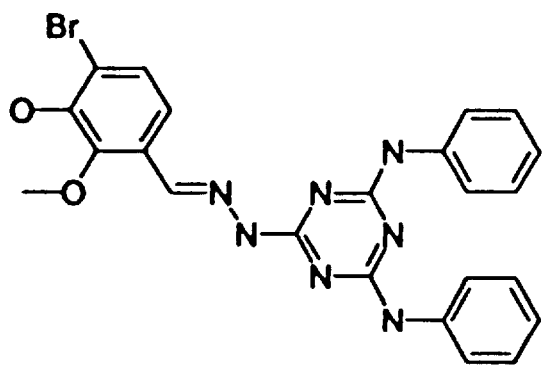
Figure 169:
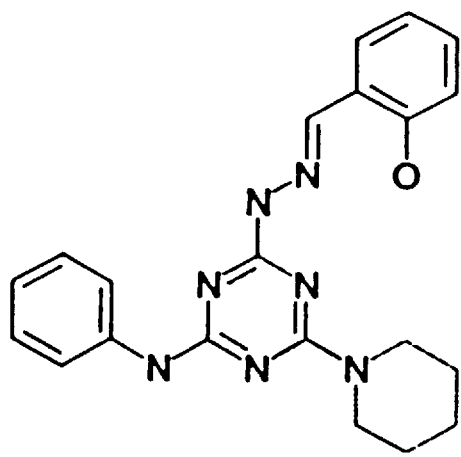
Figure 170:
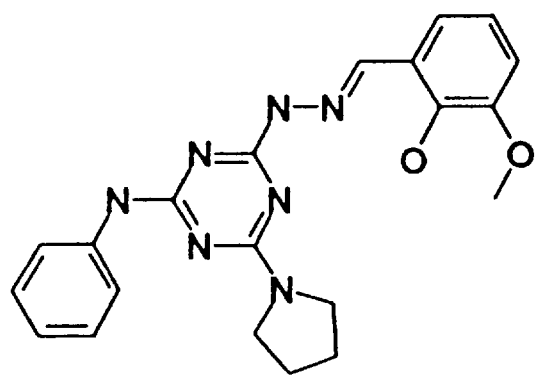
Figure 171:
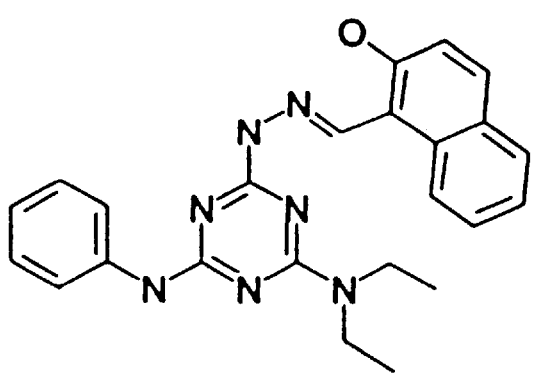
Figure 172:
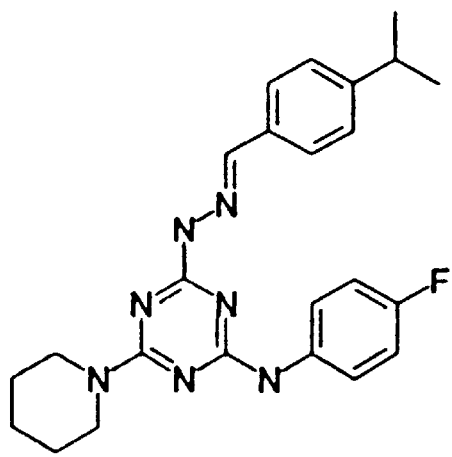
Figure 173:
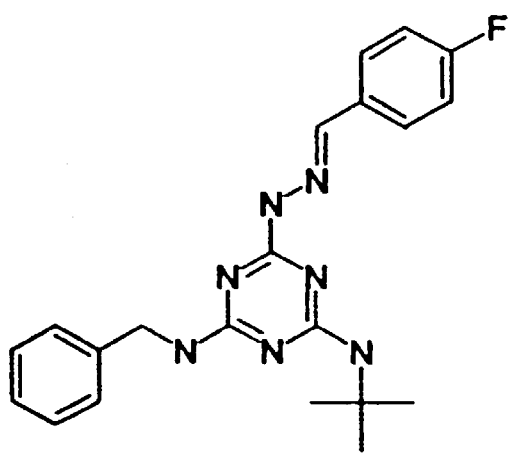
Figure 174:
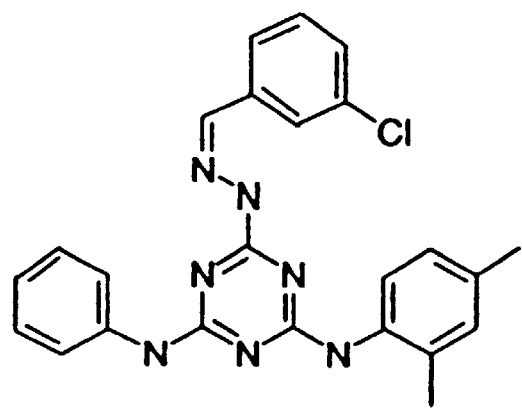
Figure 175:
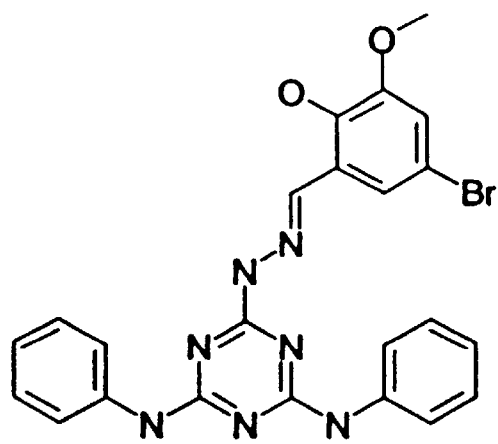
Figure 176:
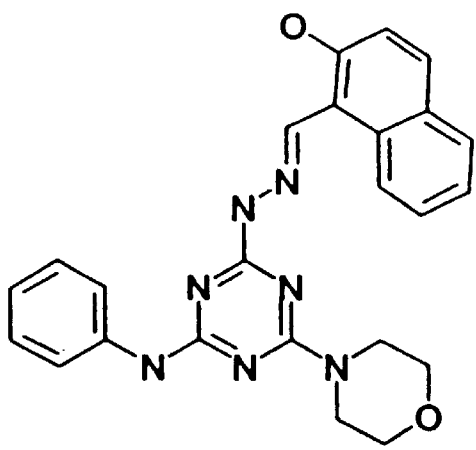
Figure 177:
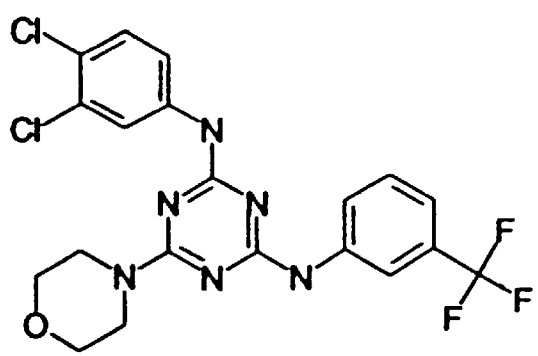
Figure 178:
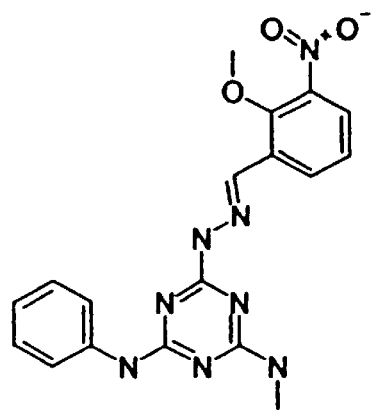
Figure 179:
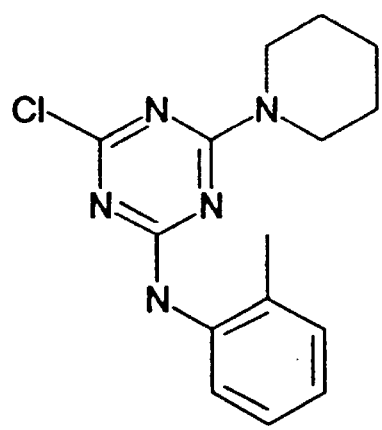
Figure 180:
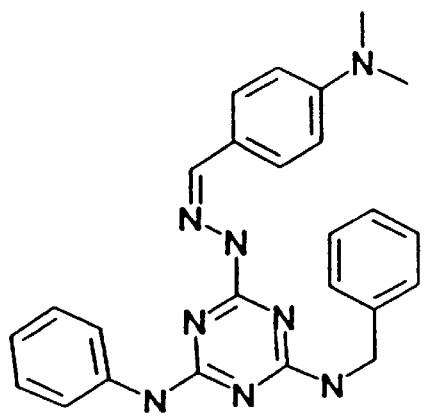
Figure 181:
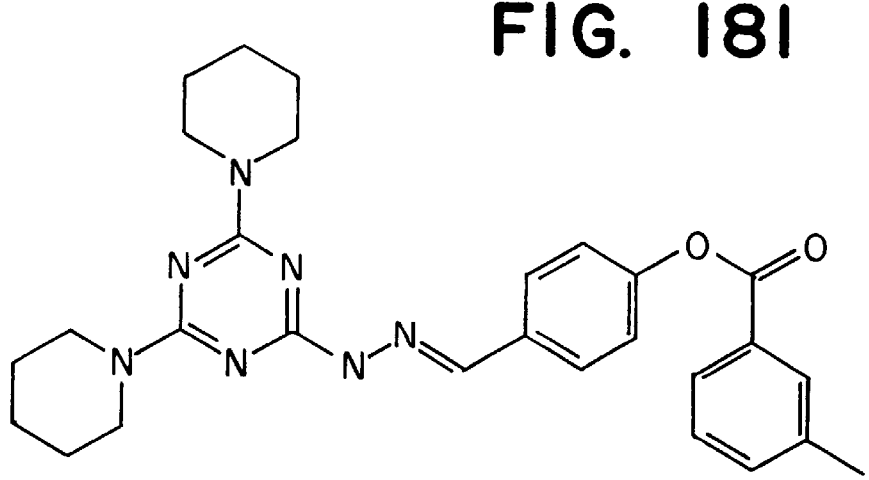
Figure 182:
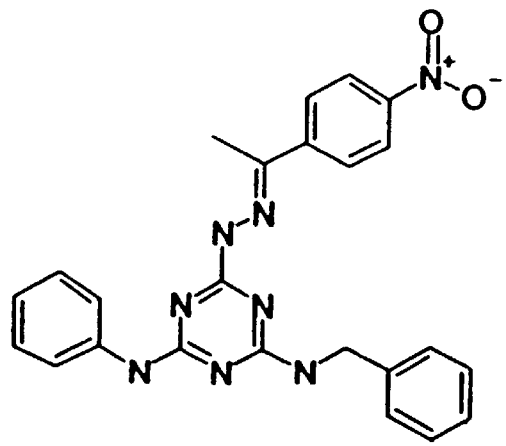
Figure 183:
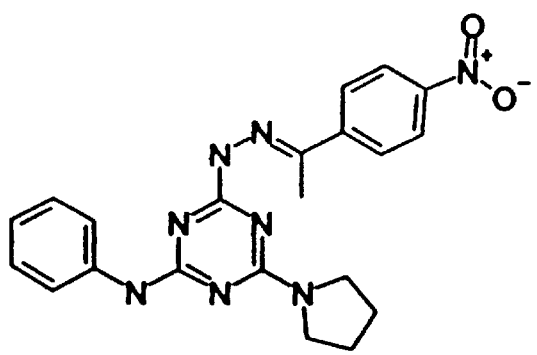
Figure 184:
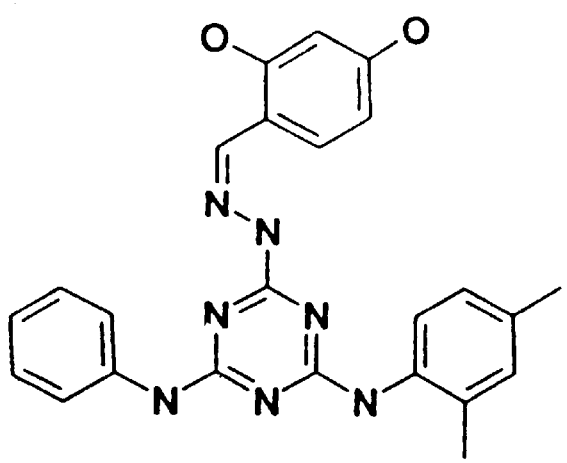
Figure 185:
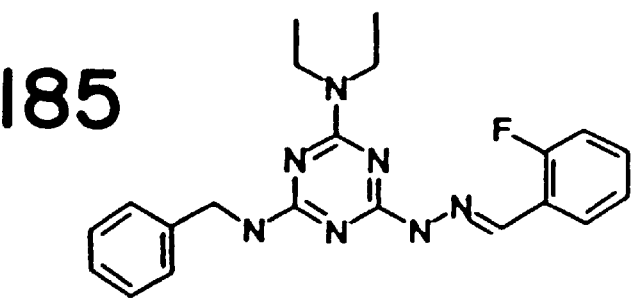
Figure 186:
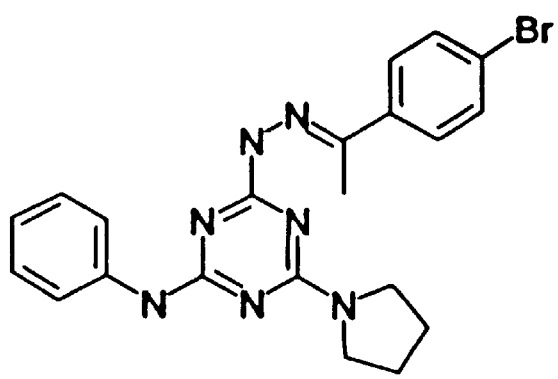
Figure 187:
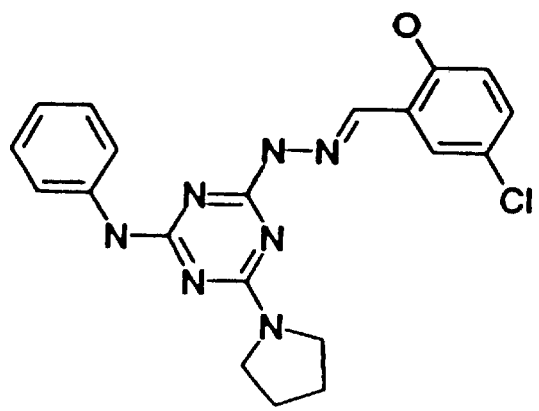
Figure 188:
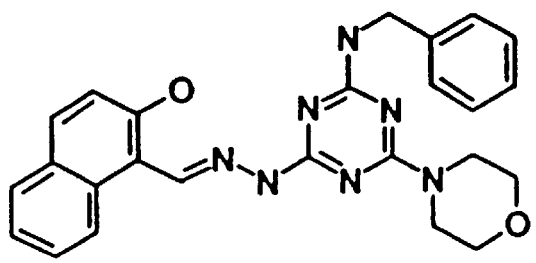
Figure 189:
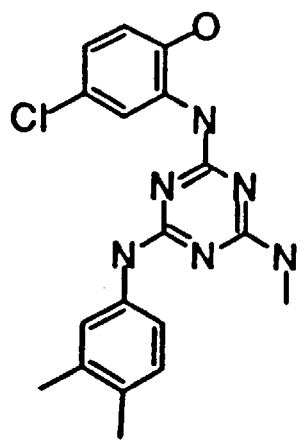
Figure 190:
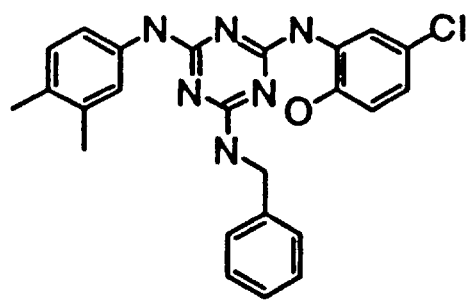
Figure 191:
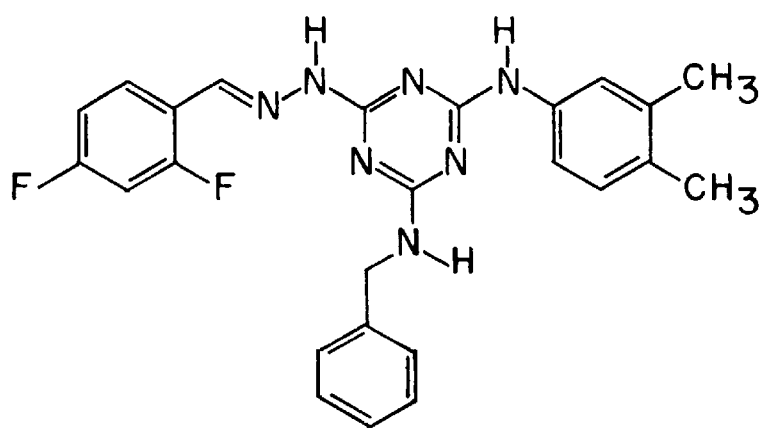
Figure 192:
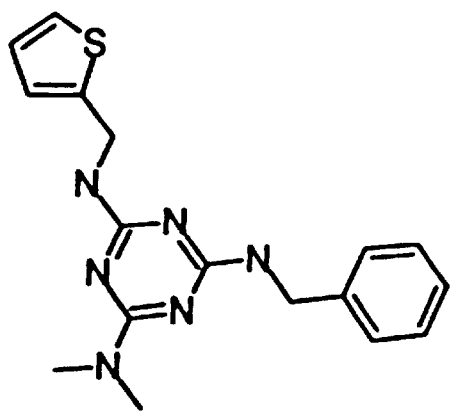
Figure 193:
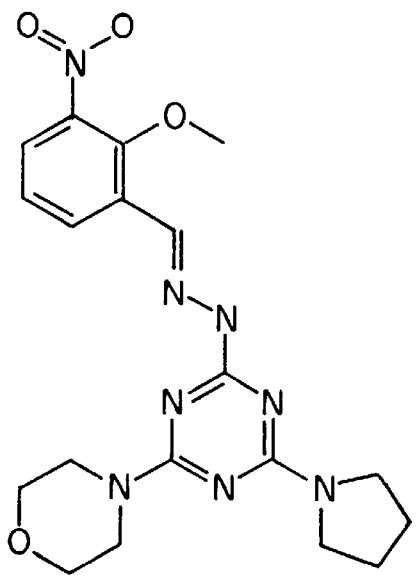
Figure 194:
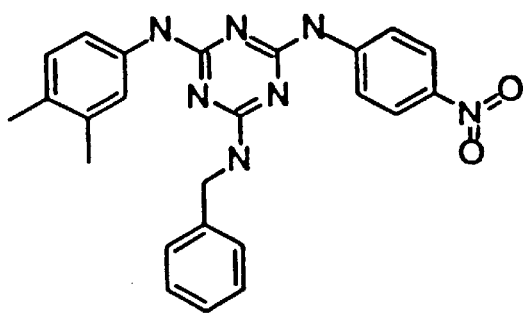
Figure 195:
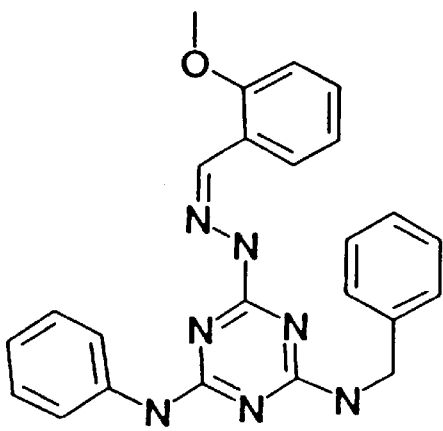
Figure 196:
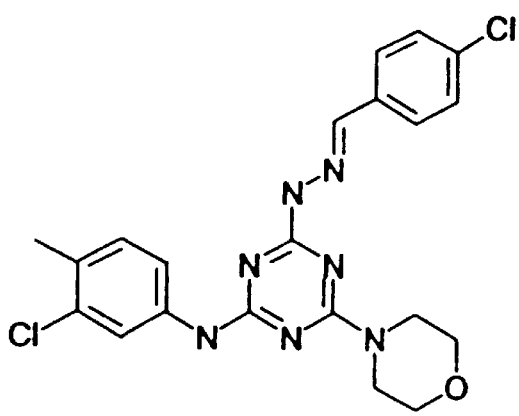
Figure 197:
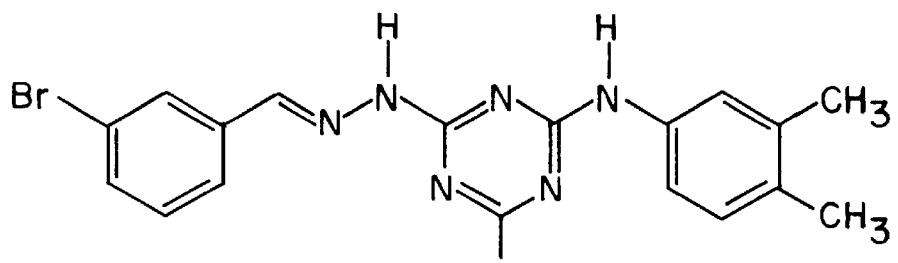
Figure 198:
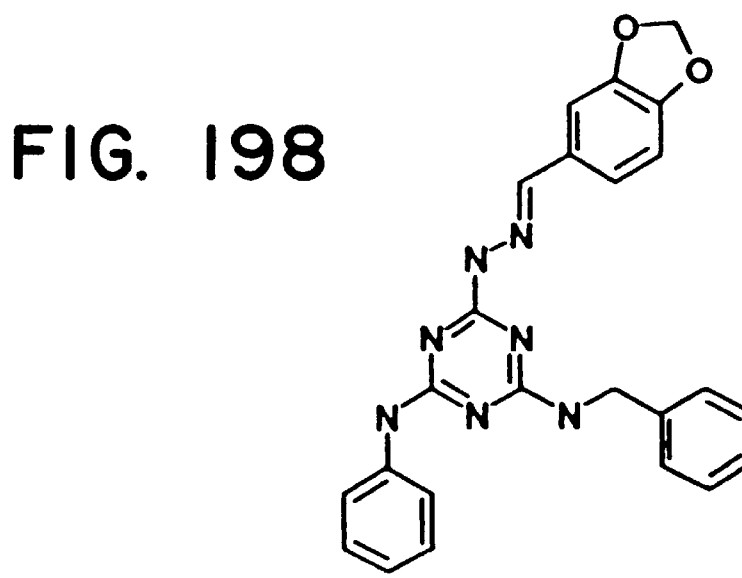
Figure 199:
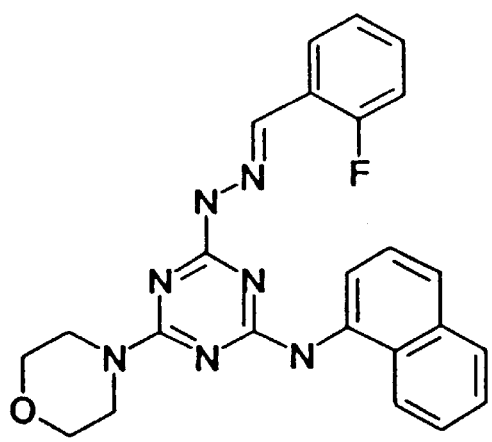
Figure 200:
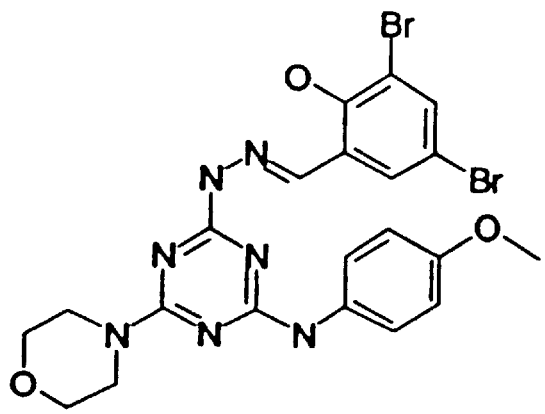
Figure 201:
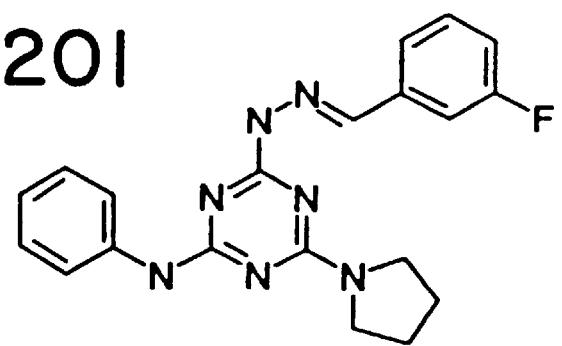
Figure 202:
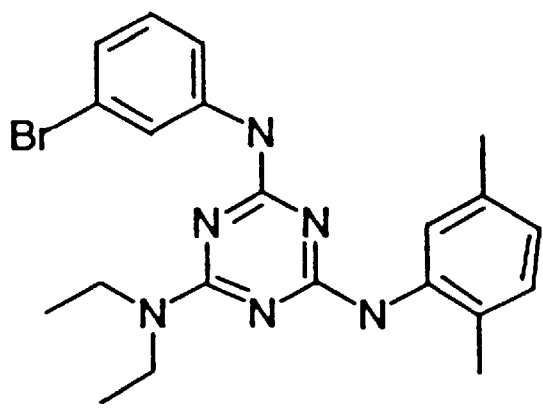
Figure 203:
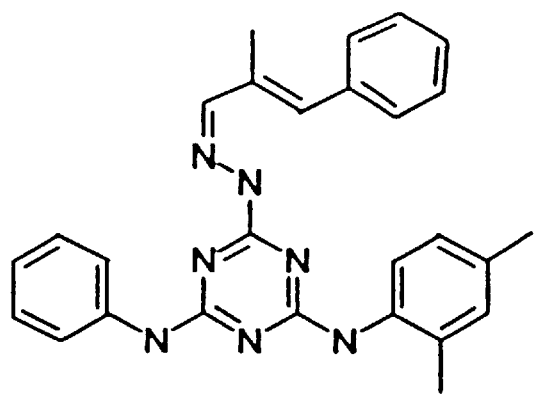
Figure 204:
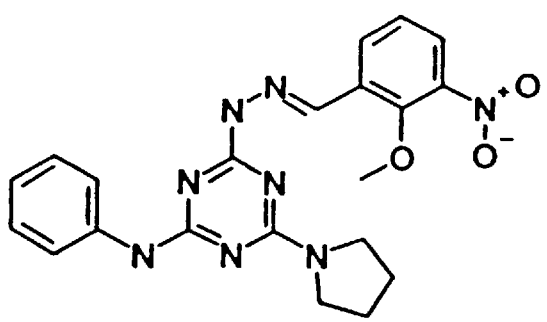
Figure 205:
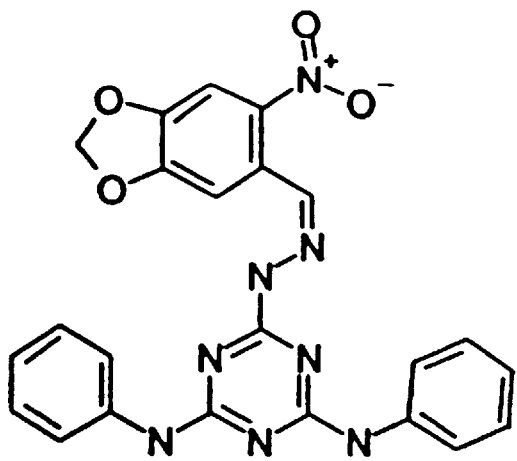
Figure 206:
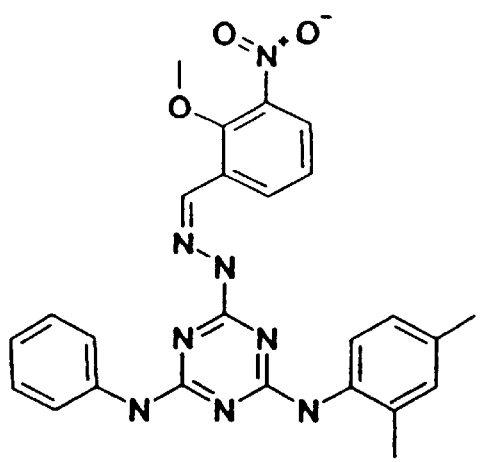
Figure 207:
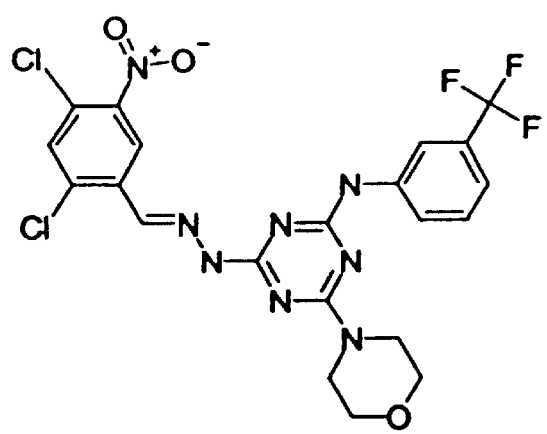
Figure 208:
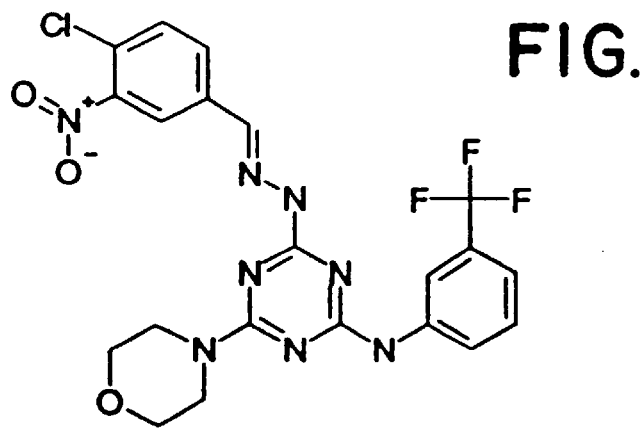
Figure 212:
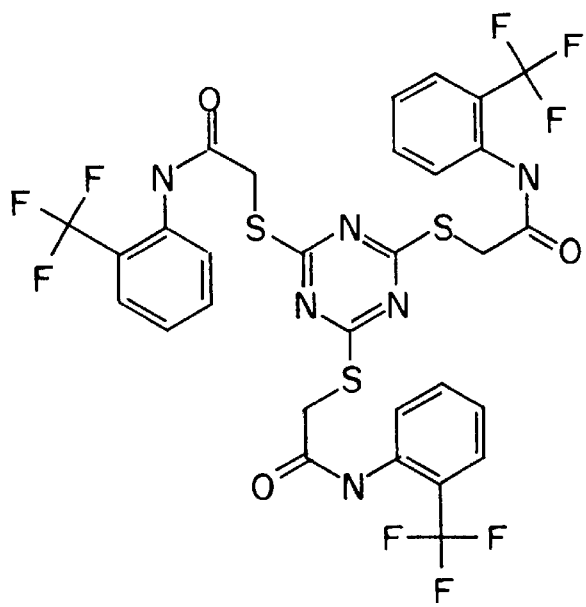
Figure 213:
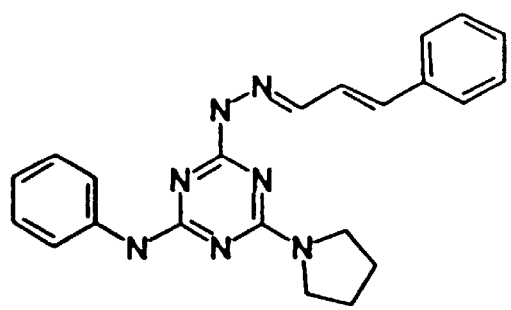
Figure 214:
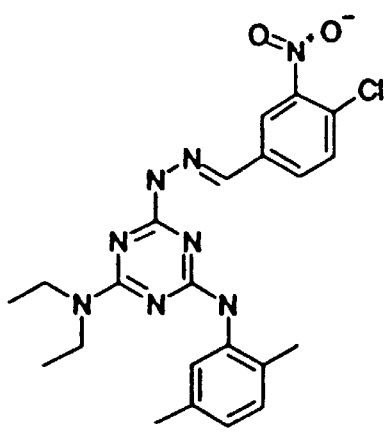
Figure 215:
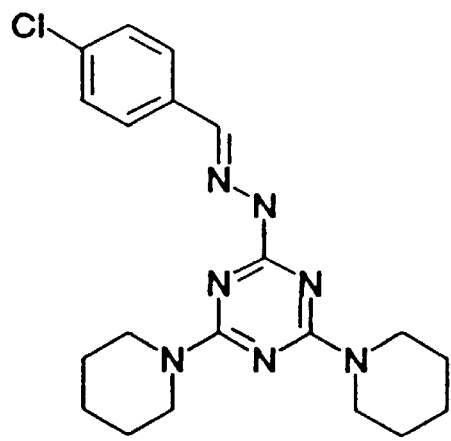
Figure 216:
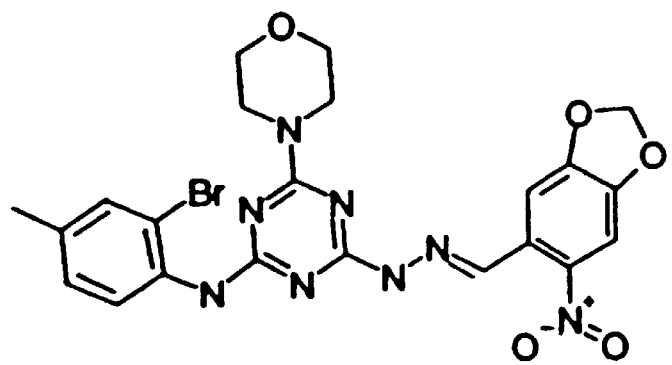
Figure 217:
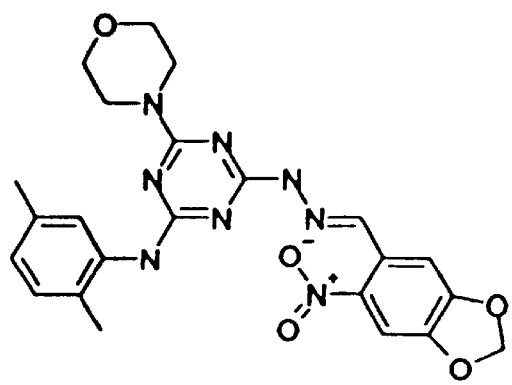
Figure 221:
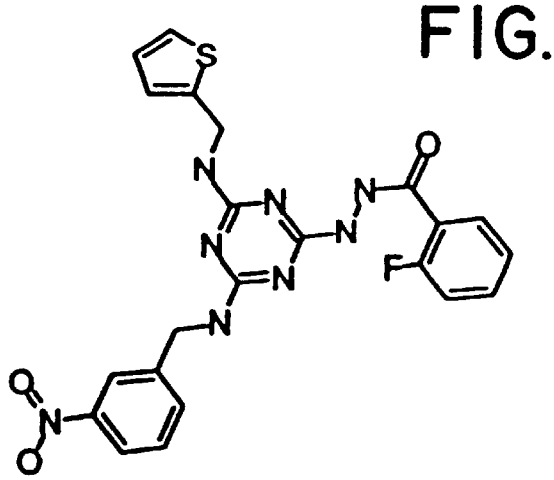
Figure 222:
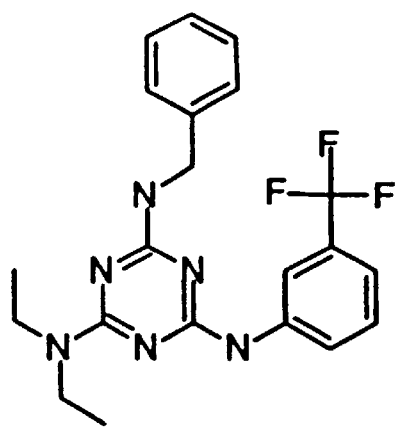
Figure 223:
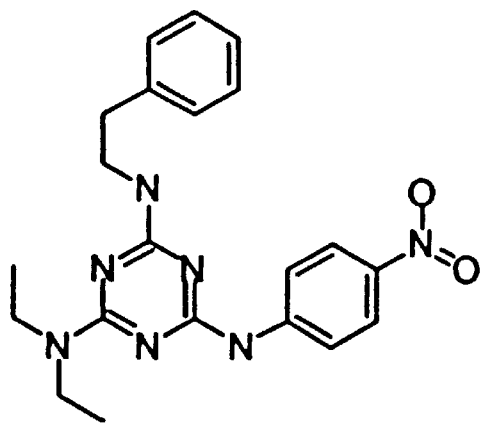
Figure 224:
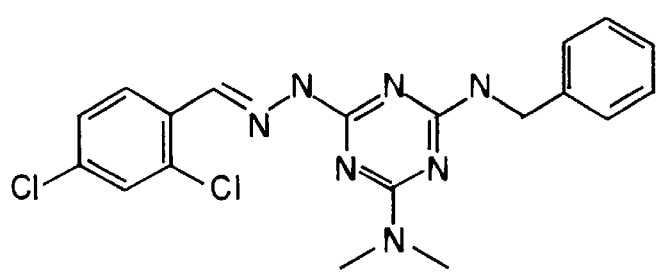
Figure 225:
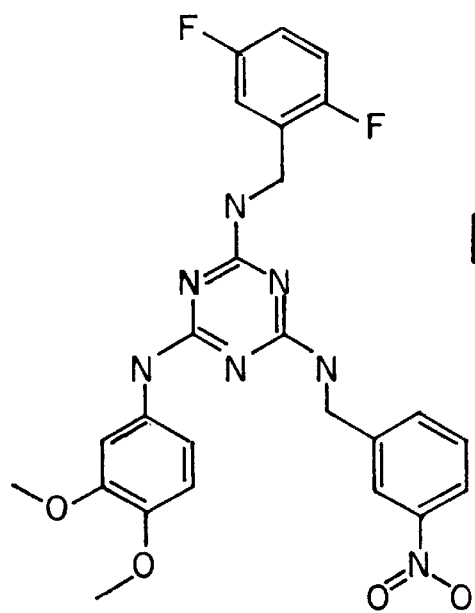
Figure 226:
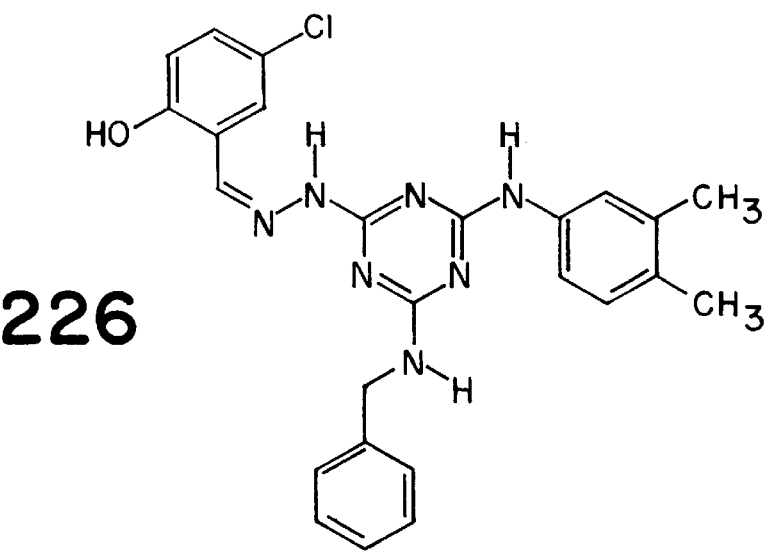
Figure 227:
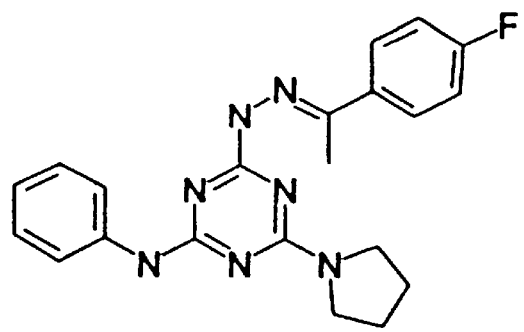
Figure 228:
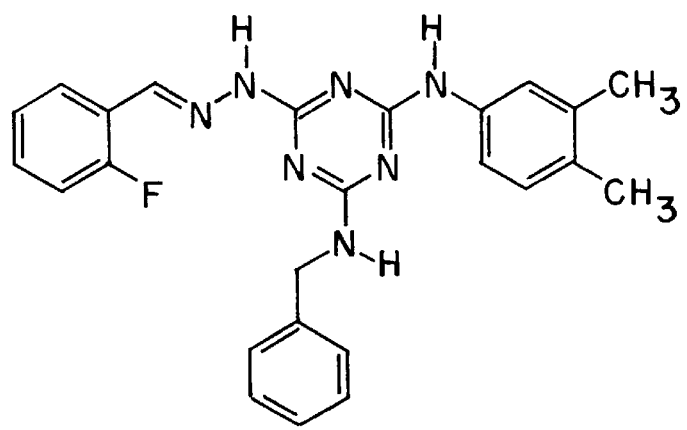
Figure 229:
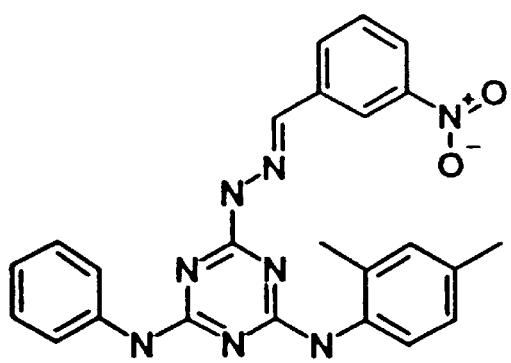
Figure 230:
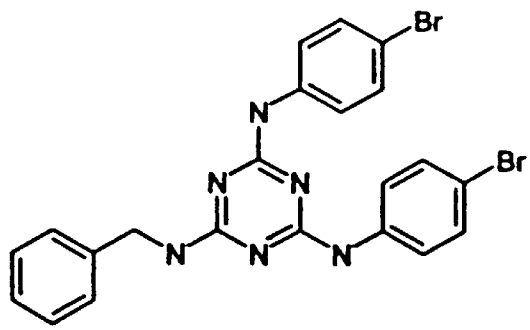
Figure 231:
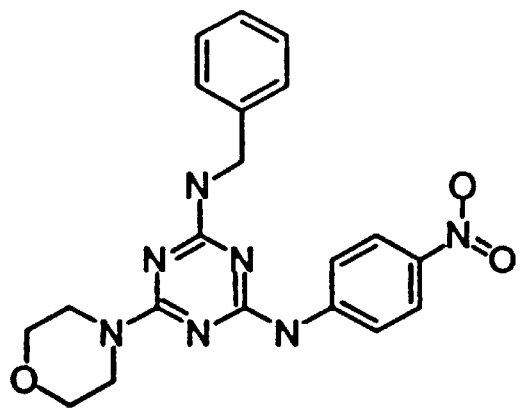
Figure 232:
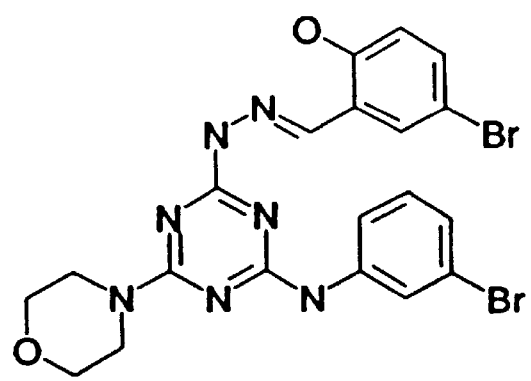
Figure 233:
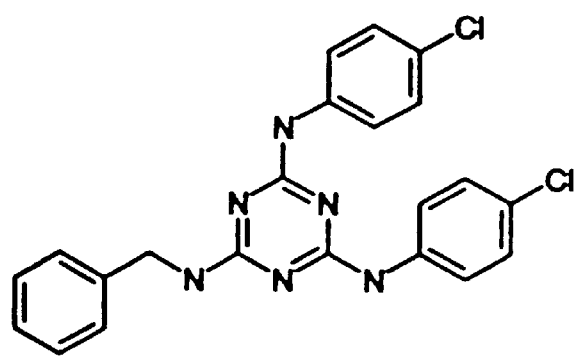
Figure 234:
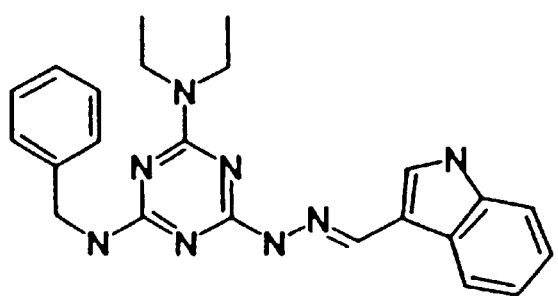
Figure 235:
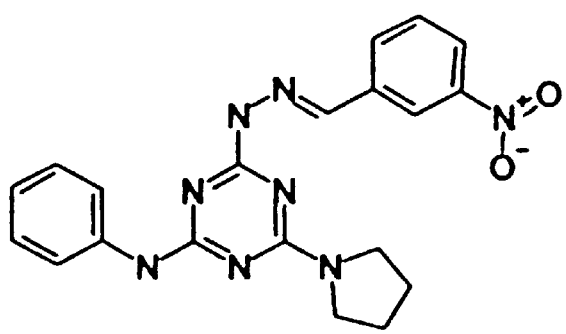
Figure 239:
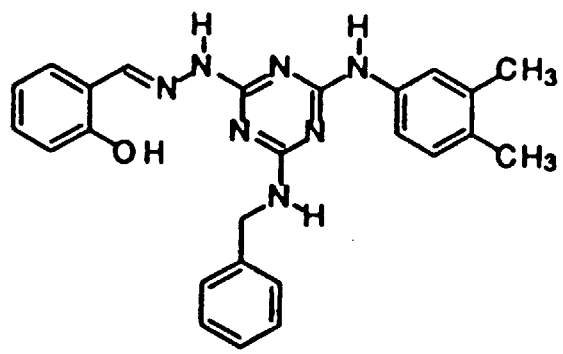
Figure 240:
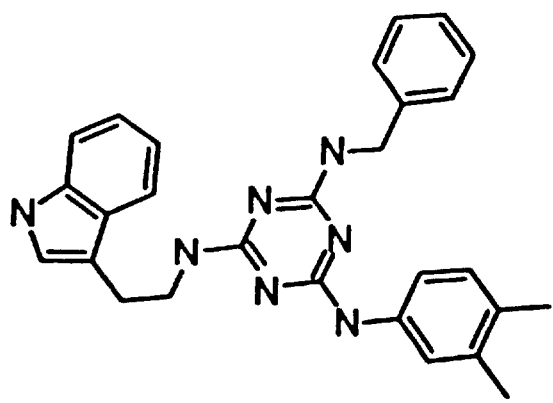
Figure 241:
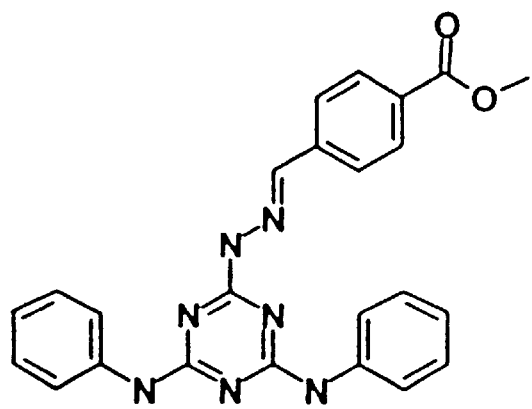
Figure 245:
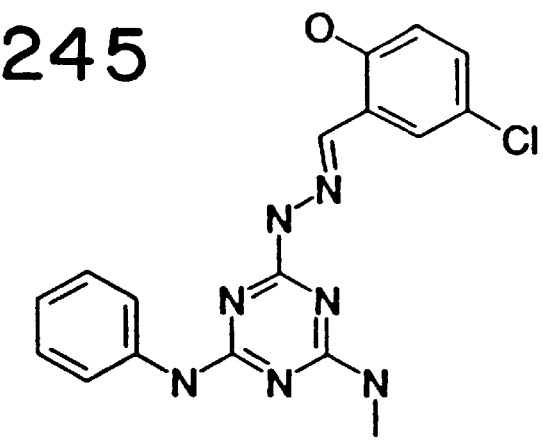
Figure 246:
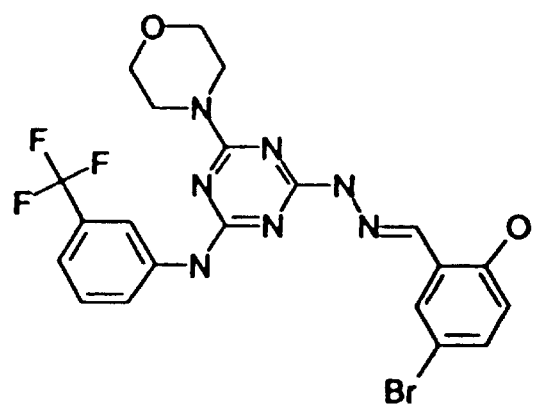

All patent applications, patents, and literature references cited in this specification are hereby incorporated by reference in their entirety. In case of conflict, the present description, including definitions, will prevail.

Definitions

As used herein, the term "ligand" refers to an agent that binds a target RNA. The agent may bind the target RNA when the target RNA is in a native or alternative conformation, or when it is partially or totally unfolded or denatured. According to the present invention, a ligand can be an agent that binds anywhere on the target RNA. Therefore, the ligands of the present invention encompass agents that in and of themselves may have no apparent biological function beyond their ability to bind to the target RNA.

As used herein, the term "test ligand" refers to an agent, comprising a compound, molecule, or complex, which is being tested for its ability to bind to a target RNA.

As used herein, the term "target RNA" refers to a RNA sequence for which identification of a ligand or binding partner is desired. Target RNAs include without limitation sequences known or believed to be involved in the etiology of a given disease, condition or pathophysiological state, or in the regulation of physiological function. Target RNAs may be derived from any living organism, such as a vertebrate, particularly a mammal and even more particularly a human, or from a virus, bacterium, fungus, protozoan, parasite or bacteriophage. Target RNAs may comprise wild type sequences, or, alternatively, mutant or variant sequences, including those with altered stability, activity, or other variant properties, or hybrid sequences to which heterologous sequences have been added. Furthermore, target RNA as used herein includes RNA that has been chemically modified, such as, for example, by conjugation of biotin, peptides, modified bases, fluorescent molecules, and the like.

Target RNA sequences for use in the present invention are typically between about 5 and about 500 nt, preferably between about 30 and about 100 nt, and most preferably about 50 nt. Target RNAs may be isolated from native sources, or, more preferably, are synthesized in vitro using conventional polymerase-directed cell-free systems such as those employing T7 RNA polymerase. In a preferred embodiment, the target RNA is HBV εRNA. FIG. 255A shows the actual portion of the HBV pregenomic sequence that corresponds to the encapsidation signal (εRNA). FIG. 255B shows the εRNA sequence used as target RNA in the method of the present invention, and the RRE RNA target used for specificity tests. The target RNA was prepared by in vitro transcription of a linearized plasmid containing the cloned target sequence, with bacteriophage SP6 RNA polymerase in the presence of $\alpha P^{32}$-UTP to obtain radiolabeled target RNA using methods known to those of ordinary skill in the art.

As used herein, the term "treatment" with regard to a viral or microbial infection includes preventing, retarding, and/or reducing a disease, pathological condition or one or more symptoms thereof, in vertebrates, e.g., birds, and mammals, particularly humans. In the case of HBV, the altering or inhibiting any of the following processes can be considered very useful for the treatment of infection mediated by HBV. They are:

1. Symptoms associated with acute hepatitis, including the onset of the prodromal phase, which is accompanied by anorexia, malaise, nausea and vomiting, and often fever, and which is followed in the icteric phase by the occurrence of urticarial eruptions, arthralgias and jaundice;
2. Elevations in serum aminotransferase and urinary bile levels prior to and during the onset of maximal jaundice;
3. Low-normal white blood cell counts, and appearance on blood smears of atypical lymphocytes; or
4. Symptoms associated with chronic hepatitis infection, including viremia, seroconversion, liver cancer, and cirrhosis.

According to the present invention, treatment constitutes any improvement in one or more clinical or histological symptoms or diagnostic markers observed by the attending physician or determined by quantitative or semiquantitative techniques. Non-limiting examples of appropriate techniques include analysis of blood and urine.

As used herein, "inhibition of replication" refers to any detectable reduction in replication or growth of virus, bacteria or fungi, e.g. between about 1% and about 100% reduction, preferably between about 5% and about 100% reduction, and more preferably between about 10% and about 100% reduction. The skilled artisan will appreciate that any reduction in viral replication, bacterial or fungal growth is significant where it is approximately equal to or greater than that which is observed for known inhibitors of viral replication, bacterial or fungal growth.

As used herein, the terms "antibiotic", "antibacterial" and "antifungal" refer to any compound that inhibits growth of or destroys microorganisms, bacteria, or fungi.

As used herein, the term "aryl" means an aromatic carbocyclic ring system having a single radical containing about 6 to about 10 carbon atoms. An aryl group may be a fused or polycyclic ring system. Exemplary aryl groups include phenyl or napthyl.

As used herein, the term "aryloxy" means an O-aryl group. An aryloxy group is optionally substituted on the aryl moiety of the aryloxy. Suitable substituents include halogen, hydroxy, alkyl, nitro, trihalomethyl, aryl, aryloxy, alkoxy, amino, carbonyl, carboxyl, ester, amide, primary, secondary or tertiary amines, cyano, cycloalkyl, alkenyl, cycloalkenyl and alkynyl.

As used herein, the term "alkyl" means a straight or branched saturated hydrocarbon group. Preferred alkyl groups include those having from 1–12 carbon atoms.

As used herein, the term "cycloalkyl" means a nonaromatic monocyclic or fused or polycyclic ring system of about 3 to about 10 ring carbon atoms. Optionally one or more of the ring carbon atoms of the cycloalkyl may be replaced by a heteroatom, such as nitrogen, oxygen or sulfur. Exemplary cycloalkyl groups include cyclohexyl.

As used herein, the term "cycloalkenyl" means a nonaromatic monocyclic or fused or polycyclic ring system containing a carbon-carbon double bond and having about 3 to about 10 ring carbon atoms. Optionally one or more of the ring carbon atoms of the cycloalkyl may be replaced by a heteroatom, such as nitrogen, oxygen or sulfur.

As used herein, the term "carbonyl" or "carbonyl moiety" refers to any chemical moiety comprising a carbonyl functional group, e.g., a ketone, aldehyde, carboxylic acid, acid halide, amide, peptide, anhydride and ester. As used herein, when a ring structure is described as substituted with a carbonyl group, the ring carbon atom is replaced by the group

As used herein, the term "heteroatom" includes nitrogen, oxygen and sulfur, as well as any atom other than a carbon.

As used herein, the term "ring system" refers to an aromatic or non-aromatic carbocyclic compound, in which one or more of the ring carbon atoms may be replaced by a heteroatom, such as nitrogen, oxygen or sulfur. The ring system may be optionally substituted by one or more halogens, $C_1$ to $C_{12}$ alkyl, aryl, vinyl, alkyl(aryl), vinyl(aryl) and nitro groups.

As used herein, the term "fused ring system" refers to ring systems wherein at least two adjacent carbon centers join one or more cyclic structures. A fused ring system as used herein may be aromatic or non-aromatic, or may be composed of separate aromatic and non-aromatic moieties. Exemplary carbocyclic fused ring systems are represented by the formulas:

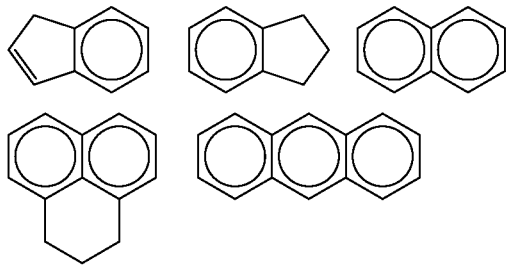

Exemplary fused ring systems in which one or more of the ring carbon atoms is replaced by a heteroatom include the following:

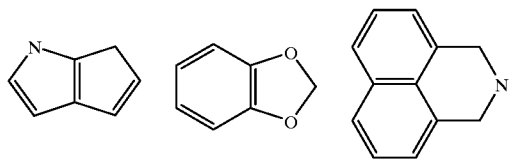

As used herein, the term "polycyclic ring system" refers to ring systems having two or more cyclic compounds bonded in tandem. A polycyclic ring system as used herein may be aromatic or non-aromatic, or may be composed of separate aromatic and non-aromatic moieties. An exemplary carbocyclic polycyclic ring system is represented by the formula

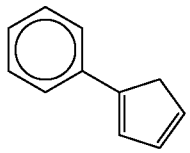

An exemplary polycyclic ring system in which one or more of the ring carbon atoms is replaced by a heteroatom include the following:

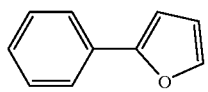

Additionally, fused or polycyclic ring systems may optionally be substituted by one or more halogens, $C_1$ to $C_{12}$ alkyl, aryl, vinyl, alkyl(aryl), vinyl(aryl) and nitro groups.

As used herein, the term "heteroaryl" means an about 5 to 10-membered aromatic monocyclic or fused or polycyclic ring system having a single radical in which one or more of the carbon atoms in the ring system is other than carbon, for example, nitrogen, oxygen or sulfur. An exemplary heteroaryl group is pyridine. An exemplary fused or polycyclic heteroaryl group is indole.

As used herein, the term "heterocyclyl" or "heterocyclic" means an aromatic or non-aromatic about 5 to about 10-membered monocyclic or fused or polycyclic ring system in which one or more of the carbon atoms in the ring system is other than carbon, for example, nitrogen, oxygen or sulfur. A heterocyclyl group may be a fused or polycyclic ring system. Exemplary heterocyclyl groups include piperidine, morpholino, and azepanyl.

As used herein, the term "primary, secondary, or tertiary amine" refers to amine compounds having one, two, or three functional groups, respectively. Suitable functional groups include halogens, amines, $C_1$ to $C_{12}$ alkyl groups, aryl, vinyl, alkyl(aryl), vinyl(aryl) and nitro groups.

As used herein, the term "amide" refers to groups having the amide functional group —C(O)NH—, wherein alkyl, alkenyl or alkynyl groups may be bonded to the C or N atom of the amide group.

As used herein, the term "high affinity" refers to a compound that binds tightly to its target. Preferred compounds of the present invention will exhibit an $IC_{50}$ at or below 50 $\mu$M, preferably at or below 10 $\mu$M, and more preferably at or below 1 $\mu$M.

As used herein, the term "specificity" refers to a compound having either high or low affinity for its target. A highly specific compound will be unaffected by competitor RNA and will not have an effect on a heterologous assay using a different target, independent of the compound's affinity. In a preferred embodiment, compounds of the present invention will exhibit no activity or at least a 5-fold higher $IC_{50}$ value in a heterologous assay than in a specific assay.

The present invention provides methods for inhibiting the replication of viruses and microorganisms and for preventing or treating viral or microbial infection, which comprise administering 1,3,5-triazine compounds and pharmaceutically acceptable salts thereof. The compounds bind Hepatitis B virus (HBV) εRNA with high affinity and specificity, and thereby alter its function. The formulations of the invention comprise triazine derivatives represented by the formulae IA

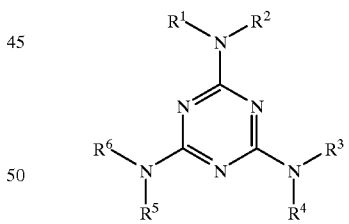

or IB

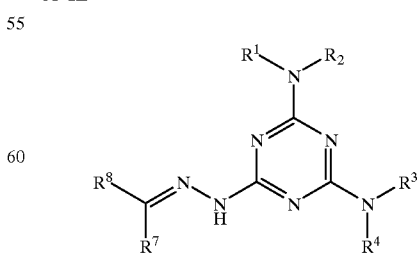

wherein $R^1$, $R^2$, $R^3$, $R^4$, $R^5$, $R^6$, $R^7$ and $R^8$ are each independently selected from the group consisting of hydrogen, alkyl, alkenyl, alkynyl, aryl, heteroaryl, non-aromatic heterocyclic, fused or polycyclic ring and aryloxy;

wherein said alkyl, alkenyl or alkynyl is optionally substituted with one or more substituents selected from the group consisting of halogen, hydroxy, alkyl, nitro, trihalomethyl, aryl, aryloxy, alkoxy, amino, carbonyl, carboxyl, ester, amide, primary, secondary or tertiary amines, cyano, cycloalkyl, alkenyl, cycloalkenyl or alkynyl; and wherein said aryl, aryloxy, heteroaryl, non-aromatic heterocyclic or fused or polycyclic ring is optionally substituted by one or more substituents selected from the group consisting of halogen, hydroxy, alkyl, nitro, trihalomethyl, aryl, aryloxy, alkoxy, amino, carbonyl, carboxyl, ester, amide, primary, secondary or tertiary amines, cyano, cycloalkyl, alkenyl, cycloalkenyl or alkynyl;

or wherein $R^1$ and $R^2$ together, $R^3$ and $R^4$ together, or $R^5$ and $R^6$ together, optionally form a cycloalkyl, cycloalkenyl, non-aromatic heterocyclic, heteroaryl, or fused or polycyclic ring, said cycloalkyl, cycloalkenyl, non-aromatic heterocyclic, heteroaryl, or fused or polycyclic ring optionally substituted with one or more substituents selected from the group consisting of halogen, hydroxy, alkyl, nitro, trihalomethyl, aryl, aryloxy, alkoxy, amino, carbonyl, carboxyl, ester, amide, primary, secondary or tertiary amines, cyano, cycloalkyl, alkenyl, cycloalkenyl and alkynyl;

or wherein $R^7$ and $R^8$ together optionally form a cycloalkyl, cycloalkenyl, non-aromatic heterocyclic or fused or polycyclic ring, wherein said cycloalkyl, cycloalkenyl and non-aromatic heterocyclic or fused or polycyclic ring are optionally substituted with one or more substituents selected from the group consisting of halogen, hydroxy, alkyl, nitro, trihalomethyl, aryl, aryloxy, alkoxy, amino, carbonyl, carboxyl, ester, amide, primary, secondary or tertiary amines, cyano, cycloalkyl, alkenyl, cycloalkenyl and alkynyl, with the proviso that when $R^7$ and $R^8$ together form a fused or polycyclic ring, the moiety of the fused or polycyclic ring that binds with N is non-aromatic;

and pharmaceutically acceptable salts thereof;
and a pharmaceutically acceptable carrier or diluent.

In one embodiment, the invention is directed to compounds of formula IB wherein one or $R^1$ and $R^2$ is an optionally substituted aryl. In another embodiment, the invention is directed to compounds of formula IB wherein one of $R^7$ or $R^8$ is an optionally substituted aryl.

Non-limiting examples of the compounds of the invention include:

II
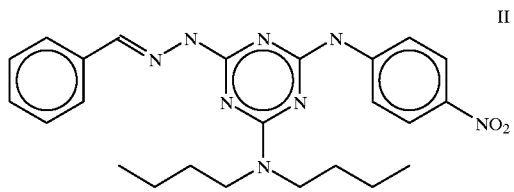

III
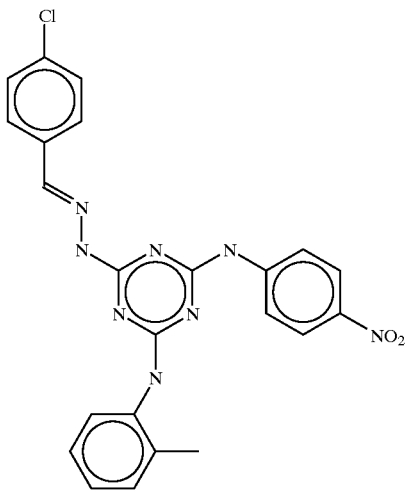

IV
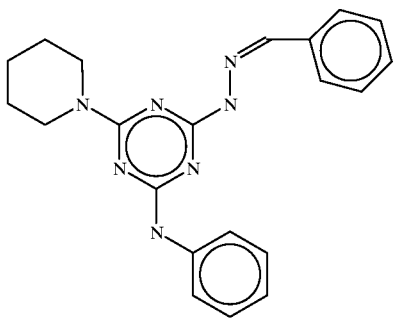

V
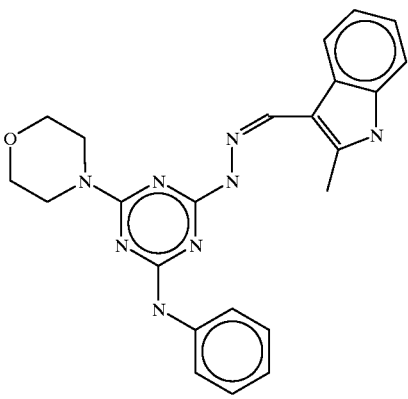

VI
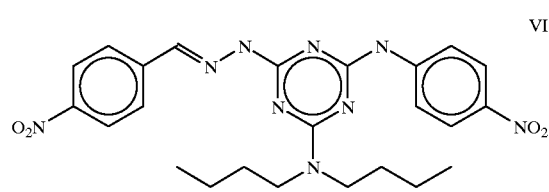

-continued

VII

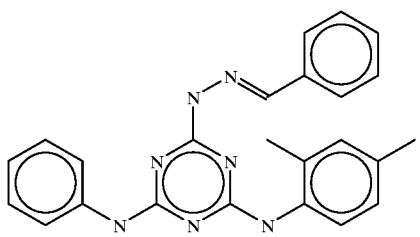

The following is a chemical process for the efficient production of triazines of the formula IA:

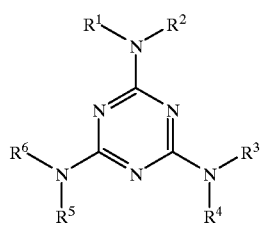

or IB

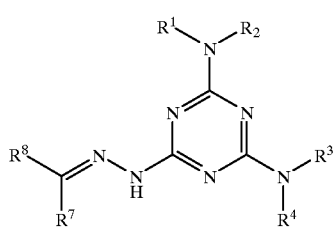

Commercially available cyanuric chloride (IX) is first reacted with two equivalents of a reagent chosen from a group consisting of a primary amine and a secondary amine, to afford a singly substituted triazine of the formula (X).

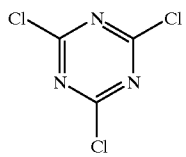 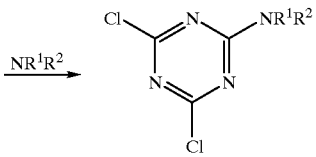

Fig. IX                Fig. X

The 2-amino 4,6 di chloro-1,3,5 triazine of the formula (X) is then reacted with two equivalents of a reagent chosen from a group consisting of a primary amine and secondary amine to afford a disubstituted triazine of the formula (XI)

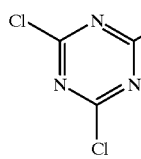 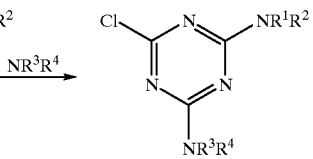

Fig. X                Fig. XI

The 2,4-diamino-6-chloro-1,3,5 triazine of the formula (XI) can then be reacted with two equivalents of a reagent chosen from a group consisting of a primary amine, secondary amine, and hydrazine. In the case of a primary and secondary amine, the reaction affords a trisubstituted triazine of the formula (XII).

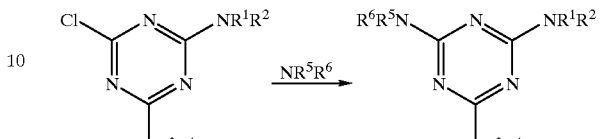

Fig. XI                Fig. XII

In the case of hydrazine, condensation reaction forms compound (XIII).

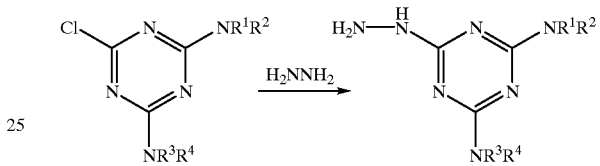

Fig. XI                Fig. XIII

Compound (XII) can then be further reacted with a reagent chosen from a group consisting of aldehydes and ketones to afford 2,4,6- substituted-1,3,5-triazines of the formula (XIV).

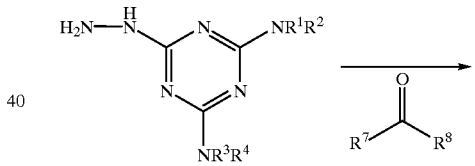

Fig. XIII

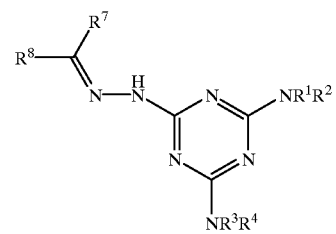

Fig. XIV

DETAILED DESCRIPTION OF THE PREFERRED EMBODIMENTS

The following is a chemical process for the efficient production of triazine derivatives:

Example 1

2-fluorobenzaldehyde N-[4-(benzylamino)-6-(tert-butylamino)-1,3,5-triazin-2-yl]hydrazone (compound 93)

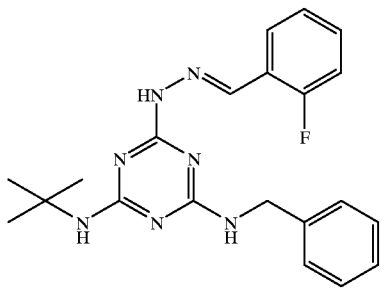

Step 1

To a stirred solution of cyanuric chloride in DME at −30° C. was added a solution of 2 equivalents of benzylamine in water in dropwise fashion. The mixture was then stirred for 3 hrs. at the reduced temperature, after which time the mixture was warmed to room temperature and washed sequentially with saturated sodium bicarbonate and water, dried over magnesium sulfate, and reduced in vacuo. The product was used in the next step without purification.

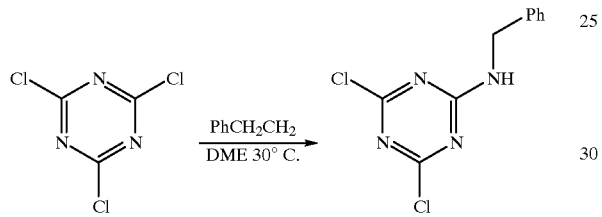

Step 2

To a stirred solution of the product of step 1 in dichloromethane at room temperature was added 2 equivalents of tert-butyl amine in dropwise fashion. The solution was stirred for 12 hrs., after which time the mixture was then washed sequentially with 0.1 M hydrochloric acid, water, and saturated brine, dried over sodium sulfate, reduced in vacuo and recrystallized from hexane:ethyl acetate (4:1) to afford the starting material of step 2.

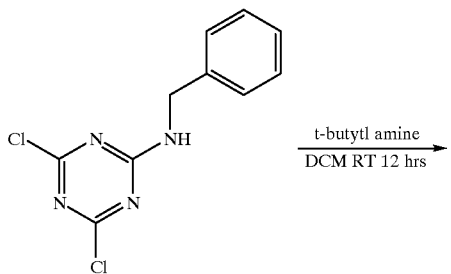

Step 3

To a solution of the product of step 2 in dichloromethane was added 2 equivalents of hydrazine in water in dropwise fashion. The solution was then heated to 60° C. for a period of 12 hrs., after which time the mixture was cooled to room temperature, washed sequentially with brine and water, dried over sodium sulfate and reduced in vacuo to a residue which was then recrystallized from hexane:ethyl acetate (4:1) to afford the starting material of step 4.

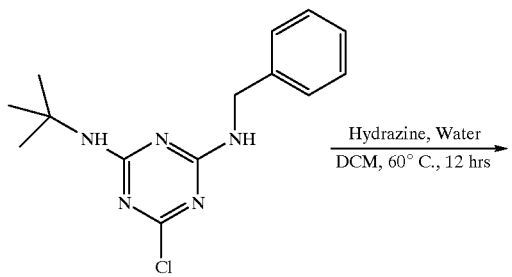

Step 4

To a stirred solution of the product of step 3 in toluene in a round bottom flask was added one equivalent of 2-fluorobenzaldehyde. The flask was then fitted with a Dean Stark trap and refluxed to azeotropically remove water. After which time the removal of water was complete, the solution was cooled to room temperature and the solvent was removed in vacuo. The residue was then recrystallized from hexane:ethyl acetate (5:1) to afford compound 93.

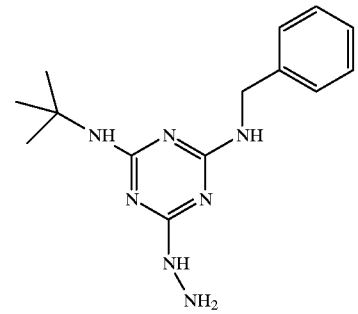

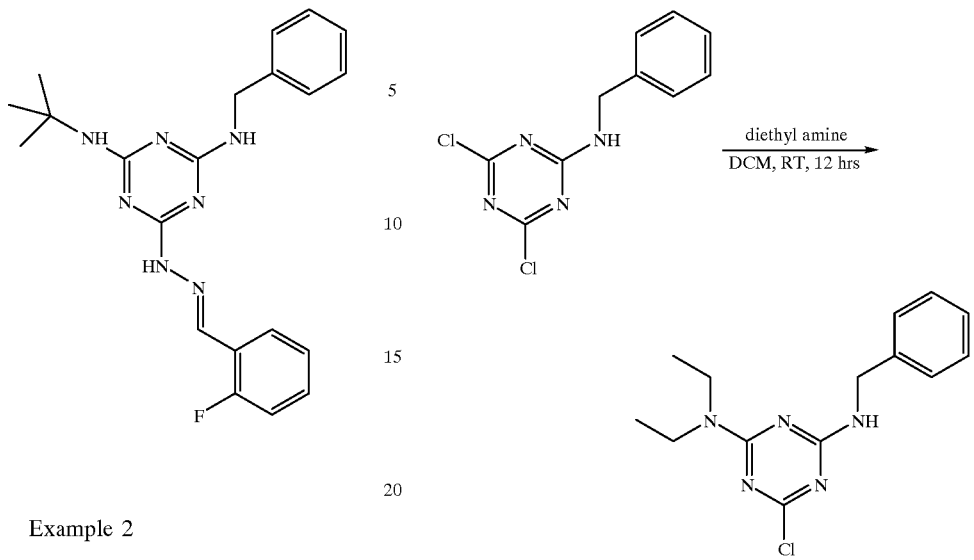

Example 2

2-hydroxybenzaldehyde N-[4-(benzylamino)-6-(diethylamino)-1,3,5-triazin-2-yl]hydrazone (compound 155)

Step 1

To a stirred solution of cyanuric chloride in DME at −30° C. was added a solution of 2 equivalents of benzylamine in water in dropwise fashion. The mixture was then stirred for 3 hrs. at the reduced temperature, after which time the mixture was warmed to room temperature and washed sequentially with saturated sodium bicarbonate and water, dried over magnesium sulfate and reduced in vacuo. The product was used in the next step without purification.

Step 2

To a stirred solution of the product of step 1 in dichloromethane at room temperature was added 2 equivalents of diethyl amine in dropwise fashion. The solution was stirred for 12 hrs., after which time the mixture was then washed sequentially with 0.1 M hydrochloric acid, water and saturated brine, dried over sodium sulfate, reduced in vacuo and recrystallized from hexane:ethyl acetate (4:1) to afford the starting material of step 3.

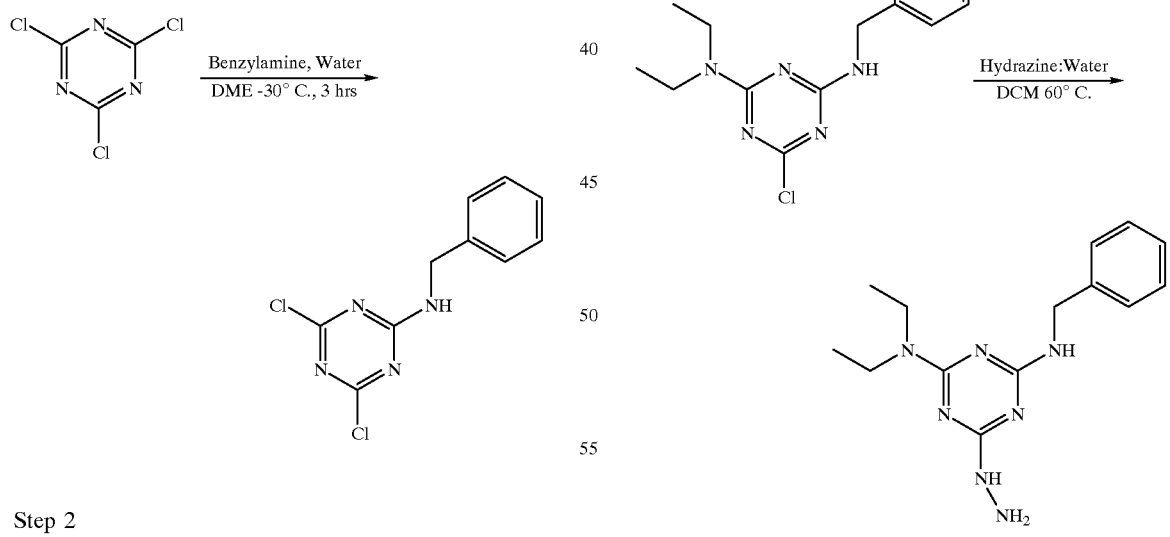

Step 3

To a solution of the product of step 2 in dichloromethane was added 2 equivalents of hydrazine in water in dropwise fashion. The solution was then heated to 60° C. for a period of 12 hrs., after which time the mixture was cooled to room temperature, washed sequentially with brine and water, dried over sodium sulfate and reduced in vacuo to a residue which was then recrystallized from hexane:ethyl acetate (4:1) to afford the starting material of Step 4.

Step 4

To a stirred solution of the product of step 3 in toluene in a round bottom flask was added one equivalent of salicylaldehyde. The flask was then fitted with a Dean Stark trap and refluxed to azeotropically remove water. After which time the removal of water was complete, the solution was cooled to room temperature and the solvent was removed in vacuo.

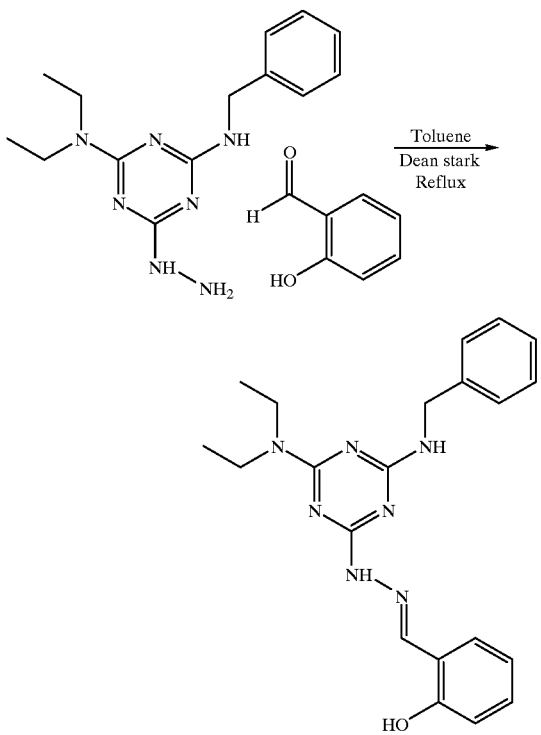

The residue was then recrystallized from hexane:ethyl acetate (5:1) to afford compound 155:

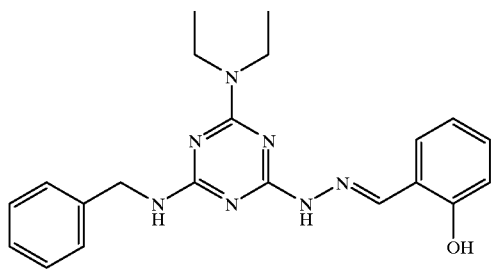

Determination of Antiviral or Antimicrobial Activity

In Vitro Assay

One assay used in determining the activity of the compounds of the present invention is disclosed in copending U.S. patent application Ser. No. 08/709,342, filed Sep. 6, 1996, the disclosure of which is hereby incorporated herein by reference in its entirety. The assay detects the interaction between target RNA molecule and a test ligand by measuring the ligand's ability to inhibit hybridization between the RNA and a specific complementary oligonucleotide. In one embodiment, the target RNA is radiolabelled and the oligonucleotide is labeled with biotin; in this case, the extent of hybridization is determined by measuring the amount of radiolabeled RNA detected with a streptavidin/biotin-based capture system.

Ligands that exhibit inhibitory activity in a primary in vitro assay are then titrated and tested in secondary assays to eliminate false positives. Concentrations of test compounds of between about 0.1 $\mu$M and about 200 $\mu$M are assayed for inhibition using radiolabeled $\epsilon$RNA in the absence or presence of a large excess of an unlabeled non-specific RNA competitor (such as, e.g., ribosomal RNA, rRNA). Compounds that bind $\epsilon$RNA non-specifically are competitively displaced by the rRNA, resulting in reduced or no inhibition of hybridization between the radiolabeled $\epsilon$RNA and the biotinylated oligonucleotide. Conversely, the inhibitory activity of compounds that specifically bind $\epsilon$RNA is not affected by the presence of the competitor rRNA.

Specificity is further tested in a third assay in which the radiolabeled RNA is the HIV derived RRE RNA and the biotinylated oligonucleotide is complementary to RRE. Compounds with high specific activity for $\epsilon$RNA are not expected to be inhibitory in the RRE RNA based assay. The specificity of the ligand for $\epsilon$RNA is expressed as the ratio between the IC$_{50}$ value obtained with the specific target RNA and the IC$_{50}$ value obtained with a heterologous target (RRE RNA), both in the presence of competitor RNA.

The substituted 2,4,6-triamino-1,3,5-triazine derivatives of the present invention preferably exhibit IC$_{50}$ values for their interaction with $\epsilon$RNA at or below 300 $\mu$M, more preferably at or below 50 $\mu$M, and most preferably at or below 5 $\mu$M, in the presence of an excess of non-specific competitor rRNA.

Bioassay

Ligands that exhibit high affinity and specificity for $\epsilon$RNA as determined above are tested for their ability to inhibit HBV replication. Several cell lines and cell culture assays have been developed to identify potential therapeutics effective against chronic HBV infection. One of these cell lines, 2.2.15, has been used in a standardized assay that has repeatedly proven to be an accurate model of chronic cellular HBV replication and a predictive model of antiviral response for chronic hepadnaviral infection in vivo. 2.2.15 cells contain copies of the complete HBV genome integrated into the cell's genome, and 2.2.15 cells are not susceptible to infection by HBV. (Sells, M. A. et al., J. Virol. 62 (8): 2836–2844 (1988)). These cells express HBV genes producing complete HBV particles capable of infecting chimpanzees (Acs, G. et al., Proc. Natl. Acad. Sci. USA 84 (13): 4641–4644 (1987)). Briefly, 2.2.15 cells are cultured and pretreated with a test compound for about 9 days, at which point the media are harvested and subjected to dot-blot hybridization to detect HBV virion DNA.

Further, the antiviral effect of any compound must be measured against its toxicity. Cytotoxicity is measured by the neutral red uptake method using the same cells used for antiviral activity.

It will be understood that the skilled artisan can employ any assay suitable for assessing the inhibitory potency of a compound to practice the present invention without undue experimentation. See, e.g., J. Sambrook and T. Maniatis, "Molecular Cloning: A Laboratory Manual", Cold Spring Harbor Laboratories Press, Cold Spring Harbor, N.Y. (1989), "Current Protocols in Molecular Biology", Ed. F. M Ausubel, et al., J. Wiley & Sons, Inc. 1997, D. Leland, "Clinical Virology", W. B. Saunders Co., 1996, and "Cells: A Laboratory Manual", Ed. D. L. Spector, et al. Cold Spring Harbor Laboratory Press, Cold Spring Harbor, N.Y., 1997.

The compounds of the present invention are believed to inhibit viral or microbial replication by binding to functionally important viral or microbial nucleic acids. The nucleic acids may be RNA or DNA, may form part of the genome of the virus or microorganism or an intermediate thereof, or may represent expressed mRNA species or any other functional nucleic acid unique to the replication or function of the virus or microorganism.

Compounds of the present invention inhibit hybridization of the oligonucleotide probe in the assay described in copending application U.S. patent application Ser. No.

08/709,342, filed Sep. 6, 1996. This indicates that the compounds interact with the RNA target by stabilizing the RNA structure, thereby inhibiting the formation of hybrids between the RNA target and the complementary oligonucleotide present in the assay.

Figure 258B:
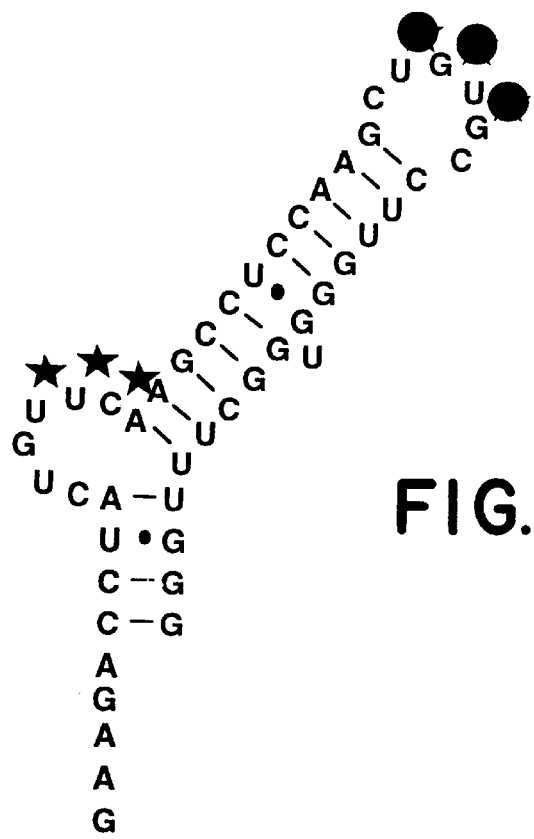
FIGS. 258A and 258B are photographic and schematic representations, respectively, of the results of the reaction of rRNA, εRNA, RNase, and compound 5 at concentrations ranging from 0 and 200 μM.
Figure 258A:
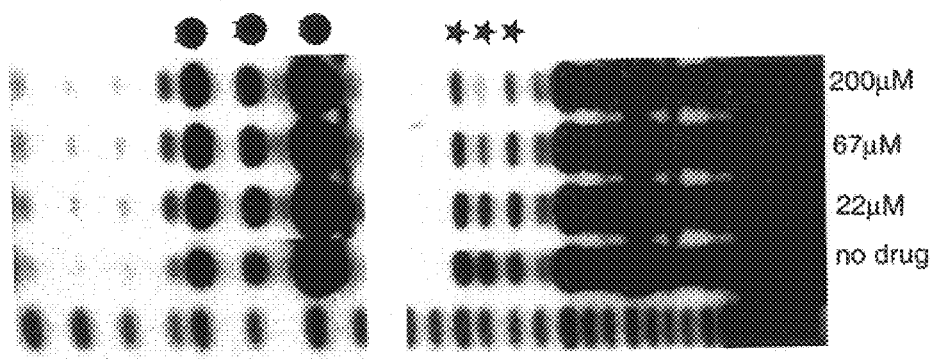

Supplementary evidence in support of the contention that triazine compounds interact with the RNA target came from the observation that compound 5 protects specific positions of RNA from digestion with RNases. RNase protection was assessed by incubating an end-labeled RNA with the amount of RNase needed to yield a ladder representing single cut events at each possible cleavage site in the RNA structure (based upon a gel electrophoresis analysis). The presence of a ligand bound to the RNA renders the binding site inaccessible to the RNases and therefore, the binding site will be shown by the disappearance or weakening of specific bands in the digestion pattern (FIGS. 258A and 258B).

Figure 259B:
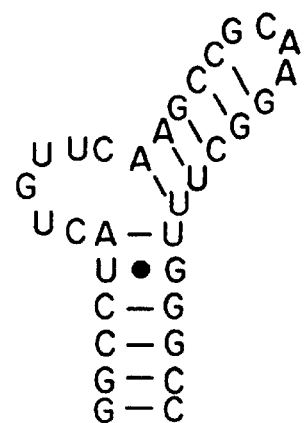

Further, the RNA binding ability of the triazine compounds was demonstrated by preparing an RNA target containing only the bulge region of εRNA. The melting temperature of the RNA was determined by monitoring the change in optical density at 260 nm with increasing temperature. Upon addition of 10 μM of triazine compound, the melting temperature was shifted, which indicates that the RNA structure is stabilized by the ligand (FIGS. 259A and 259B).

Thus, these experiments demonstrate that the triazine compounds interact with the bulge region of εRNA by nucleic acid binding.

The methods and formulations of the invention can be used to inhibit replication and/or prevent or treat infection caused by: hepatitis B virus, hepatitis C virus, herpes simplex virus, types 1 and 2, varicella-zoster, cytomegalovirus, Epstein-Barr virus, polyomavirus, papillomavirus, parvovirus, vaccinia virus, molluscum contagiosum, Marburg and Ebola viruses, influenza A and B, measles, mumps, respiratory syncytial virus, poliovirus, coxsackie virus A and B, rhinovirus, rotavirus, human immunodeficiency virus, types 1 and 2, rabies, rubella, and equine encephalitis. DNA and RNA viruses encompassed by the invention, include, without limitation, viruses belonging to the viral families adenoviridae, hepadnaviridae, herpesviridae, papovaviridae, parvoviridae, poxviridae, arenaviridae, bunyaviridae, flaviviridae, orthomyxoviridae, paramyxoviridae, picornaviridae, reoviridae, retroviridae and rhabdoviridae.

Accordingly, compounds and formulations of the present invention can be used in the prevention and treatment of viral hepatitis caused by HBV, as well as in the prevention and treatment of disease conditions associated with other DNA and RNA viruses. Such conditions include, but are not limited to: upper and lower respiratory tract infections, ocular infections, gastroenteritis, cystidis, and complications arising in transplant recipients, each of which is associated with adenoviruses; treatment of immunocompromised individuals, wherein a compromised immune system is associated with cytomegalovirus; infectious mononucleosis, associated with Epstein-Barr virus; chickenpox and shingles, which are associated with varicella-zoster; oral, genital and skin lesions, as well as various dermatological anomalies associated with herpesvirus, papillomavirus and polyomavirus; smallpox, as well as complications arising from smallpox vaccinations, including allergic rash, progressive vaccinia and postvaccinial encephalitis, each of which being associated with variola, molluscum and contagiosum; hemorrhagic fever and aseptic meningitis, which are associated with lassa fever virus, lymphocytic choriomeningitis virus and other arenaviruses; upper and lower respiratory infections, serious acute respiratory tract illness and pneumonia associated with influenza A, B, and C; measles, mumps, and parainfluenza, associated with paramyxoviruses; enteric, neuromuscular and central nervous system infections associated with picornaviruses; acquired immune deficiency syndrome (AIDS) and associated infections and clinical syndromes associated with HIV infection; and encephalitis and measles associated with togaviruses.

Moreover, given the functional similarities of the compounds of the present invention and other RNA binding molecules, e.g., neomycin, erythromycin and aminoglycosides, the compounds and compositions of the present invention can be used as antibiotic therapies. Antibiotics are used in the treatment of infectious diseases in plants, animals and man, and may kill and/or inhibit the growth of microorganisms. Therefore, the compounds and compositions of the present invention may be used as bacteriocidal, bacteriostatic and broad-spectrum antibiotic agents.

Pharmaceutical Formulations

The compositions of the present invention can be administered in dosages and by techniques well known to those skilled in the medical, veterinary, and agricultural arts taking into consideration such factors as the age, sex, weight, species and condition of the particular patient, and the route of administration. The compositions of the present invention can be administered alone, or can be co-administered or sequentially administered with additional, non-triazine based antiviral agents, such as, e.g., Acyclovir, α-interferon, ribavirin, and various protease inhibitors, e.g., ritonavir, indinavir, saquinavir, and/or additional non-triazine based antibiotics, such as, e.g., erythromycin, gentamycin, nanamycin, and streptomycin.

Figure 257B:
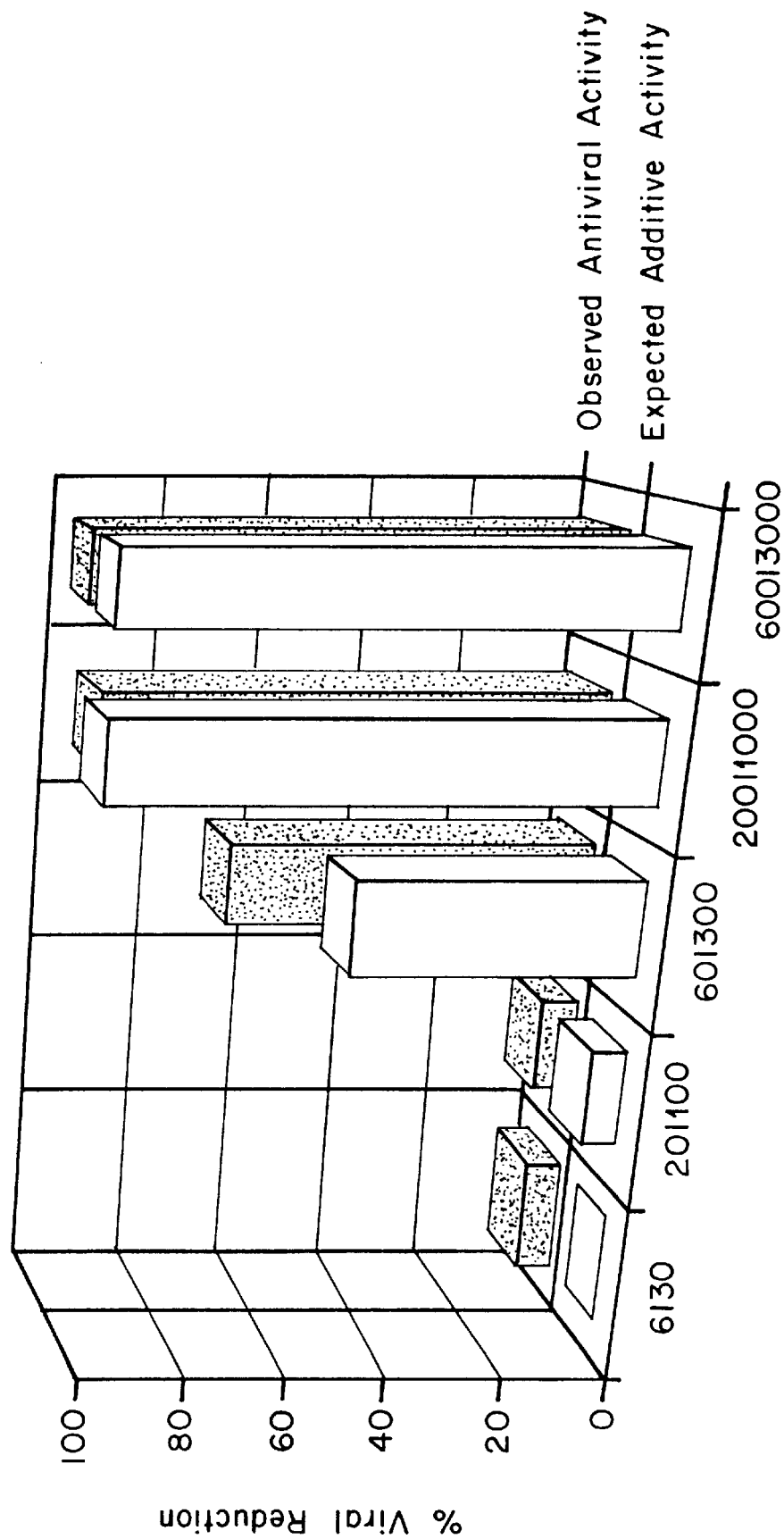

The effect of simultaneous administration of triazine compound 5 and 2'-deoxy-3'-thiacytidine, a well known nucleoside analog having antiviral activity, was examined in order to assess the interaction between the two therapies. The results show a strong synergistic interaction when the two drugs are administered together at a 1:15 molar ratio (3TC: triazine; FIG. 257A). The antiviral activity observed with the combination drug treatment is larger than the additive activity expected based on the activities of each compound administered alone. A synergistic response allows the use of lower amounts of each drug in combination therapies, which reduces the toxicity and secondary risks. Moreover, combination therapies with drugs acting on different targets should reduce the probability that drug resistant viral strains will develop.

Moreover, the formulations of the present invention can be administered in a formulation suitable for the manner of administration, including but not limited to liquid preparations for mucosal administration, e.g., oral, nasal, anal, vaginal, peroral, intragastric administration and the like, such as solutions, suspensions, syrups, elixirs. Further, liquid preparations for administration of the compositions of the present invention for parenteral, subcutaneous, intradermal, intramuscular, intravenous administrations, and the like, such as sterile solutions, suspensions or emulsions, e.g, for administration by injection, can be formulated without undue experimentation. Oral administration is presently preferred.

In order for a composition to be administered to an animal or human, and for any particular method of administration, it is preferred to determine the toxicity, such as by determining the lethal dose (LD) and $LD_{50}$ in a suitable animal model, e.g., mouse; the dosage of the composition(s), and the concentration of components in the composition; and the timing of administration in order to maximize the antiviral and/or antimicrobial response. Such factors can be determined without undue experimentation by such methods as titrations and analysis of sera for antibodies or antigens, e.g., by ELISA and/or EFFIT analysis. Such determinations do not require undue experimentation from the knowledge of the skilled artisan, the present disclosure and the documents cited herein.

The formulations can be administered in a pharmaceutically effective amount, an antiviral effective amount and/or in an antimicrobial effective amount, taking into account such factors as the relative activity and toxicity for the target indication, e.g., antiviral activity and/or antimicrobial activity, as well as the route of administration, and the age, sex, weight, species and condition of the particular patient.

The compositions of the present invention can be solutions, suspensions, emulsions, syrups, elixirs, capsules, tablets, and the like. The compositions may contain a suitable carrier, diluent, or excipient, such as sterile water, physiological saline, glucose, or the like. Moreover, the compositions can also be lyophilized, and/or may contain auxiliary substances, such as wetting or emulsifying agents, pH buffering agents, adjuvants, gelling or viscosity enhancing additives, preservatives, flavoring agents, colors, and the like, depending upon the route of administration and the preparation desired. Standard texts, such as "Remington's Pharmaceutical Science", 17th Ed., 1985, incorporated herein by reference, may be consulted to prepare suitable preparations, without undue experimentation.

Suitable dosages for compositions of the present invention can be determined without undue experimentation based upon the Examples provided below, and the documents cited herein. For instance, suitable dosages of antiviral and/or antibiotic agent in a composition can be 0.1 to 250 mg/kg/day, preferably below 100 mg/kg/day, and most preferably below 50 mg/kg/day.

In a further embodiment, the compounds of the present invention can be used as lead compounds to improve the antiviral and/or antibiotic activities of the compounds. This can be done by modifying certain functional groups of the compounds of the present invention based upon a recognition of the structure/activity relationship between a particular functional group in a compound and its biological activity. Such modifications include synthetic manipulation of the size, hydrophilicity, hydrophobicity, acidity and basicity of a functional group, which may inhibit or enhance the activity of a compound.

Moreover, based upon the observed binding interaction between the compounds of the present invention and nucleic acids, the compounds of the present invention can be used in a method of detecting and/or purification of nucleic acids, e.g. binding assays and affinity chromatography. For example, the compounds of the invention can be covalently attached to a chromatographic support and a nucleic acid-containing solution can be eluted over the solid support, which will bind the target nucleic acid as the other components of the solution elute from the column in the flow-through. With regard to binding assays and affinity chromatography, reference is made to A. Fersht, *Enzyme Structure and Mechanism*, 2d Ed., W. H. Freeman & Co., New York, 1985, and R. K. Scopes, *Protein Purification, Principles and Practice* 2d Ed., Springer-Verlag, New York, 1987, the disclosures of which are hereby incorporated herein by reference.

Additionally, the compounds of the present invention could be used as inhibitors of specific steps of the viral replication cycle in order to study the process in vivo or in vitro. In a diagnostic application, the compound could be used for detection of specific RNA species in samples by using a triazine derivative labeled with a fluorescent, immunochemical, or radioactive moiety. Further, such labeled triazine compounds could be used to study intracellular localization of the RNA target by electron-microscopy or light microscopy using tissue culture preparations.

The following examples are intended to further illustrate the invention without imposing any undue limitations thereon.

Example 1
High-Throughput Identification of εRNA Ligands

Compounds of the invention were obtained from commercial sources. Compound 32 is available from MicroSource Discovery Systems, Inc., Gaylordsville, Conn.; compounds 64, 136, and 148 are available from ComGenex, Inc., Budapest, Hungary; compounds 103 and 123 are available from ChemBridge Corp., San Diego, Calif.; and the remaining compounds are available from Specs and Biospecs B. V., Rijswljk, The Netherlands.

The high throughput assays were performed in 96-well plates containing eighty drugs (5 μl, 60 μg/ml in DMSO) distributed one per well in columns 2–6 and 8–12 of the 8×12 96-well array. The remaining 16 wells in columns 1 and 7 were filled with 5 μl DMSO to serve as the control reactions. 45 μl of reaction mixture containing buffer, salts and radiolabeled target RNA were delivered on each well of the compound-containing plates to yield a 50 μl mixture containing 50 mM Tris-HCl, pH 7.5, 200 mM KCl, 5 mM MgCl$_2$, 5 mM DTT, 6 μg/ml test compound, and 25 nM [$^{32}$P]-labeled εRNA. The reaction was started by addition of the biotinylated oligonucleotide, 262.104 A (5 μl) to a final concentration of 100 nM. The reaction was incubated at 25° C. for 60 minutes, and then 5 μl of 0.3 mg/ml SAAP (streptavidin alkaline phosphatase conjugate, Pierce, Rockford, Ill.) was added. The reaction was incubated for an additional 30 minutes at 25° C. and filtered through 96-well format HATF nitrocellulose filters (Millipore, Bedford, Mass.) using a multiscreen vacuum manifold (Millipore, Bedford, Mass.). Subsequently, 300 μl of wash buffer (50 mM Tris-HCl, pH 7.5, 200 mM KCl) was filtered through to wash the filters. The filters were dried and supplemented with 20 μl scintillation fluid (Super Mix, Wallac Oy, Turku, Finland). The amount of hybrids formed was determined by scintillation counting of the radiolabeled εRNA retained on the filters.

The inhibitory effect of a test compound (expressed as percentage of inhibition, % Inh.) was calculated using the following formula:

$$\% \ Inh. = (1-(Rx/Ro)) \times 100$$

where Ro is the average retention of hybrids in the 16 identical control reactions in columns 1 and 7 and Rx is the hybrids retained in the presence of a test drug, x.

Biotinylated oligonucleotides 262.104 A (5'-biotin-TTA GGC ACA GCT TGG AGG CTT GAA CAG TG-3') and 208.92 A (5'-biotin-CGT CAT TGA CGC TGC GCC CA-3') were synthetically prepared (Oligos Etc., Willsonville, Oreg.). These oligonucleotides are complementary to regions of the εRNA and RRE RNA targets, respectively.

A plasmid containing the target sequence following the bacteriophage SP6 promoter was used as a template for the synthesis of radiolabeled εRNA using [α$^{32}$ P]-UTP and SP6

RNA polymerase as described by the suppliers, e.g., Ambion, Austin, Tex., and by methods well known to those of ordinary skill in the art.

Compounds that inhibited the primary screening assay described above were individually titrated in the same assay at concentrations between 0.1 μM and 200 μM in the absence and presence of 60-fold excess rRNA as a non-specific competitor. A third titration was performed in a heterologous assay using radiolabeled RRE RNA as the target and the complementary biotinylated oligonucleotide 208.92 A. From these three assays, the $IC_{50}$ values and specificity for each compound was calculated.

Results $IC_{50}$ values using rRNA competitor (from Example 1) and radiolabeled RRE RNA are shown in Table 1 for the following ligands. A compound is considered inactive if the titration course does not result in sufficient inhibition to estimate an $IC_{50}$ value. Specificity is calculated as the ratio of RRE+rRNA $IC_{50}$/εRNA+rRNA $IC_{50}$. When an εRNA ligand was inactive in the RRE assay the specificity of the ligand is defined as maximal (max) since a value cannot be calculated.

TABLE 1

$IC_{50}$ Values for 1,3,5-Triazine Compounds

| Compound | Specificity | HBV + rRNA $IC_{50}$ (μM) | RRE + rRNA $IC_{50}$ (μM) |
|---|---|---|---|
| 1 | max. | 32.4 | inactive |
| 2 | max. | 3.2 | inactive |
| 3 | max. | 66.9 | inactive |
| 4 | max. | 16.3 | inactive |
| 5 | max. | 49.3 | inactive |
| 6 | max. | 10.4 | inactive |
| 7 | max. | 2.4 | Inactive |
| 8 | max. | 4 | inactive |
| 9 | 132.6 | 6.2 | inactive |
| 10 | max. | 12 | inactive |
| 11 | max. | 15 | inactive |
| 12 | max. | 2.6 | inactive |
| 13 | max. | 4.9 | inactive |
| 14 | max. | 7.1 | inactive |
| 15 | max. | 11 | inactive |
| 16 | max. | 12.1 | inactive |
| 17 | max. | 15.1 | inactive |
| 18 | max. | 5.1 | inactive |
| 19 | max. | 9.9 | inactive |
| 20 | max. | 11.7 | inactive |
| 21 | max. | 14.4 | inactive |
| 22 | max. | 3.6 | inactive |
| 23 | max. | 5.7 | inactive |
| 24 | max. | 10 | inactive |
| 25 | max. | 11.9 | inactive |
| 26 | max. | 15 | inactive |
| 27 | max. | 15.5 | inactive |
| 28 | max. | 18.9 | inactive |
| 29 | max. | 24.8 | inactive |
| 30 | max. | 25 | inactive |
| 31 | max. | 30 | inactive |
| 32 | max. | 32.6 | inactive |
| 33 | max. | 37.2 | inactive |
| 34 | max. | 21 | inactive |
| 35 | max. | 24.9 | inactive |
| 36 | 53.8 | 28.9 | 1553.8 |
| 37 | max. | 30.1 | inactive |
| 38 | max. | 34.9 | inactive |
| 39 | max. | 39.9 | inactive |
| 40 | max. | 21.9 | inactive |
| 41 | max. | 24.9 | inactive |
| 42 | max. | 30 | inactive |
| 43 | max. | 30.1 | inactive |
| 44 | max. | 35 | inactive |
| 45 | max. | 39.9 | inactive |
| 46 | max. | 23.1 | inactive |
| 47 | max. | 25 | inactive |
| 48 | max. | 30 | inactive |
| 49 | max. | 35 | inactive |
| 50 | max. | 39.9 | inactive |
| 51 | max. | 39.9 | inactive |
| 52 | max. | 66 | inactive |
| 53 | max. | 70.1 | inactive |
| 54 | max. | 89.9 | inactive |
| 55 | max. | 100.1 | inactive |
| 56 | max. | 42.1 | inactive |
| 57 | max. | 50.1 | inactive |
| 58 | max. | 200.4 | inactive |
| 59 | max. | 90.1 | inactive |
| 60 | max. | 100.1 | inactive |
| 61 | max. | 42.6 | inactive |
| 62 | max. | 54.3 | inactive |
| 63 | max. | 69 | inactive |
| 64 | max. | 71.9 | inactive |
| 65 | max. | 99.9 | inactive |
| 66 | max. | 113.5 | inactive |
| 67 | max. | 47.7 | inactive |
| 68 | max. | 33 | inactive |
| 69 | max. | 70 | inactive |
| 70 | max. | 80.6 | inactive |
| 71 | max. | 99.9 | inactive |
| 72 | max. | 119.9 | inactive |
| 73 | max. | 120 | inactive |
| 74 | max. | 125.9 | inactive |
| 75 | max. | 160.1 | inactive |
| 76 | max. | 200 | inactive |
| 77 | max. | 120 | inactive |
| 78 | max. | 133.2 | inactive |
| 79 | max. | 168.9 | inactive |
| 80 | max. | 200 | inactive |
| 81 | max. | 120.1 | inactive |
| 82 | max. | 149.9 | inactive |
| 83 | max. | 184.7 | inactive |
| 84 | max. | 120.1 | inactive |
| 85 | max. | 53.8 | inactive |
| 86 | max. | 200 | inactive |
| 87 | 37.0 | 8.1 | 300.1 |
| 88 | 80.2 | 11.7 | 937.8 |
| 89 | 6.0 | 12.5 | 75.3 |
| 90 | 3.0 | 15 | 44.9 |
| 91 | 46.8 | 17.1 | 800 |
| 92 | 4.0 | 2.5 | 10.1 |
| 93 | max | 12.7 | Inactive |
| 94 | 20.8 | 12 | 249.7 |
| 95 | 2.8 | 13.7 | 39 |
| 96 | 5.0 | 15 | 75 |
| 97 | 22.2 | 17.8 | 394.8 |
| 98 | 2.7 | 3 | 8.1 |
| 99 | max | 11.5 | inactive |
| 100 | 49.6 | 12.1 | 600 |
| 101 | 3.6 | 14 | 50.1 |
| 102 | 3.0 | 15.1 | 45.1 |
| 103 | 10.0 | 20 | 200.1 |
| 104 | 15.1 | 5 | 74.9 |
| 105 | 8.1 | 9.9 | 80.1 |
| 106 | 5.8 | 12.1 | 70.1 |
| 107 | 1.7 | 14.9 | 25 |
| 108 | 2.5 | 16.1 | 40 |
| 109 | 1.8 | 20 | 35 |
| 110 | 4.0 | 20 | 79.9 |
| 111 | 20.0 | 23 | 460.3 |
| 112 | 30.0 | 25 | 750.6 |
| 113 | 9.1 | 33.1 | 300 |
| 114 | 5.5 | 40 | 220 |
| 115 | 1.7 | 75.1 | 130.1 |
| 116 | 1.3 | 20 | 25.1 |
| 117 | max. | 15.6 | inactive |
| 118 | 2.0 | 25 | 50.1 |
| 119 | 7.1 | 35 | 250.1 |
| 120 | 24.1 | 46 | 1109.1 |

TABLE 1-continued

IC$_{50}$ Values for 1,3,5-Triazine Compounds

| Compound | Specificity | HBV + rRNA IC$_{50}$ ($\mu$M) | RRE + rRNA IC$_{50}$ ($\mu$M) |
|---|---|---|---|
| 121 | 5.0 | 79.9 | 400.1 |
| 122 | 14.9 | 20.1 | 300 |
| 123 | 3.0 | 25 | 74.9 |
| 124 | 10.0 | 29.9 | 300 |
| 125 | 28.5 | 35.1 | 1000 |
| 126 | 8.3 | 60.1 | 500.5 |
| 127 | 1.0 | 80 | 80 |
| 128 | 4.5 | 22 | 99.9 |
| 129 | 4.8 | 25 | 120 |
| 130 | 12.2 | 32.9 | 400 |
| 131 | 1.0 | 36.7 | 36.7 |
| 132 | 11.4 | 70.1 | 800 |
| 133 | 1.0 | 99.9 | 99.9 |
| 134 | 2.0 | 100.1 | 200 |
| 135 | 2.0 | 149.9 | 300.1 |
| 136 | 5.0 | 203.4 | 1017.2 |
| 137 | 1.0 | 400 | 400 |
| 138 | 0.1 | 500 | 49.9 |
| 139 | 0.2 | 2094.3 | 400.2 |
| 140 | 4.2 | 120 | 499.9 |
| 141 | 1.3 | 165.4 | 214.5 |
| 142 | 5.0 | 226 | 1129.9 |
| 143 | 0.5 | 445.9 | 223 |
| 144 | 0.1 | 1000 | 99.9 |
| 145 | 3.1 | 129.9 | 400 |
| 146 | 6.1 | 196 | 1194.9 |
| 147 | 1.0 | 299.9 | 299.9 |
| 148 | max. | 496.9 | inactive |
| 149 | 0.4 | 1000.1 | 399.9 |
| 150 | 4.7 | 149.9 | 700.8 |
| 151 | 3.5 | 200.0 | 699.9 |
| 152 | 0.5 | 299.9 | 150 |
| 153 | 1.0 | 499.9 | 499.9 |
| 154 | 0.3 | 1180.6 | 300 |
| 155 | max. | 25.5 | inactive |
| 156 | max. | 22.8 | inactive |
| 157 | max. | 2.9 | inactive |
| 158 | max. | 7.4 | inactive |
| 159 | max. | 2.7 | inactive |
| 160 | 44.2 | 9.5 | 420.2 |
| 161 | max. | 36.1 | inactive |
| 162 | max. | 11.7 | inactive |
| 163 | max. | 99 | inactive |
| 164 | max. | 48 | inactive |
| 165 | max. | 18.8 | inactive |
| 166 | max. | 36.3 | inactive |
| 167 | max. | 50.9 | inactive |
| 168 | max. | 19.7 | inactive |
| 169 | max. | 15.4 | inactive |
| 170 | 119.3 | 6.2 | 739.9 |
| 171 | max. | 9.4 | inactive |
| 172 | max | 69.2 | inactive |
| 173 | max. | 89 | inactive |
| 174 | 201.1 | 5.6 | 1126.3 |
| 175 | max. | 5.9 | inactive |
| 176 | 166.5 | 6.8 | 1132.5 |
| 177 | max. | 6.2 | inactive |
| 178 | max. | 12.7 | inactive |
| 179 | max. | 13.2 | inactive |
| 180 | max. | 13.7 | inactive |
| 181 | max. | 60 | inactive |
| 182 | max. | 70.4 | inactive |
| 183 | max. | 47.8 | inactive |
| 184 | 2.0 | 1.7 | 3.4 |
| 185 | max. | 203.3 | inactive |
| 186 | max. | 88.4 | inactive |
| 187 | max. | 61 | inactive |
| 188 | max. | 54.9 | inactive |
| 189 | | inactive | inactive |
| 190 | max. | 223.7 | inactive |
| 191 | max. | 87 | inactive |
| 192 | max. | 235 | inactive |
| 193 | max. | 28 | inactive |
| 194 | max. | 34 | inactive |
| 195 | max. | 28.2 | inactive |
| 196 | max. | 32.7 | inactive |
| 197 | | inactive | inactive |
| 198 | max. | 14.8 | inactive |
| 199 | max. | 33.8 | inactive |
| 200 | max. | 12.1 | inactive |
| 201 | max. | 53 | inactive |
| 202 | max. | 68 | inactive |
| 203 | 85.6 | 15.6 | 1334.6 |
| 204 | max. | 18.4 | inactive |
| 205 | max. | 19.1 | inactive |
| 206 | max. | 12.4 | inactive |
| 207 | max. | 35.9 | inactive |
| 208 | max. | 38.2 | inactive |
| 209 | max. | 9.3 | inactive |
| 210 | max. | 3.3 | inactive |
| 211 | 20.2 | 5.5 | 111 |
| 212 | max. | 23.1 | inactive |
| 213 | 33.3 | 15.6 | 518.8 |
| 214 | max. | 42.6 | inactive |
| 215 | max. | 50 | inactive |
| 216 | max. | 9 | inactive |
| 217 | max. | 8.1 | inactive |
| 218 | 12.0 | 4.8 | 57.8 |
| 219 | | inactive | inactive |
| 220 | 33.3 | 27.6 | 918.5 |
| 221 | max. | 402.8 | inactive |
| 222 | max. | 48 | inactive |
| 223 | max. | 48.8 | inactive |
| 224 | max. | 60.1 | inactive |
| 225 | max. | 193.3 | inactive |
| 226 | 5.0 | 84.4 | 422 |
| 227 | max. | 12.8 | inactive |
| 228 | max. | 79.3 | inactive |
| 229 | max. | 4.4 | inactive |
| 230 | max. | 20.9 | inactive |
| 231 | max. | 195.4 | inactive |
| 232 | max. | 45.5 | inactive |
| 233 | max. | 22.9 | inactive |
| 234 | max. | 48.2 | inactive |
| 235 | max. | 9.9 | inactive |
| 236 | | inactive | inactive |
| 237 | max. | 51.6 | inactive |
| 238 | max. | 1071 | inactive |
| 239 | max. | 22.8 | inactive |
| 240 | | inactive | inactive |
| 241 | max. | 5.7 | inactive |
| 242 | 2.5 | 54.2 | 135.6 |
| 243 | max. | 86.7 | inactive |
| 244 | | inactive | inactive |
| 245 | max. | 8.1 | inactive |
| 246 | max. | 5.6 | inactive |
| 247 | max. | 6.7 | inactive |
| 248 | | inactive | inactive |
| 249 | max. | 47.2 | inactive |
| 250 | | inactive | inactive |
| 251 | max. | 45 | inactive |
| 252 | | inactive | inactive |
| 253 | 59.9 | 11 | 658.8 |
| 254 | 3.7 | 87.7 | 328.7 |

Example 2
Determination of Antiviral Activity
 i. Materials and Methods

The antiviral activity of the compounds of the present invention is measured by the methods described in Korba and Gering, Antiviral Res. 19: 55–70 (1992).

Whenever possible, all materials were prepared sterile and solutions passed through 0.22 micron filters.

Materials
 1. HBV hybridization probe: A 3.2 kb full genome length HBV fragment was retrieved from a restriction digest of a plasmid clone (e.g., pAM6) electrophoresed in a 1% agarose gel, isolated, and stored at −20° C.

2. HBV gel standard: 1.0 μl HBV standards (100 ng/ml) plus 5 μl tracking dye and 14 μl TE (per lane). HBV standards were made by performing separate Bam HI and Eco RI digests of cloned HBV DNA. The digests were combined in equimolar amounts and stored at −20° C. This produced several HBV fragment (positive hybridization controls) as well as non-HBV plasmid DNA fragments (negative hybridization control). For example, pAM6 produces HBV DNA fragments of 3.2, 1.85, and 1.35 kb, as well as a plasmid fragment of 4.3 kb. This mixture served as a positive and a negative hybridization control, a size standard, and a quantitation standard that occupied only one lane of a gel.

3. HBV media standards: Culture medium (RP2) was collected from confluent non-G418 treated 2.2.15 cells and stored frozen at −70° C. Aliquots were pooled as necessary (typically 1–2 liters) and centrifuged at 7000×g, 10 minutes to remove cellular debris. The supernatant was added to an Amicon Inc. "stirred cell" (8400 series) fitted with a YM100 membrane (cat. No. 13642) 400 ml, and ultrafiltered at approximately 20 psi nitrogen with constant stirring, at 4° C. (approximately 3–5 hours), to insure that the membrane was not allowed to dry. This resulted in approximately a 40-fold concentration by volume. HBV DNA content in the concentrated sample was quantitated by blot hybridization against a known standard quantity of HBV DNA. Approximately a 2-fold loss of HBV DNA (as compared to the theoretical starting concentration) frequently occurred during this process. The final product was diluted to a standard concentration of long HBV DNA/ml with RPMI 1640 (without FBS). The concentration was then rechecked by blot hybridization. The adjusted standard pool was again rechecked by blot hybridization. The adjusted standard pool was stored at −70° C. in 5 ml aliquots in screw-capped tubes and stable for at least 5 years.

ii. Guidelines for the Culture of 2.2.15 Cells

Cell cultures were handled aseptically, without antibiotics, and in contained facilities (BS level II). The basal culture medium used for the culture of 2.2.15 cells was RPMI 1640. Fetal Bovine Serum (FBS) was added at either 2% or 4% final concentration, and was not heat inactivated or lot tested. L-Glutamine was added to a final concentration of 4 mM. Complete culture medium was stored at 4° C. for up to 4 weeks. Cells were grown and maintained at 37° C. in a 5% $CO_2$ humidified atmosphere.

Flasks and plates were routinely seeded at a density of 3–5×$10^4$ cells $cm^2$. This seeding density produced confluent cultures in 3–5 days. Seeding densities of approximately 1×$10^4$ cells/$cm^2$ were permissible and prolonged time to confluence. At confluence, cells were at a density of 3–5× $10^5$ cells/$cm^2$ and produced their maximal and relatively stable levels of HBV. A confluent, "healthy" T-75 flask, grown in medium with 4% FBS was subcultured in up to 6, 96-well or 24-well flat bottom plates.

iii. "Primary" or "Screening" Assay (96-well plate format)

This assay format is well suited to the screening of test compounds for potential antiviral activity. The assay provides a threshold assessment of antiviral activity by measuring (i) the levels of HBV virion release from the cells and (ii) cytotoxicity. Two rows of cells were used for each compound, and 4 rows for the assay controls (two for untreated, and two for positive antiviral control, e.g., 3TC).

After incubating in the presence of test compound for 9 days, the media were harvested, transferred to 96-well U-bottom plates, and centrifuged. The supernatants were transferred to tubes for dot blot hybridization analysis of HBV virion DNA. The medium was aspirated off of the toxicity plates and discarded. Toxicity plates were then incubated with neutral red dye (MTT can also be used if preferred), washed with DPBS, developed with an acetic acid-ethanol solution, and assayed in a plate reader.

There are many options as to what concentration ranges to use for these assays. The compounds of the present invention were tested for toxicity at as high a concentration as the compound's solubility and the toxicity of the diluent (frequently DMSO) allowed. The 2.2.15 cells will tolerate 2–3% DMSO for up to 10 days with little loss of viability.

1. 2.2.15 cells were seeded into 96-well, flat bottom tissue culture plates as described above. Duplicate plates were used for the antiviral treatments for each test compound (up to 8 compounds per pair of plates); after three to four days, cells were confluent and medium was yellow in color; the medium was removed and replaced with 100 μl RP2 24 hours before the beginning of drug treatment.

2a. Compounds were prepared for antiviral treatment as follows:

i) For each compound, a total of 4 concentrations were examined; this required 9 sets of 4 sterile, 1.1 ml minitubes (36 tubes per compound). Into the first tube of each set, sufficient compound was aliquoted to make up 700 μl (for 10-fold dilution series) or 980 μl (for 3.3-fold dilution series) of the highest test concentration; the other tubes were left empty.

ii) The sample aliquots for the last day of treatment were set up at a 3 fold higher concentration relative to the other aliquots; this was done to provide sufficient material for DNA analysis (see below).

iii) The tubes were covered with the rack lids, labelled appropriately, and stored at −20° C. or the appropriate temperature for the test compounds; this procedure prevents multiple freeze-thaw cycles of stock solutions of the test compound, and ensures that all 9 daily test aliquots are treated in an identical manner with respect to temperature variations. If compounds were stored at 4° C., the tops of the tubes were covered with a sheet of parafilm to prevent evaporation.

2b. Compounds were prepared for toxicity treatment as follows: For each compound, a total of 4 concentrations were examined. This required 9 sets of 4 sterile, 1.1 ml minitubes (36 tubes per compound). Into the first tube of each set, sufficient compound was aliquoted to make up 465 μl of the highest test concentration. The other tubes were left empty. The tubes were covered with the rack lids, and stored at −20° C. or at an appropriate temperature. Tubes for the last day of treatment for toxicity testing contain the same amount of compound as used the previous days (not 3xas for the antiviral assays).

3a. The compound dilution series was prepared for antiviral treatment as follows:

i) For a 10-fold dilution series: to the first (compound containing) tube was added 700 μl (175 μl×4). 630 μl (210 μl×3) RP2 culture medium was added to the remaining 3 tubes. The first tube was mixed by pipeting up and down with a pipetman (a multichannel pipetman permits the simultaneous processing of multiple compounds). 70 μl of test compound-containing medium were serially transferred from the first tube to the other 3 tubes, taking care to thoroughly mix each tube before transferring medium;

ii) For a 3.3-fold dilution series: 960 $\mu$l (160 $\mu$l×6) of RP2 was added to the first tube (containing the aliquot of compound) and 640 $\mu$l (160 $\mu$l×4) RP2 was added to each of the empty tubes. 280 $\mu$l of test compound-containing medium were serially transferred from the first tube to the other 3 tubes.

3b. The cytotoxicity of test compounds was analyzed in a 3.3-fold dilution series as follows. 485 $\mu$l (155 $\mu$l×3) of RP2 were added to the first tube (containing the aliquot of compound) and 310 $\mu$L (155 $\mu$l×2) RP2 to each of the 3 remaining tubes. 150 $\mu$l of test compound-containing medium were serially transferred from the first tube to the other 3 tubes.

4. Treatments were initiated by the following procedure:
   a) The culture medium was removed with care to minimize the time that the cell monolayers are without medium;
   b) 100 $\mu$l of each dilution of every compound was added to each of 6 wells (3 wells per plate) using the configuration listed below as an example. The lowest concentration was added first, and the same tips were used to add the higher concentrations. The untreated cells received 100 $\mu$l RP2 per well (untreated cells have to be carried on only one pair of the antiviral assay plates).

|       | Col. 1–3      | Col. 4–6       | Col. 7–9        | Col. 10–12       |
|-------|---------------|----------------|-----------------|------------------|
| Row A |               | untreated cells |                |                  |
| Row B | drug 1 @ 1X   | drug 1 @ 1/10X | drug 1 @ 1/100X | drug 1 @ 1/1000X |
| Row C | drug 2 @ 1X   | ∀              | ∀               | ∀                |
| Row D | ∀             | ∀              | ∀               | ∀                |
| Row E | ∀             | ∀              | ∀               | ∀                |
| Row F | ∀             | ∀              | ∀               | ∀                |
| Row G | ∀             | ∀              | ∀               | ∀                |
| Row H | ∀             | ∀              | ∀               | drug 7 @ 1/1000  | c) Treatments were repeated daily for 9 days. For the last day of treatment, and additional 200 $\mu$l RP2 were added to each well of the antiviral assay plates after the wells are treated with the test compounds (a total of 300 $\mu$l medium per well).

5. A single plate was used for the toxicity treatments for each test compound (up to 7 compounds per plates since the top row were reserved for untreated cells on every toxicity plate). To initiate the treatments, the culture medium was removed, and 100 $\mu$l of each dilution of every compound were added to each of 3 wells using a configuration similar to that shown above for the antiviral treatments. The untreated cells received 100 $\mu$l RP2 per well. Treatment was repeated daily for 9 days.

6. The assay was terminated and samples harvested for quantitative analysis of HBV virion DNA, by removing the culture medium 24 hours following the 9th day of treatment and storing the culture medium in 96-well U-bottom culture plates. These samples were stored at 4° C. until blotting was performed. Samples were eventually be transferred to −20° C. for long term storage.

iv. Assay for Effects on Intracellular HBV Replication (24-well plate format)

This assay format serves to further define the action of potential antiviral agents by permitting an assessment of the levels of intracellular HBV DNA replicative forms. This type of assay is usually performed on compounds identified as active in the 96-well plate format since the effective antiviral concentrations observed in those experiments can be used as a guide for this type of assay (which is considerably more labor intensive and costly). In general, a 3- to 5-fold higher concentration of compound will be needed than that observed in the antiviral assay to produce similar levels of effects on intracellular HBV DNA replication. 2.2.15 cells are seeded in 24-well plates for this assay and treated with test compounds for 9 days. The medium is collected at the end of the treatment period for analysis of HBV virion DNA. For analysis of intracellular HBV DNA, the monolayers are lysed with guanidine thiocyanate/sarcosyl/$\beta$ME, dialyzed, digested with SDS/Proteinase K, extracted with phenol and chloroform, and precipitated with sodium acetate/isopropanol. The intracellular DNAs are then resuspended, digested with Hind III, subjected to gel electrophoresis, and transferred to nitrocellulose for hybridization analysis.

1. 24-well culture plates are seeded as described above. The day before the addition of compounds, the medium is changed to RP2 (0.5 ml per well). As in the 96-well plate assay, duplicate plates are used. A total of 2 wells on each plate are treated with each dilution of compound (4 wells per dilution).

2. Compounds are prepared for antiviral treatment as follows: For each compound, a total of 4 concentrations are examined. This requires 9 sets of 4 sterile, 1.1 ml minitubes (36 tubes per compound). Into the first tube of each set, sufficient compound is aliquoted to make up 2.2 ml of drug-containing medium (additional medium to make up the proper total volume was added at the time of cell treatment (see step 4 below). Tubes for the last day of treatment for toxicity testing contain the same amount of compound as used the previous days (not 3× as for the 96-well plate assay). The tubes are covered with the rack lids, and stored at −20° C. or at an appropriate temperature.

3. Compounds in this assay are tested in a 3.3-fold dilution series. To make this dilution series, 720 $\mu$l (240 $\mu$l×3) are added to the first tube. 460 $\mu$l (230 $\mu$l×2) of medium are added to the remaining 3 tubes. 200 $\mu$l are serially transferred from the first tube to the remaining 3 tubes.

4. Wells are treated from the lowest concentration of drug to the highest, adding 100 $\mu$l to each of the 4 wells. An additional 400 $\mu$l of RP2 (without drugs) are added to each well. Culture medium is continually changed and test compounds are added each day for a total of 9 days.

5. 24-hours following the final addition of compound, the culture medium is collected and stored in new 24-well plates. A 250 $\mu$l aliquot of each stored culture medium sample is transferred to a 96-well U-bottomed culture plates (one plate can hold samples from up to 4, 24-well plates), and stored at 4° C. until dot blotting is performed.

6. The cell monolayers are then lysed for analysis of intracellular HBV DNA as described above.

vi. Neutral Red Dye Determination of Drug Toxicity

The antiviral effect of any compound was evaluated relative to its toxicity. Cells were seeded and treated following the guidelines above, after which a neutral red dye uptake assay was performed to assess toxicity as described below. Other assays of cytotoxicity (e.g., MTT) can be substituted for the procedure described below. Note that this procedure assesses toxicity under culture and treatment conditions which are identical to those used for the antiviral analyses, thereby permitting a determination as to whether the reduction in virus production due to a specific antiviral effect or due to a cytotoxic effect on the host cell. Since the cultures, by necessity, are at confluence, the cytotoxic effects of the test compounds will probably be reduced relative to the cytotoxic effects that would be expected for actively dividing cells.

1. Cultures were treated with test compounds on the designated toxicity plates as described above.
2. The culture medium was carefully removed 24 hours following the 9th day of treatment. The monolayer was fully removed in the top left three wells (row A, col. 1–3). These wells were used as "blanks" for the plate reader.
3. 100 μl DPBS (containing 0.01% neutral red dye) were added to each well, including the empty wells, and Incubated in the tissue culture incubator for 30 minutes.
4. The dye was removed carefully and gently, using a multichannel pipetman since the monolayers can become fragile after incubation with neutral red dye. 200 μl DPBS were added to all the wells taking care not to displace the monolayers. The DPBS was removed and 100 μl 50% EtOH/1% glacial acetic acid (in $H_2O$) were added to each well. The plates were mixed for 15 minutes on an orbital platform shaker (120–150 RPM) to allow for full extraction of the dye from the cells.
5. Optical absorbance at 510 nm was read in an ELISA type plate reader, using the 3 empty wells to set the background. An average absorbance value was calculated for the 9 untreated cultures on a plate, and the absorbance of dye for the treated cultures on the same plate was expressed as a percentage of that value. This procedure was repeated for each individual plate.

Table 2 shows the antiviral activity of a group of εRNA ligands. The micromolar concentration at which the production of extra-cellular virus was reduced by 50% ($EC_{50}$) and was reduced by 90% ($EC_{90}$) is reported. Because HBV does not cause cell death, the cytotoxic potential of the compounds can also be estimated in the same cultures by measuring cell death by the neutral red uptake method, as described above. This value is expressed by 50% cell death ($CC_{50}$ μM).

TABLE 2

Antiviral Activity of Selected 1,3,5-Triazine Compounds

| Structure | Antiviral $EC_{50}$ (μM) | Antiviral $EC_{50}$ (μM) | 50% Cell Death $CC_{50}$ (μM) |
|---|---|---|---|
| 1 | >100 | >100 | 14 |
| 2 | 33 | 83 | >100 |
| 3 | 4.8 | 17 | >100 |
| 4 | 3.4 | 10 | 3.7 |
| 5 | 0.411 | 1.2 | 307 |
| 6 | 0.3 | 0.7 | 29 |
| 7 | 33 | 89 | 29 |
| 8 | >100 | >100 | 196 |
| 9 | 0.474 | 1.8 | 175 |
| 10 | >100 | >100 | >300 |
| 11 | 3.9 | 15 | 27 |
| 12 | 0.759 | 4.3 | 77 |

TABLE 2-continued

Antiviral Activity of Selected 1,3,5-Triazine Compounds

| Structure | Antiviral $EC_{50}$ (μM) | Antiviral $EC_{50}$ (μM) | 50% Cell Death $CC_{50}$ (μM) |
|---|---|---|---|
| 13 | 8.4 | 208 | >300 |
| 14 | >100 | >100 | >100 |
| 15 | 0.5 | 4 | 0.6 |
| 16 | 15 | 218 | 304 |
| 18 | 6.5 | 32 | 105 |
| 19 | >100 | >100 | >300 |
| 20 | 4.1 | 12 | 7.1 |
| 21 | 5.6 | 18 | 5.6 |
| 22 | >100 | >100 | 47 |
| 23 | 40 | 106 | 145 |
| 24 | 18 | 148 | 75 |
| 25 | 1 | 9.4 | 105 |
| 27 | >100 | >100 | >300 |
| 28 | >100 | >100 | 33 |
| 29 | 1.1 | 6.3 | 15 |
| 30 | 54 | 199 | 230 |
| 33 | >100 | >100 | 50 |
| 34 | 66 | 181 | 41 |
| 35 | 2.3 | 17 | 3.9 |
| 38 | 0.592 | 2.7 | 125 |
| 39 | 1 | 17 | 5.3 |
| 40 | 30 | 79 | 136 |
| 41 | 36 | 122 | >300 |
| 42 | 6.1 | 22 | 237 |
| 43 | 0.841 | 3.9 | 87 |
| 44 | 4.8 | 20 | 285 |
| 46 | >100 | >100 | >100 |
| 49 | 1.2 | 11 | 140 |
| 50 | 29 | 70 | 30 |
| 51 | 15 | 73 | 130 |
| 52 | 4.5 | 24 | 11 |
| 53 | 1.2 | 82. | 72 |
| 56 | >100 | >100 | 63 |
| 61 | 3.7 | 10 | 1.3 |
| 62 | >100 | >100 | >100 |
| 63 | >100 | >100 | >100 |
| 65 | >100 | >100 | 17 |
| 67 | >100 | >100 | >100 |
| 68 | >100 | >100 | >300 |
| 74 | >100 | >100 | >100 |
| 85 | >100 | >100 | 209 |
| 88 | 4.8 | 14 | >100 |
| 91 | >100 | >100 | >300 |
| 93 | 0.006 | 0.503 | 54 |
| 94 | >100 | >100 | >300 |
| 97 | >100 | >100 | 49 |
| 99 | 52 | 162 | 157 |
| 100 | 39 | 172 | 57 |
| 113 | >100 | >100 | >300 |
| 117 | 4.2 | 36 | >300 |
| 120 | >100 | >100 | 45 |
| 125 | 3.9 | 11 | 265 |
| 155 | 0.001 | 0.063 | 59 |
| 156 | 4 | 13 | 359 |
| 157 | 0.71 | 2.9 | 59 |
| 158 | 42 | 129 | 112 |
| 159 | 0.498 | 1.9 | 101 |
| 160 | 0.42 | 4.1 | >300 |
| 161 | 0.55 | 6.8 | >300 |
| 162 | 0.923 | 7.5 | 436 |
| 163 | 0.958 | 7.6 | 150 |
| 164 | 0.863 | 9.7 | 201 |
| 165 | 3.8 | 11 | >300 |
| 166 | 1.4 | 11 | 252 |
| 167 | 1.7 | 12 | 161 |
| 168 | 0.7 | 15 | >300 |
| 169 | 2.5 | 37 | >300 |
| 170 | 4 | 40 | 499 |
| 171 | 5 | 52 | 174 |
| 172 | 5.2 | 64 | >300 |
| 173 | 5 | 68 | 247 |
| 174 | 5.5 | 72 | 133 |
| 175 | 5 | 75 | >300 |
| 176 | 31 | 86 | >300 |

TABLE 2-continued

Antiviral Activity of Selected 1,3,5-Triazine Compounds

| Structure | Antiviral EC$_{50}$ ($\mu$M) | Antiviral EC$_{50}$ ($\mu$M) | 50% Cell Death CC$_{50}$ ($\mu$M) |
|---|---|---|---|
| 177 | 5 | 90 | >300 |
| 178 | 5 | 95 | 272 |
| 179 | 26 | 123 | >300 |
| 180 | 12 | 131 | >300 |
| 181 | 6 | 136 | >300 |
| 182 | 54 | 191 | >300 |
| 183 | 52 | 231 | >300 |
| 184 | 13 | 111 | 441 |
| 185 | 12 | 107 | >300 |
| 186 | 66 | 332 | 771 |
| 187 | 7.1 | 116 | 266 |
| 188 | 12 | 102 | 218 |
| 189 | 2.5 | 60 | 88 |
| 190 | >100 | >100 | 945 |
| 191 | >100 | >100 | 836 |
| 192 | >100 | >100 | 739 |
| 193 | >100 | >100 | 666 |
| 194 | >100 | >100 | 626 |
| 195 | >100 | >100 | 400 |
| 196 | >100 | >100 | 381 |
| 197 | >100 | >100 | 354 |
| 198 | >100 | >100 | 336 |
| 199 | >100 | >100 | 331 |
| 200 | >100 | >100 | 309 |
| 201 | >100 | >100 | >300 |
| 202 | >100 | >100 | >300 |
| 203 | >100 | >100 | >300 |
| 204 | >100 | >100 | >300 |
| 205 | >100 | >100 | >300 |
| 206 | >100 | >100 | >300 |
| 207 | >100 | >100 | >300 |
| 208 | >100 | >100 | >300 |
| 209 | >100 | >100 | >300 |
| 210 | >100 | >100 | >300 |
| 211 | >100 | >100 | >300 |
| 212 | >100 | >100 | >300 |
| 213 | >100 | >100 | >300 |
| 214 | >100 | >100 | >300 |
| 215 | >100 | >100 | >300 |
| 216 | >100 | >100 | >300 |
| 217 | >100 | >100 | >300 |
| 218 | >100 | >100 | >300 |
| 219 | >100 | >100 | >300 |
| 220 | >100 | >100 | >300 |
| 221 | >100 | >100 | >300 |
| 222 | >100 | >100 | >300 |
| 223 | >100 | >100 | >300 |
| 224 | >100 | >100 | >300 |
| 225 | >100 | >100 | 281 |
| 226 | >100 | >100 | 280 |
| 227 | >100 | >100 | 247 |
| 228 | >100 | >100 | 243 |
| 229 | >100 | >100 | 237 |
| 230 | >100 | >100 | 231 |
| 231 | >100 | >100 | 218 |
| 232 | >100 | >100 | 190 |
| 233 | >100 | >100 | 188 |
| 234 | >100 | >100 | 188 |
| 235 | >100 | >100 | 178 |
| 236 | >100 | >100 | 171 |
| 237 | >100 | >100 | 163 |
| 238 | >100 | >100 | 163 |
| 239 | >100 | >100 | 154 |
| 240 | >100 | >100 | 154 |
| 241 | 39 | 111 | 164 |
| 242 | 40 | 117 | 172 |
| 243 | 67 | 280 | 409 |
| 244 | 34 | 103 | 143 |
| 245 | >100 | >100 | 137 |
| 246 | 5.2 | 103 | 141 |
| 247 | >100 | >100 | 136 |
| 248 | >100 | >100 | 135 |
| 249 | >100 | >100 | 134 |
| 250 | >100 | >100 | 123 |
| 251 | >100 | >100 | 96 |
| 252 | 9.5 | 85 | 61 |
| 253 | 18 | 286 | 193 |
| 254 | >100 | >100 | 58 |

The compounds show a potent antiviral activity. In particular, compounds 5 and 6 show antiviral activities with EC$_{90}$ values within 3 to 5-fold of that observed for 3TC (2'deoxy-3-thiacytidine), a well known antiviral drug, in the same assay. The figure ">" represents that no effect was observed at the highest concentration tested.

It is noted that the compounds tested above evidenced a wide range of antiviral activity, with some compounds demonstrating more activity than other compounds. It is believed that all structures 1–254 may have activity against the HBV. However, as is understood by persons of ordinary skill in the art, assay results demonstrating inactivity may be due to a number of factors, such as cell permeability and metabolic stability.

Example 3

Antiviral Combination Therapies

Figure 256:
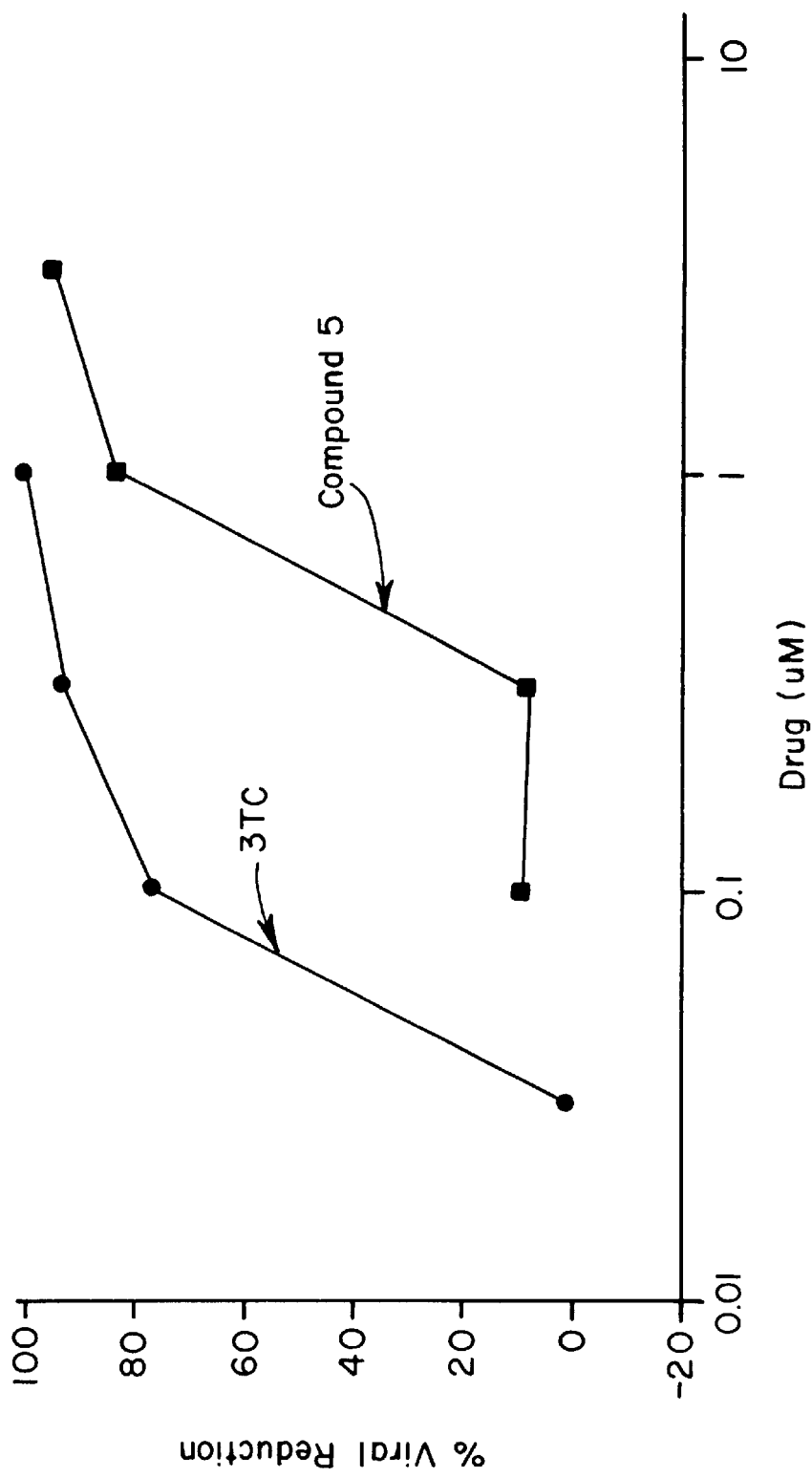
FIG. 256 is a graphical illustration of the reduction in virus production when compound 5 and the antiviral drug 2'-deoxy-3'-thiacytidine were tested at various concentrations alone and in combinations in an antiviral assay using 2.2.15 cells producing HBV.

Compound 5 and 3TC were tested at varying concentrations, alone and in combination, in the antiviral assay outlined in Example 2, above. The reduction in virus production when these drugs were tested independently is shown in FIG. 256. 3TC alone causes 90% viral reduction (EC$_{90}$) at 216 nM, while compound 5 alone exhibits an EC$_{90}$ at 1300 nM.

Figure 247:
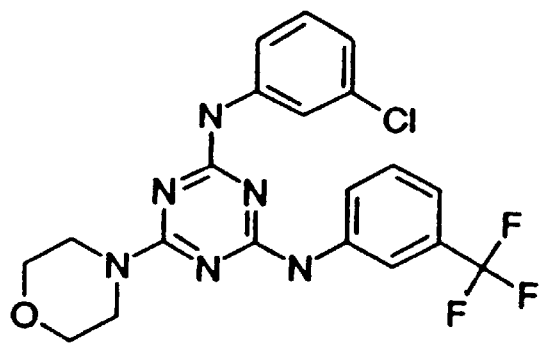
Figure 248:
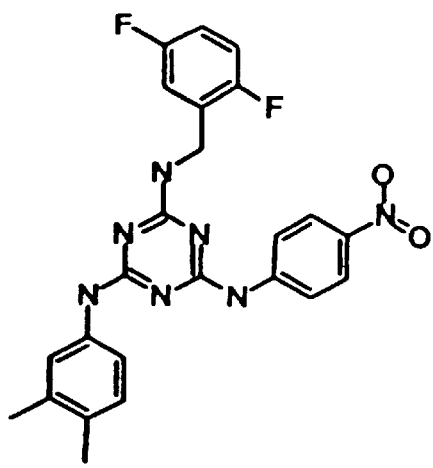
Figure 249:
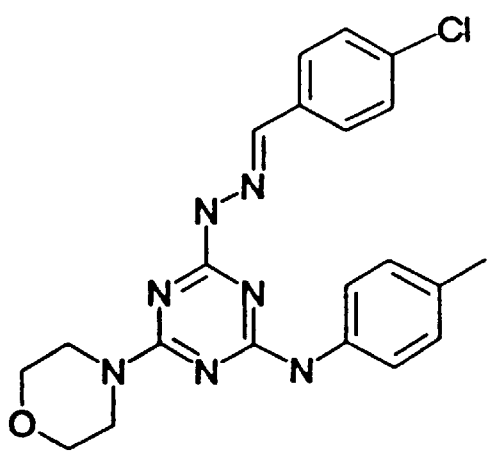
Figure 250:
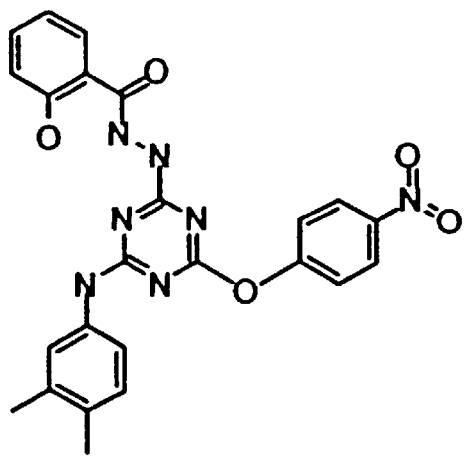
Figure 254:
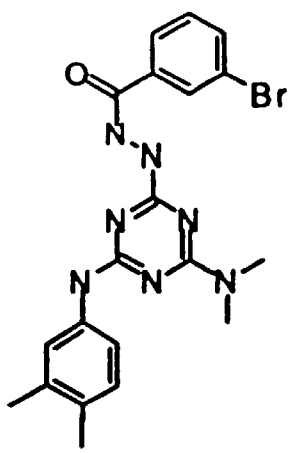
Figure 257C:
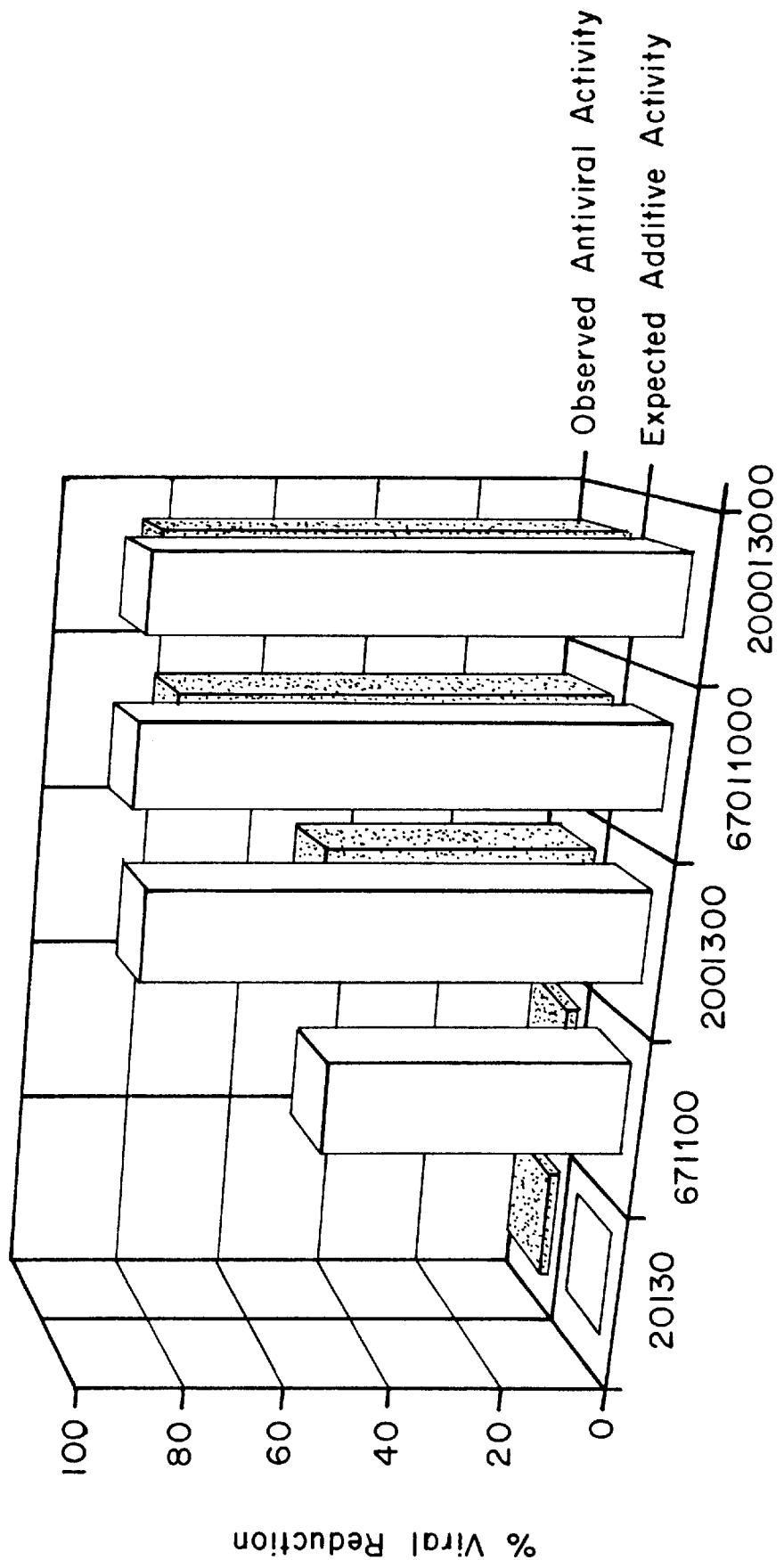

When compounds 5 and 3TC were tested in combination with molar ratios of 1:15, 1:5, and 1:1.5, the results are shown in FIGS. 257A, 247B and 257C. The front row column of each plot shows the expected % viral reduction if the effects of each drug are additive. The back row in each plot shows the observed antiviral activity. The results show a strong synergistic effect when the drugs are mixed at a 1:15 (3TC:compound 5) molar ratio. For example, approximately 7% viral reduction is the expected additive effect of 20 nM 3TC and 300 nM compound 5, but the observed viral reduction reached 92%, which is indicative of a synergistic interaction.

These results suggest that when combined in a 1:15 ratio these two drugs could be used at approximately 4 to 10-fold lower concentrations than those needed when each drug is administered alone.

Example 4

Nucleic Acid Binding of Triazine Compounds

Reaction mixtures (10 $\mu$l) containing 50 mM Tris-HCl, pH 7.5, 50 mM KCl, 0.5 mg/ml rRNA (as a carrier), 0.5 pmol of 3'-end $^{32}$P-labeled $\epsilon$RNA, 0.05 units of B. Cereus RNase, and compound 5 at concentrations between 0 and 200 $\mu$M were incubated at 25° C. for 30 minutes. The reaction products were resolved by gel electrophoresis in polyacrylamide gels. B. Cereus nuclease is a single strand specific RNase. The results are shown in FIG. 258A, wherein the sections of the ladder of digestion products corresponding to cleavage events occurring in the bulge and loop sections of the $\epsilon$RNA structure. It is evident that increasing concentrations (indicated at top) of compound 5 in the reaction results in a decrease in cleavage at specific positions of the bulge indicated by stars. Conversely, the loop and other regions of the structure where not affected. Similar results were obtained using compounds 6, 15, 28, 33, and 61.

These results indicate that the triazine compound bind RNA and that it does so at a site overlapping the bulge region. Moreover, an RNA containing a structural element similar to the bulge of εRNA is likely to be bound by a triazine compound increasing the stability of the RNA structure.

Further, a smaller RNA target containing only the bulge region of εRNA was prepared, and the melting temperature (tm) of this RNA structure was determined by monitoring the change in optical density (OD) at 260 nm while increasing the temperature. A 1 ml aliquot of reaction mixture contained 50 mM NaCl, 10 mM sodium cacodylate, pH 7.0, 10% DMSO, and 2 μM bulge RNA.

The results are shown in FIG. 259A. The y-axis shows the first derivative of the change in OD at 260 nm in OD units/degree C. The reaction containing 2 μM RNA and no drug shows that the RNA has a tm of 65° C., and upon addition of 10 μM compound 6, the tm is shifted to 83° C. These results suggest that the RNA structure is stabilized by the ligand.

All patents, applications, test methods, and publications mentioned herein are hereby incorporated by reference.

Many variations of the present invention will suggest themselves to those skilled in the art in light of the above detailed disclosure. All such modifications are within the full extended scope of the appended claims.

What is claimed is:

1. A method of preventing or treating hepatitis B virus infection in a patient in need of such treatment, said method comprising administering a compound of the formula IA:

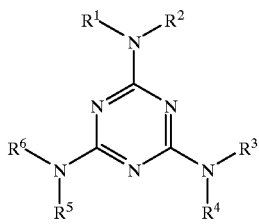

or IB:

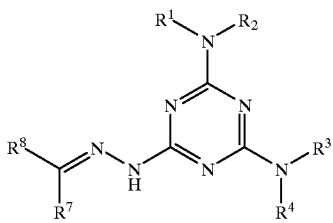

wherein $R^1$, $R^2$, $R^3$, $R^4$, $R^5$, $R^6$, $R^7$ and $R^8$ are each independently selected from the group consisting of hydrogen, alkyl, alkenyl, alkynyl, aryl, heteroaryl, non-aromatic heterocyclic, fused or polycyclic ring and aryloxy;

wherein said alkyl, alkenyl or alkynyl is optionally substituted with one or more substituents selected from the group consisting of halogen, hydroxy, alkyl, nitro, trihalomethyl, aryl, aryloxy, alkoxy, amino, carbonyl, carboxyl, ester, amide, primary, secondary or tertiary amines, cyano, cycloalkyl, alkenyl, cycloalkenyl or alkynyl, and wherein said aryl, aryloxy, heteroaryl, non-aromatic heterocyclic, or fused or polycyclic ring is optionally substituted by one or more substituents selected from the group consisting of halogen, hydroxy, alkyl, nitro, trihalomethyl, aryl, aryloxy, alkoxy, amino, carbonyl, carboxyl, ester, amide, primary, secondary or tertiary amines, cyano, cycloalkyl, alkenyl, cycloalkenyl and alkynyl;

or wherein $R^1$ and $R^2$ together, $R^3$ and $R^4$ together, or $R^5$ and $R^6$ together, optionally form a cycloalkyl or cycloalkenyl ring system, or an unfused polycyclic or monocyclic, non-aromatic heterocyclic or heteroaryl ring system, wherein said ring systems are optionally substituted with one or more substituents selected from the group consisting of halogen, hydroxy, alkyl, nitro, trihalomethyl, aryl, aryloxy, alkoxy, amino, carbonyl, carboxyl, ester, amide, primary, secondary or tertiary amines, cyano, cycloalkyl, alkenyl, cycloalkenyl and alkynyl;

or wherein $R^7$ and $R^8$ together optionally form a cycloalkyl, cycloalkenyl, non-aromatic heterocyclic, or fused or polycyclic ring wherein said cycloalkyl, cycloalkenyl, non-aromatic heterocyclic, or fused or polycyclic ring are optionally substituted with one or more substituents selected from the group consisting of halogen, hydroxy, alkyl, nitro, trihalomethyl, aryl, aryloxy, alkoxy, amino, carbonyl, carboxyl, ester, amide, primary, secondary or tertiary amines, cyano, cycloalkyl, alkenyl and alkynyl, with the proviso that when $R^7$ and $R^8$ together form a non-fused polycyclic ring, the moiety of the non-fused polycyclic ring that binds with N is non-aromatic, and pharmaceutically acceptable salts thereof, and a pharmaceutically acceptable carrier or diluent, wherein said compound is administered in an amount and for a time sufficient to inhibit viral replication.

2. The method of claim 1, wherein said method comprises administering a compound of formula IB wherein one of $R^1$ or $R^2$ is an optionally substituted aryl.

3. The method of claim 1, wherein said method comprises administering a compound of formula IB wherein one of $R^7$ or $R^8$ is an optionally substituted aryl.

4. The method of claim 1, further comprising administering at least one component selected from the group consisting of one or more additional nontriazine based antiviral agents, and mixtures thereof.

5. The method of claim 1, wherein said antiviral formulation is administered orally.

6. The method of claim 1, wherein said compound is administered at a dosage of 0.1 to 250 mg/Kg/day.

7. A method of preventing or treating viral infection in a patient in need of such treatment, said method comprising administering a compound of the formula IA:

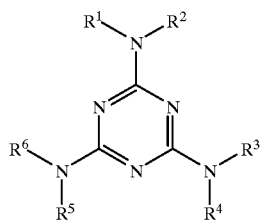

or IB:

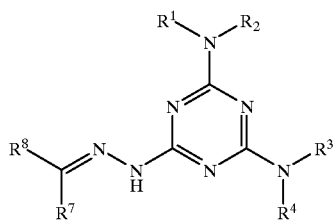

wherein $R^1$, $R^2$, $R^3$, $R^4$, $R^5$, $R^6$, $R^7$ and $R^8$ are each independently selected from the group consisting of hydrogen, alkyl, alkenyl, alkynyl, aryl, heteroaryl, non-aromatic heterocyclic, fused or polycyclic ring and aryloxy;

wherein said alkyl, alkenyl or alkynyl is optionally substituted with one or more substituents selected from the group consisting of halogen, hydroxy, alkyl, nitro, trihalomethyl, aryl, aryloxy, alkoxy, amino, carbonyl, carboxyl, ester, amide, primary, secondary or tertiary amines, cyano, cycloalkyl, alkenyl, cycloalkenyl or alkynyl, and wherein said aryl, heteroaryl, non-aromatic heterocyclic or fused or polycyclic ring is optionally substituted by one or more substituents selected from the group consisting of halogen, hydroxy, alkyl, nitro, trihalomethyl, aryl, aryloxy, alkoxy, amino, carbonyl, carboxyl, ester, amide, primary, secondary or tertiary amines, cyano, cycloalkyl, alkenyl, cycloalkenyl and alkynyl;

or wherein $R^1$ and $R^2$ together, $R^3$ and $R^4$ together, or $R^5$ and $R^6$ together, optionally form a cycloalkyl or cycloalkenyl ring system, or an unfused polycyclic or monocyclic, non-aromatic heterocyclic or heteroaryl ring system, wherein said ring systems are optionally substituted with one or more substituents selected from the group consisting of halogen, hydroxy, alkyl, nitro, trihalomethyl, aryl, aryloxy, alkoxy, amino, carbonyl, carboxyl, ester, amide, primary, secondary or tertiary amines, cyano, cycloalkyl, alkenyl, cycloalkenyl and alkynyl, or wherein $R^7$ and $R^8$ together optionally form a cycloalkyl, cycloalkenyl, non-aromatic heterocyclic, or fused or polycyclic ring wherein said cycloalkyl, cycloalkenyl, non-aromatic heterocyclic, or fused or polycyclic ring are optionally substituted with one or more substituents selected from the group consisting of halogen, hydroxy, alkyl, nitro, trihalomethyl, aryl, aryloxy, alkoxy, amino, carbonyl, carboxyl, ester, amide, primary, secondary or tertiary amines, cyano, cycloalkyl, alkenyl and alkynyl, with the proviso that when $R^7$ and $R^8$ together form a non-fused polycyclic ring, the moiety of the non-fused polycyclic ring that binds with N is non-aromatic;

and pharmaceutically acceptable salts thereof,
and a pharmaceutically acceptable carrier or diluent wherein said compound is administered in an amount and for a time sufficient to inhibit viral replication.

8. The method of claim 7, wherein said method comprises administering a compound of formula IB wherein one of $R^1$ or $R^2$ is an optionally substituted aryl.

9. The method of claim 7, wherein said method comprises administering a compound of formula IB wherein one of $R^7$ or $R^8$ is an optionally substituted aryl.

10. The method of claim 7, wherein said compound is co-administered with at least one component selected from the group consisting of one or more additional non-triazine based antibiotic agents and mixtures thereof.

11. The method of claim 7 wherein said compound is administered orally.

12. The method of claim 7 wherein said compound is administered at a dosage of 0.1 to 250 mg/Kg/day.

13. The method of claim 1, wherein said compound is a compound of formula IB and is selected from the group consisting of 2-fluorobenzaldehyde N-[4-(benzylamino )-6-(tert-butylamino)-1,3,5-triazin-2-yl]hydrazone;

2-hydroxybenzaldehyde N-[4-(benzylamino )-6-(diethylamino)-1,3,5-triazin-2-yl]hydrazone;

benzaldehyde N-[4-(dibutylamino)-6-(4-nitroanilino)-1,3,5-triazin-2-yl]hydrazone;

4-chlorobenzaldehyde N-[4-(2-methylanilino)-6-(4-nitroanilino)-1,3,5-triazin-2-yl]hydrazone;

benzaldehyde N-[4-(piperidyl)-6-(anilino)-1,3,5-triazin-2-yl]hydrazone;

2-methylindolcarboxaldehye N-[4-( morpholino)-6-(anilino)-1,3,5-triazin-2-yl]hydrazone;

4-nitrophenyl N-[4-(dibutylamino)-6-(4-nitroanilino)-1,3,5-triazin-2-yl]hydrazone; and benzaldehyde N-[4-(anilino)-6-(2,4-dimethyl-anilino)-1,3,5-triazin-2-yl]hydrazone;

or a pharmaceutically acceptable salt thereof.

14. The method of claim 7, wherein said compound is a compound of formula IB and is selected from the group consisting of 2-fluorobenzaldehyde N-[4-(benzylamino )-6-(tert-butylamino)-1,3,5-triazin-2-yl]hydrazone;

2-hydroxybenzaldehyde N-[4-(benzylamino )-6-(diethylamino)-1,3,5-triazin-2-yl]hydrazone;

benzaldehyde N-[4-(dibutylamino)-6-(4-nitroanilino)-1,3,5-triazin-2-yl]hydrazone;

4-chlorobenzaldehyde N-[4-(2-methylanilino)-6-(4-nitroanilino)-1,3,5-triazin-2-yl]hydrazone;

benzaldehyde N-[4-(piperidyl)-6-(anilino)-1,3,5-triazin-2-yl]hydrazone;

2-methylindolcarboxaldehye N-[4-( morpholino)-6-(anilino)-1,3,5-triazin-2-yl]hydrazone;

4-nitrophenyl N-[4-(dibutylamino)-6-(4-nitroanilino)-1,3,5-triazin-2-yl]hydrazone; and benzaldehyde N-[4-(anilino)-6-(2,4-dimethyl-anilino)-1,3,5-triazin-2-yl]hydrazone;

or a pharmaceutically acceptable salt thereof.

* * * * *